United States Patent
Cohen et al.

(10) Patent No.: US 12,152,317 B2
(45) Date of Patent: Nov. 26, 2024

(54) TRANSFERRIN RECEPTOR-BINDING MOLECULES, CONJUGATES THEREOF AND THEIR USES

(71) Applicants: VECT-HORUS, Marseilles (FR); UNIVERSITE D'AIX-MARSEILLE, Marseilles (FR); CENTRE NATIONAL DE LA RECHERCHE SCIENTIFIQUE, Paris (FR)

(72) Inventors: Romy Cohen, Marseilles (FR); Marion David, Marseilles (FR); Michel Khrestchatisky, Marseilles (FR)

(73) Assignees: VECT-HORUS, Marseilles (FR); UNIVERSITE D'AIX-MARSEILLE, Marseilles (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 614 days.

(21) Appl. No.: 17/421,412

(22) PCT Filed: Jan. 8, 2020

(86) PCT No.: PCT/EP2020/050318
§ 371 (c)(1),
(2) Date: Jul. 8, 2021

(87) PCT Pub. No.: WO2020/144233
PCT Pub. Date: Jul. 16, 2020

(65) Prior Publication Data
US 2022/0090050 A1    Mar. 24, 2022

(30) Foreign Application Priority Data
Jan. 9, 2019 (EP) ..................................... 19305031

(51) Int. Cl.
*C40B 40/10* (2006.01)
*C07K 16/28* (2006.01)
*C12N 15/10* (2006.01)

(52) U.S. Cl.
CPC .......... *C40B 40/10* (2013.01); *C07K 16/2881* (2013.01); *C12N 15/1037* (2013.01); *C07K 2317/24* (2013.01); *C07K 2317/569* (2013.01); *C07K 2317/92* (2013.01)

(58) Field of Classification Search
None
See application file for complete search history.

(56) References Cited

FOREIGN PATENT DOCUMENTS

| EP | 2 008 666 | 12/2008 |
|----|-----------|---------|
| WO | WO 02/057445 | 7/2002 |
| WO | WO 2018/031424 | 2/2018 |

OTHER PUBLICATIONS

Lith et al. (Jan. 3, 2017) Bioconjugate Chemistry vol. 28 pp. 539 to 548.*

(Continued)

*Primary Examiner* — Christian C Boesen
(74) *Attorney, Agent, or Firm* — SALIWANCHIK, LLOYD & EISENSCHENK

(57) ABSTRACT

The invention relates to Variable Domain of Camelid Heavy Chain-only (VHH) molecules which bind TfR and the uses thereof e.g., to transport molecules of pharmaceutical or diagnostic interest into cells and in organs, in pathological conditions including cancer.

14 Claims, 18 Drawing Sheets

Specification includes a Sequence Listing.

(56) References Cited

OTHER PUBLICATIONS

Sirochmanova, I. et al. "Permeability of the Blood-Brain Barrier and Transport of Nanobodies Across the Blood-Brain Barrier" *Folia Veterinaria*, 2018, pp. 59-66, vol. 62, No. 1.

Thom, G. et al. "Enhanced Delivery of Galanin Conjugates to the Brain through Bioengineering of the Anti-Transferrin Receptor Antibody OX26" *Molecular Pharmaceutics*, 2018, pp. 1420-1431, vol. 15, No. 4.

Van Lith, S. A. M. et al. "Legomedicine—A Versatile Chemo-Enzymatic Approach for the Preparation of Targeted Dual-Labeled Llama Antibody-Nanoparticle Conjugates" *Bioconjugate Chemistry*, 2017, pp. 539-548, vol. 28, No. 2.

Written Opinion in International Application No. PCT/EP2020/050318, Apr. 17, 2020, pp. 1-4.

\* cited by examiner

A

B

C

A

B

| VHH-Fc name | Target | Molecular Weight (Da) | Apparent K$_d$ on human TfR (nM) | Apparent K$_d$ on mouse TfR (nM) |
|---|---|---|---|---|
| VHH A-Fc | hTfR mTfR | 77309 | 5.1 (±0.58) | 2.5 (±0.36) |
| VHH A-Fc-Agly | hTfR mTfR | 77255 | 0.61 (±0.18) | 0.44 (±0.12) |
| VHH B-Fc | hTfR mTfR | 77497 | 1.2 (±0.13) | 0.61 (±0.051) |
| VHH Z-Fc | unknown | 78152 | NB | NB |
| Fc-VHH A | hTfR mTfR | 77334 | 1.3 (±0.30) | 22 (±4.7) |
| Fc-VHH B | hTfR mTfR | 77497 | 1.5 (±0.29) | 51 (±10) |
| Fc-VHH Z | unknown | 78266 | NB | NB |

A

B

| VHH name | Target | Molecular Weight (Da) | Theoretical pI | Apparent $K_d$ on human TfR (nM) | Apparent $K_d$ on mouse TfR (nM) |
|---|---|---|---|---|---|
| VHH A | hTfR mTfR | 14854.45 | 6.31 | 2.7 (± 0.40) | 50 (± 13) |
| VHH A10 | hTfR mTfR | 14854.45 | 6.31 | 3.4 (± 0.87) | 159 (± 70) |
| VHH A11 | hTfR mTfR | 14870.45 | 6.31 | 3.4 (± 0.82) | 197 (± 78) |
| VHH A12 | hTfR | 14820.43 | 6.31 | 363 (± 76) | NB |
| VHH A13 | hTfR mTfR | 14840.42 | 6.31 | 3.5 (± 0.97) | 187 (± 76) |
| VHH A14 | hTfR mTfR | 14840.42 | 6.31 | 3.3 (± 0.83) | 158 (± 69) |
| VHH A15 | hTfR mTfR | 14838.45 | 6.31 | 3.7 (± 0.97) | 207 (± 93) |
| VHH A16 | hTfR mTfR | 14836.41 | 6.31 | 4.7 (± 1.2) | 131 (± 55) |
| VHH A17 | hTfR mTfR | 14854.45 | 6.31 | 5.3 (± 1.4) | 208 (± 87) |
| VHH A18 | hTfR mTfR | 14840.42 | 6.31 | 12 (± 3.1) | 416 (± 151) |
| VHH A19 | hTfR mTfR | 14868.48 | 6.31 | 9.2 (± 2.3) | 210 (± 86) |
| VHH Z | unknown | 15073.48 | 6.15 | NB | NB |

A

- VHH A
- VHH B
- VHH A-siGFPst1
- VHH B-siGFPst1
- VHH Z

B

C

Figure 15:
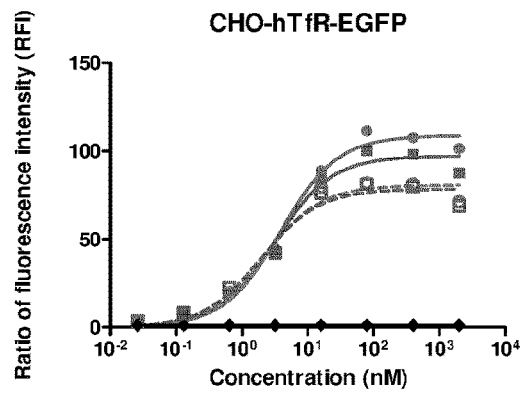
Figure 15:
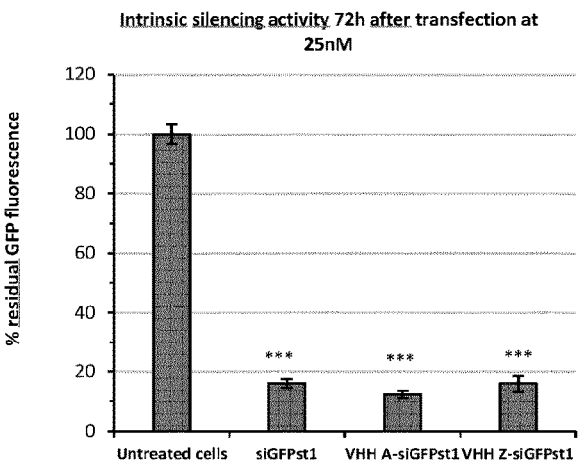
Figure 15:
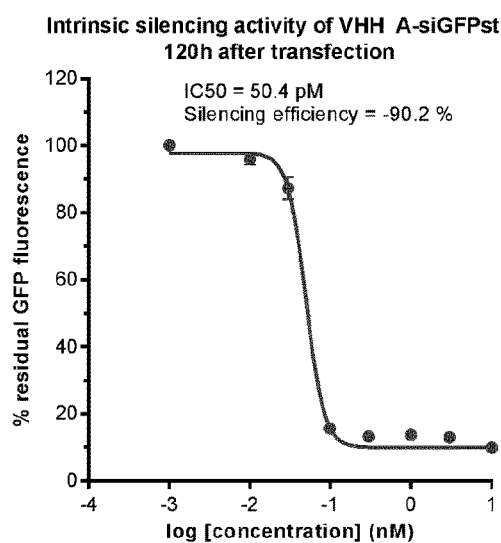

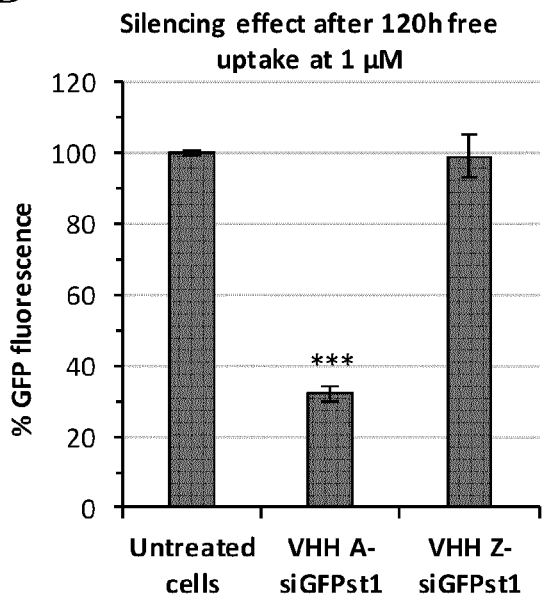
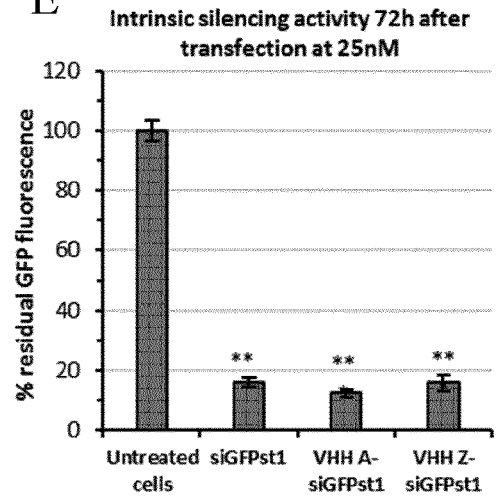
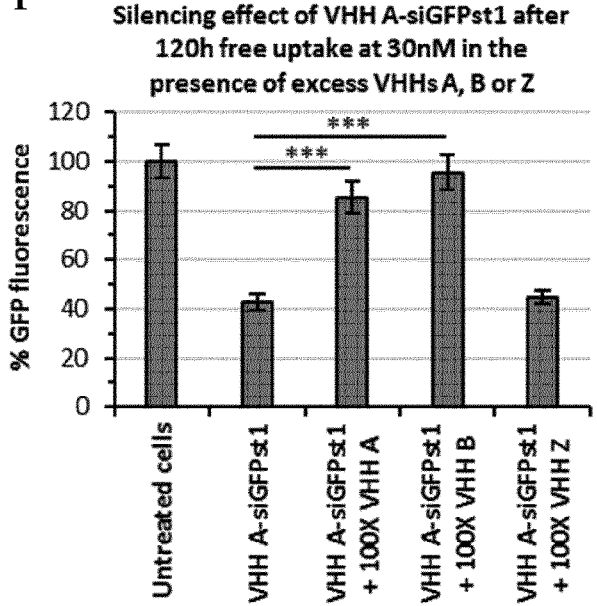
FIGURE 15 (Following)

G
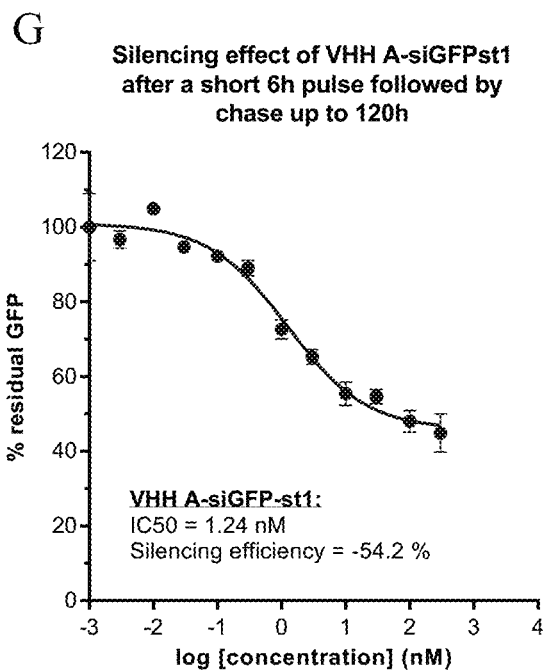
H
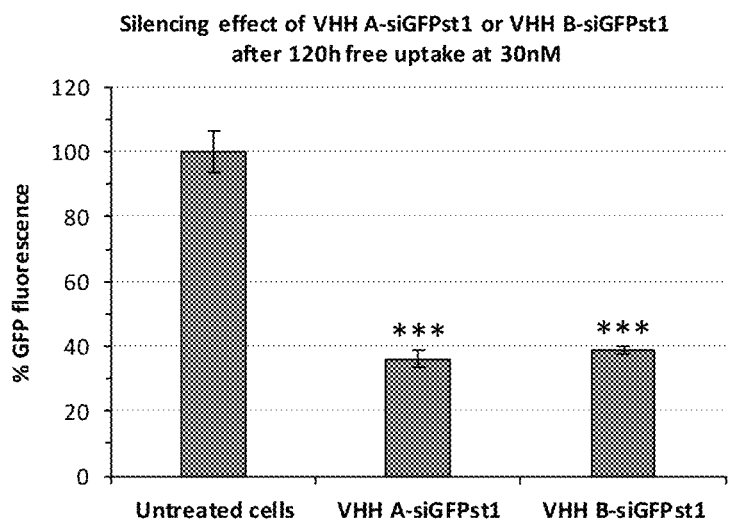
FIGURE 15 (Following)

TRANSFERRIN RECEPTOR-BINDING MOLECULES, CONJUGATES THEREOF AND THEIR USES

CROSS-REFERENCE TO RELATED APPLICATION

This application is the U.S. national stage application of International Patent Application No. PCT/EP2020/050318, filed Jan. 8, 2020.

The Sequence Listing for this application is labeled "Seq-List.txt" which was created on Jun. 22, 2021 and is 74 KB. The entire content of the sequence listing is incorporated herein by reference in its entirety.

The invention relates to Transferrin receptor (TfR)-binding molecules and the uses thereof. The invention particularly relates to Variable Domain of Camelid Heavy Chain-only (VHH) molecules, which bind TfR at the surface of cell membranes such as the blood-brain barrier (BBB), and the uses thereof e.g., to transport molecules of pharmaceutical or diagnostic interest into cells of the central nervous system or TfR-expressing tissues or organs, such as cancers.

BACKGROUND

According to Global Industry Analysts, the global market for drugs treating central nervous system (CNS, brain and spinal cord) pathologies was approximately 100 billion dollars in 2015, with nearly 9 billion dollars of this amount representing products arising from drug delivery technologies (Jain, 2008, *Jain PharmaBiotech Report, Drug Delivery in CNS disorders*). Thus, neurology is today one of the three largest therapeutic areas, along with cardiovascular medicine and oncology. Although the number of people suffering from CNS disorders and pathologies throughout the world is larger than that of people with cardiovascular diseases or cancers, neurology remains an under-developed market. This is explained by the fact that 98% of potential drugs for treating CNS pathologies do not cross the BBB (Pardridge, 2003, *Mol. Interv.*, 3, 90-105).

Indeed, the brain is protected from potentially toxic substances by the presence of two principal physiological barrier systems: the BBB, and the blood-cerebrospinal fluid barrier (BCSFB). The BBB is regarded as the principal route for the uptake of plasma ligands. Its surface area is approximately 5000 times larger than that of the BCSFB. The overall length of the constitutive blood vessels of the BBB is approximately 600 km. Each $cm^3$ of cerebral cortex contains the equivalent of 1 km of blood vessels. The total surface area of the BBB is estimated at 20 $m^2$ (De Boer et al., 2007, *Clin. Pharmacokinet.*, 46(7), 553-576). Thus, the cerebral endothelium, which constitutes the BBB, represents a large surface of potential exchange between the blood and nervous tissue. However, this cerebral endothelium, because of its specific properties, is also a major obstacle to the use of drugs to treat CNS disorders.

Indeed, the BBB is composed of brain capillary endothelial cells (BCECs) that present unique properties, not found in the fenestrated endothelial cells that compose the vascular system of other organs. BCECs form tight junctions, they are surrounded by a basal lamina, astrocyte end-feet, pericytes and microglial and neuronal cells that all together compose a very selective barrier, that controls molecular exchanges between the blood and the brain, that maintains brain homeostasis and that very efficiently protects the brain from toxins and pathogens. The drawback is that the BBB is also impermeable to most molecules, including drugs and imaging agents. As a general rule, only a few small lipophilic molecules of approximately 450 to 600 Daltons can pass through the BBB (only 2% of all drug candidates), and most if not all higher molecular weight molecules, such as therapeutic peptides, proteins, antibodies, which show promising results in in vitro studies and in animal studies for treating CNS disorders, do not pass the BBB.

The BBB is thus regarded as a major obstacle to overcome in the development of novel therapies for treating CNS disorders (Neuwelt et al., 2008, *Lancet Neurol.*, 7, 84-96). One of the research priorities to be associated with the discovery of molecules for treating, diagnosing or imaging CNS pathologies is the development of strategies that will allow/increase the passage of active substances across the BBB.

One approach to avoid the BBB is to administer drugs by direct injection into the CNS (e.g., intraventricular, intracerebral or intrathecal), or to disrupt the BBB. Such highly invasive approaches, however, have drawbacks (such as costs, short effect) and potential risks.

Pharmacological strategies have been contemplated, based on the addition of lipid or lipophilic groups to active substances (transcellular lipophilic diffusion, TLD) or on the use of liposomes (Zhou et al., 1992, *J. Control. Release*, 19, 459-486). However, the addition of lipid or lipophilic groups or the use of liposomes often leads to large and non-specific complexes above the optimal limit of 450 Daltons, which are relatively non effective for crossing the BBB (Levin, 1980, *J. Med. Chem.*, 23, 682-684; Schackert et al., 1989, *Selective Cancer Ther.*, 5, 73-79).

Among the strategies evaluated to deliver protein therapeutics into the brain, hijacking the cellular machinery involved in the transport of natural nutrients and endogenous ligands across the BBB appears as the safest and most effective (Fang et al., 2017; Jones and Shusta, 2007; Pardridge et al., 1992). The transport of macromolecules across the BBB can be facilitated by receptor-mediated transcytosis (RMT), a physiological process involving binding of a ligand to its receptor expressed by BCECs, internalization by endocytosis, intracellular trafficking and dissociation from the receptor in sorting endosomes, followed by its release at the abluminal side of the BBB (Tuma and Hubbard, 2003; Xiao and Gan, 2013). In this regard, WO2010/046588 and WO2011/131896 disclose various peptides with high affinity for LDL receptor, which are capable of transporting drugs or other molecules through the BBB.

Another receptor studied to transport drugs across the BBB is the transferrin receptor (TfR), which is involved in iron transport into the brain by its ligand transferrin (Tf) (Fishman et al., 1987). This receptor was shown to be highly expressed in brain endothelium (Jefferies et al., 1984; Pardridge et al., 1987), albeit it is also abundant in blood cells and lung (Chan and Gerhardt, 1992). Although the use of Tf as a transporter has been studied (Chang et al., 2009; Jain et al., 2011; Yan et al., 2013), the transport mechanism of this molecule is saturable and competes with endogenous Tf. Anti-TfR monoclonal antibodies have been studied as vectors for brain delivery, including the OX26 antibody that targets the rat TfR (Moos and Morgan, 2001; Pardridge et al., 1991; Ulbrich et al., 2009), or the 8D3 (Pardridge, 2015; Zhang and Pardridge, 2005; Zhou et al., 2010) and R17-217 antibodies (Lee et al., 2000; Pardridge, 2015; Ulbrich et al., 2009) that target the mouse TfR (see also WO2012075037, WO2013177062, WO201275037, WO2016077840, WO2016208695). However, drawbacks of these antibodies include their absence of cross-species reactivity, and especially their absence of binding to the human TfR, which precludes preclinical or clinical studies.

Also, the ability of such antibodies to effectively transport drugs across BBB still remains of debate.

Accordingly, despite progress in the field, there is a need in the art for further effective methods and agents capable of improving drug access to the CNS.

SUMMARY OF THE INVENTION

The present invention provides novel binding molecules, which can be used to effectively transport molecules across the BBB. More particularly, the invention discloses VHH molecules that bind both human and non-human TfR and which can deliver drugs to the CNS through transcytosis. The invention demonstrates that VHH molecules of the invention can effectively transmigrate through the CNS and deliver conjugated drugs or imaging agents in vivo. Such VHH thus represent valuable molecules for use in therapeutic or diagnostic approaches.

An object of the invention thus relates to VHH molecules that bind a human and a non-human TfR.

A further object of the invention relates to VHH molecules that bind both a human and a non-human (e.g., rodent, such as murine or rat) TfR with substantially similar affinity.

A further object of the invention is a VHH molecule that binds a human and a non-human TfR and can cross the human blood-brain barrier ("BBB").

Preferred VHH of the invention bind both a human and a murine TfR, can cross the human BBB, and have an affinity for TfR (Kd) below 10 µM, preferably comprised between 0.1 nM and 10 µM.

The invention also relates to chimeric agents (also interchangeably called herein "conjugates") comprising one or more VHH as defined above conjugated to at least one molecule or scaffold. The molecule conjugated to VHH may be e.g., any active compound useful in medicine, such as a drug, virus, diagnostic agent, tracer, etc. The chimeric agent may also contain, in addition to or instead of said active compound, a stabilizing group (e.g., a Fc or IgG for instance) to increase the plasma half-life of the VHH or conjugate. Particular chimeric agents of the invention thus comprise at least one VHH, a stabilizing group, and an active compound, in any order (for example a conjugate VHH-Fc-therapeutic agent).

The invention further provides pharmaceutical or diagnostic compositions comprising a chimeric agent as defined above and, optionally, a suitable excipient.

The invention further provides nucleic acids, vectors, and host cells encoding a VHH or chimeric agent as defined above.

The invention also provides methods for making a VHH or chimeric agent, comprising culturing a host cell as defined above under conditions allowing expression of the nucleic acid.

The invention further provides methods for making a chimeric agent, comprising conjugating one or more VHH as defined above to a molecule or agent or scaffold, covalently or non-covalently.

Another object of the invention relates to a VHH molecule or chimeric agent as defined above for use as a medicament or diagnostic agent.

Another object of the invention relates to the use of a VHH molecule as defined above for increasing the biological activity and/or CNS delivery of a substance of interest.

Another object of the invention relates to a method for improving or enabling passage of a molecule across the BBB, comprising coupling said molecule to a VHH as defined above.

Another object of the invention is a method for treating a pathology in a subject comprising administering to the subject a conjugate as defined above.

Another object of the invention is a method for imaging a particular cell type, target tissue or organ in a subject comprising administering to the subject a conjugate as defined above.

Another object of the invention is an improved method for treating a pathology in a subject with a drug, the improvement consisting in coupling said drug to a VHH molecule as defined above.

The invention can be used in any mammal, in particular any human being.

LEGEND TO THE FIGURES

Figure 1:
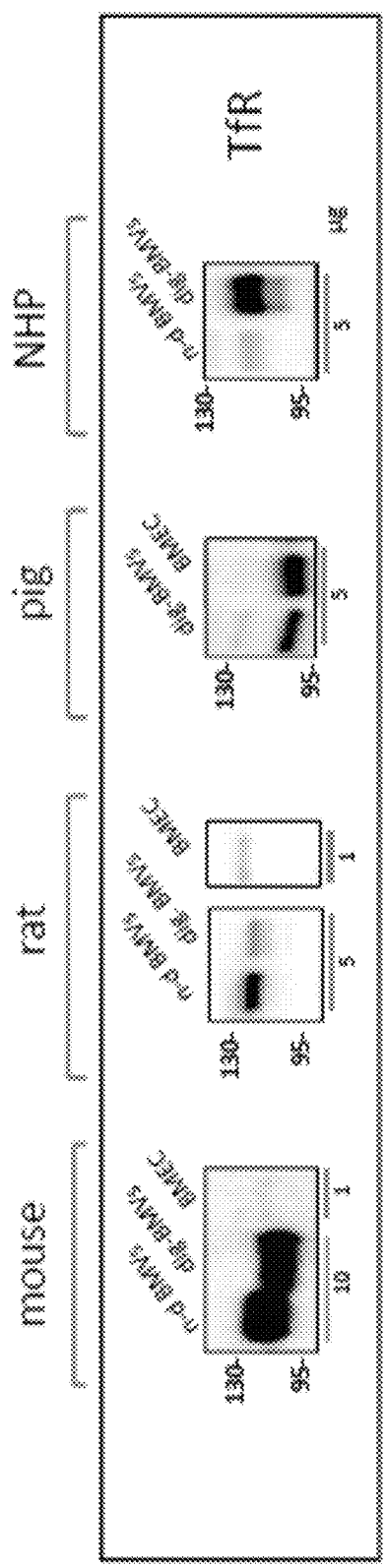

FIG. 1. TfR expression at the BBB. Western blots were performed on the membrane fraction of brain microvessels (BMVs) and brain microvessel endothelial cells (BMEC) from mouse, rat, pig and non-human primate (NHP; rhesus macaque). The amount of protein loaded is indicated under the picture. n-d: non-digested; dig-: digested.

Figure 2:
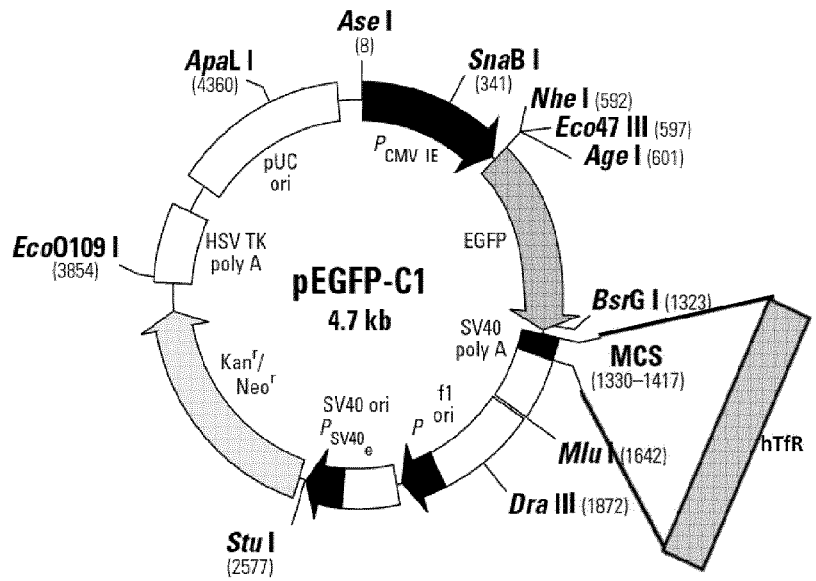
Figure 2:
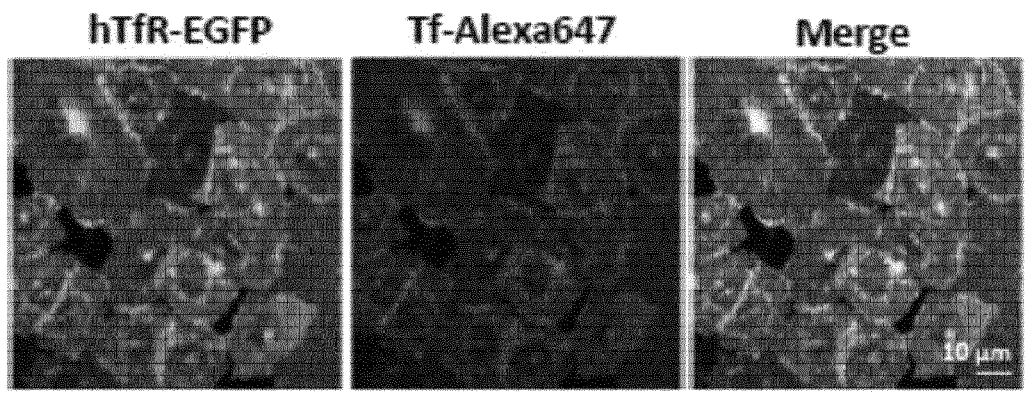
Figure 2:
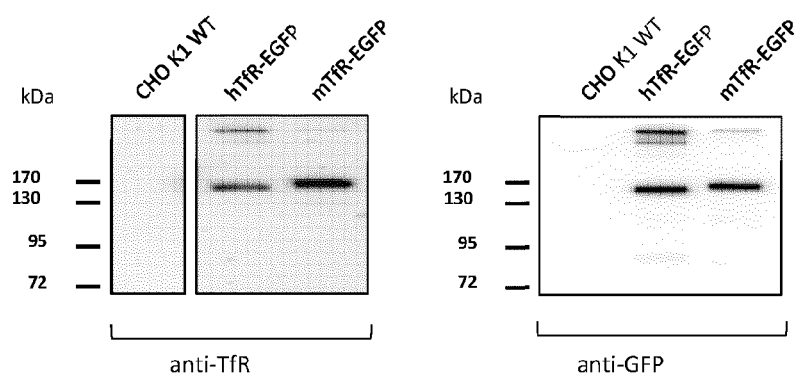

FIG. 2. Validation of CHO cell lines expressing the human or mouse TfR. (A) Map of the plasmid construct used to generate the CHO-hTfR-EGFP cell line. (B) Representative confocal photomicrographs of CHO-hTfR-EGFP cells (green) incubated 1 hr at 37° C. with Tf-Alexa647 (250 µg/ml, red). Cell nuclei were labeled with Hoechst #33342 at 0.5 µg/mL (blue). Co-labeling appears in yellow in the merged picture. (C) Western blots performed on cell membrane preparations of CHO cells expressing hTfR-EGFP and mTfR-EGFP compared to CHO WT, using a rabbit anti-TfR antibody (1/1000) or a mouse anti-GFP antibody (1/1000), followed by HRP-conjugated anti-rabbit or anti-mouse secondary antibodies (1/10000).

Figure 3:
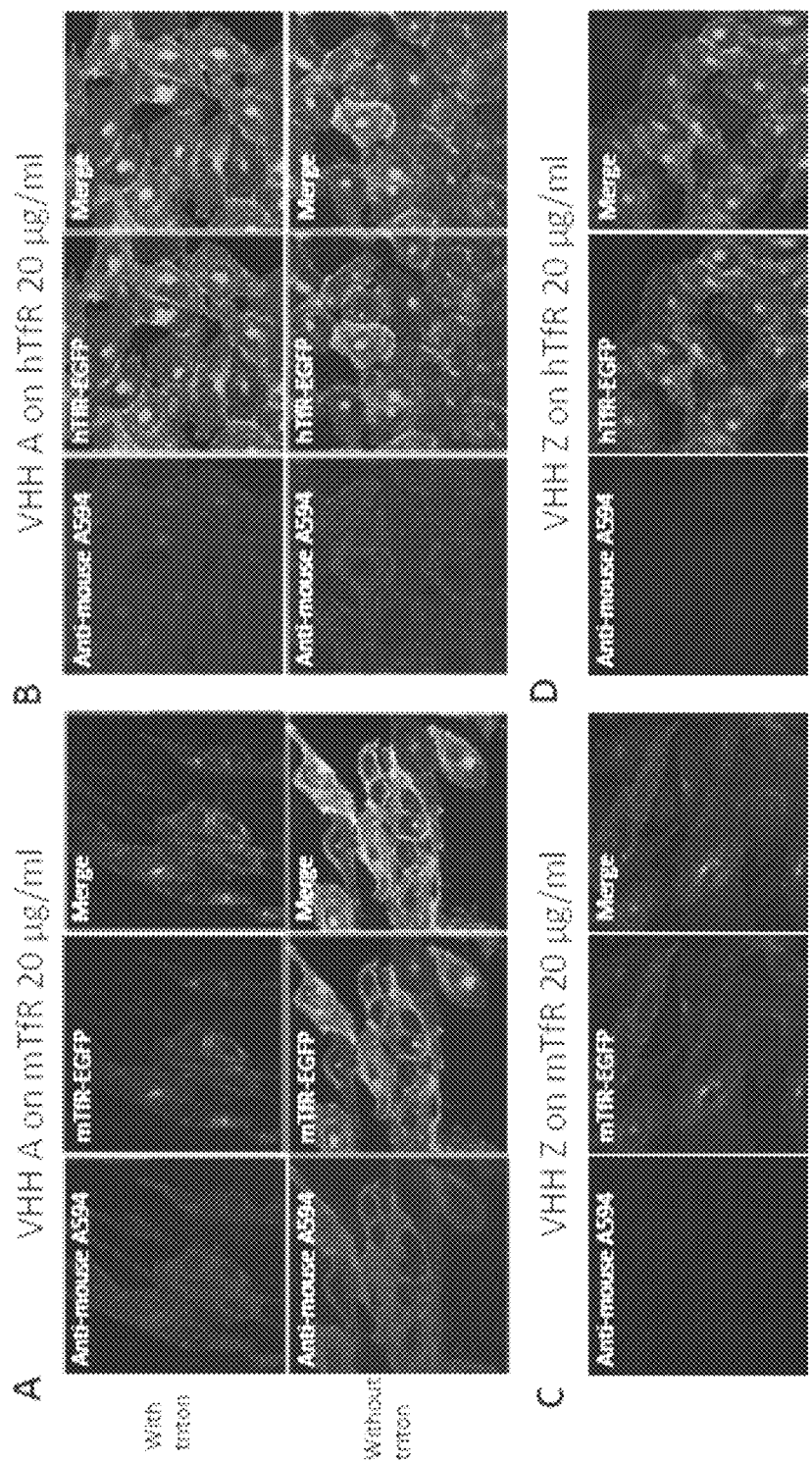

FIG. 3. Cell surface binding and endocytosis of VHH A and VHH Z on CHO cells expressing hTfR and mTfR. Representative confocal photomicrographs of CHO-hTfR-EGFP and CHO-mTfR-EGFP cells (green) incubated 1 hr at 37° C. with VHH A (A, B) and with the control VHH Z (C, D) at 20 µg/ml, detected post-PFA fixation and following or not triton X-100 permeabilization of cell membranes, with a mouse anti-cMyc (1/1000) and an Alexa594-conjugated anti-mouse secondary antibody (1/800, red). Cell nuclei were labeled with Hoechst #33342 at 0.5 µg/ml (blue). Co-labeling appears in yellow/orange in the merged pictures.

Figure 4:
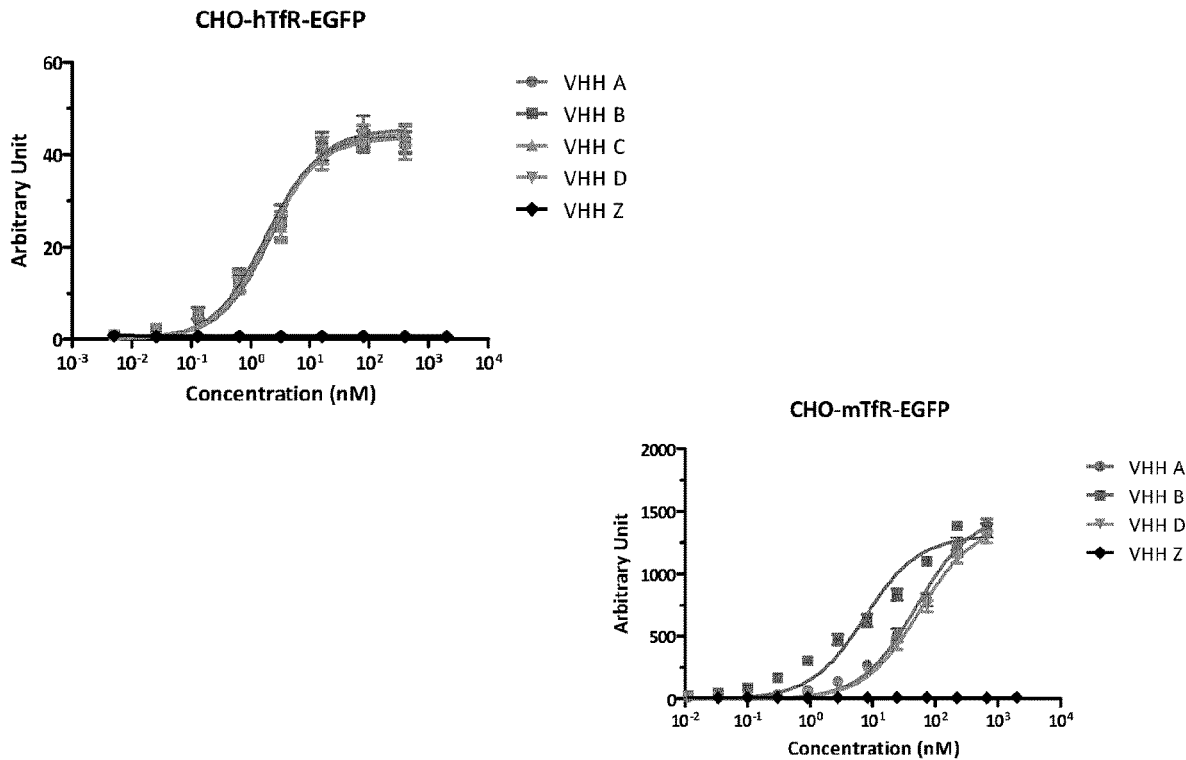

FIG. 4. Apparent $K_d$ determination of VHHs on hTfR- and mTfR-expressing CHO cell lines. (A) CHO-hTfR-EGFP and CHO-mTfR-EGFP cells were incubated 1 hr at 4° C. with various concentrations of VHHs, detected with a mouse anti-6His (1/1000) and an Alexa647-conjugated anti-mouse secondary antibody (1/200 or 1/400). Measurements were performed using flow cytometry. The ratio of fluorescence intensity for each point was normalized with the corresponding EGFP signal (receptor expression) and gave rise to the arbitrary unit. Data are presented as mean±SEM of 3 independent experiments. (B) Characteristics of selected VHHs: Molecular Weight (Da); Theoretical pI; Apparent $K_d$ on human TfR (nM); Apparent $K_d$ on mouse TfR (nM). Data are presented as mean±SEM of 3 independent experiments. NB: no binding.

Figure 5:
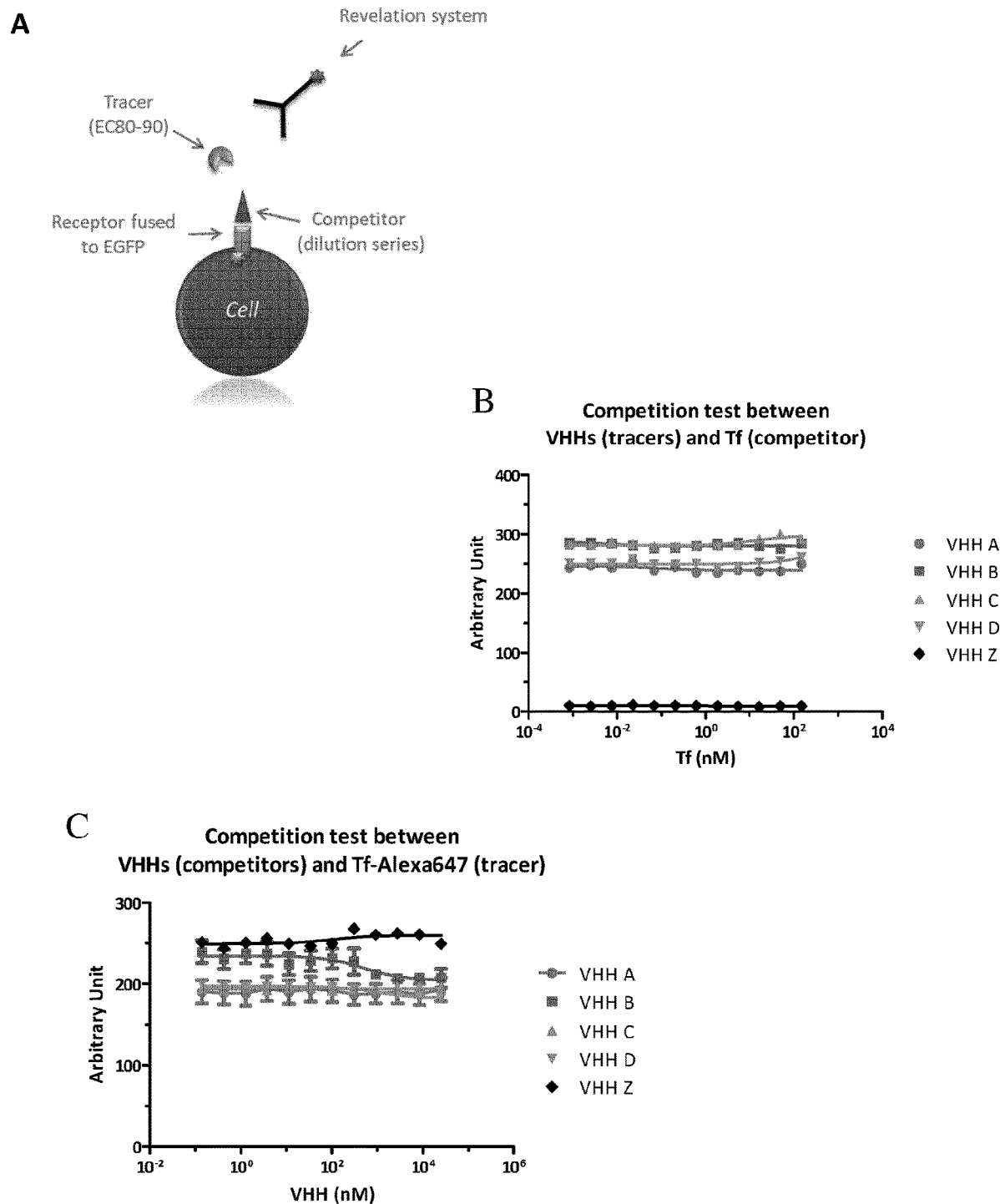

FIG. 5. Competition assays between VHHs and Tf. (A) Principle of competition test. In a first step, CHO-hTfR-EGFP cells were incubated 1 hr at 4° C. with the competitor in dilution series. Second, the tracer at EC90 was added and incubated for 1 hr at 4° C. Tracer was then revealed with the appropriate revelation system. Measurements were performed using flow cytometry. The ratio of fluorescence intensity for each point was normalized with the corresponding EGFP signal (receptor expression) and gave rise to the arbitrary unit. (B) CHO-hTfR-EGFP cells were incubated with the competitor (Tf). Tracers (VHHs) at EC90 were then added and detected with a mouse anti-cMyc antibody (1/50) and an Alexa647-conjugated anti-mouse secondary antibody (1/200). (C) CHO-hTfR-EGFP cells were incubated with competitors (VHHs). Tracer (Tf-Alexa647) at EC90 was then added and detected directly. Data are presented as mean±SEM of 3 independent experiments.

Figure 6:
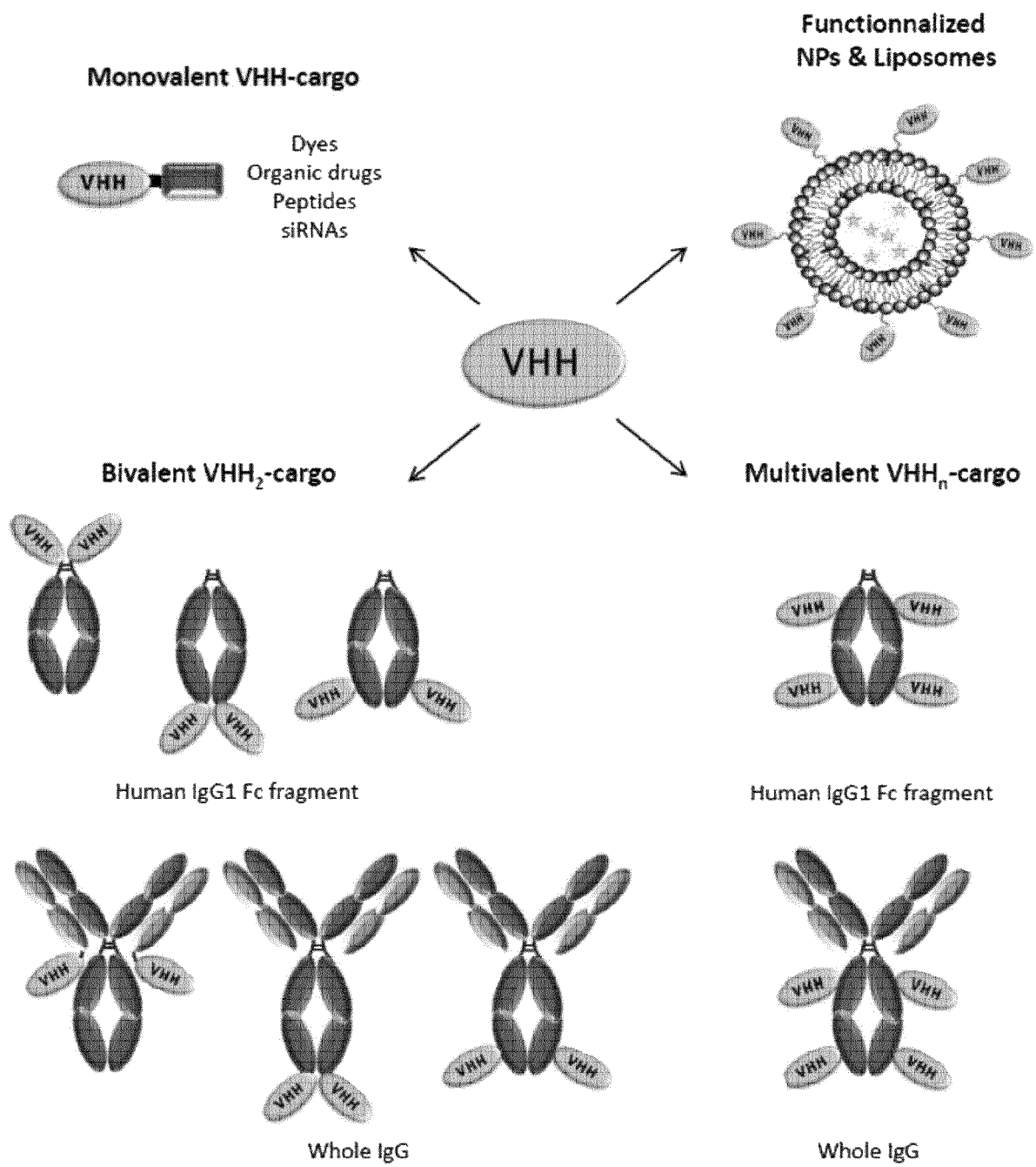

FIG. 6. VHH conjugation strategies. Using either chemical conjugation or recombinant fusion, VHHs can be used to vectorize all kinds of molecules, including non-exhaustively peptides, siRNAs, dyes, nanoparticles (NPs), liposomes, imaging agents and antibodies. Moreover, VHHs can be used to vectorize a molecule as a monovalent (VHH) or multivalent ($VHH_n$) conjugate.

Figure 7:
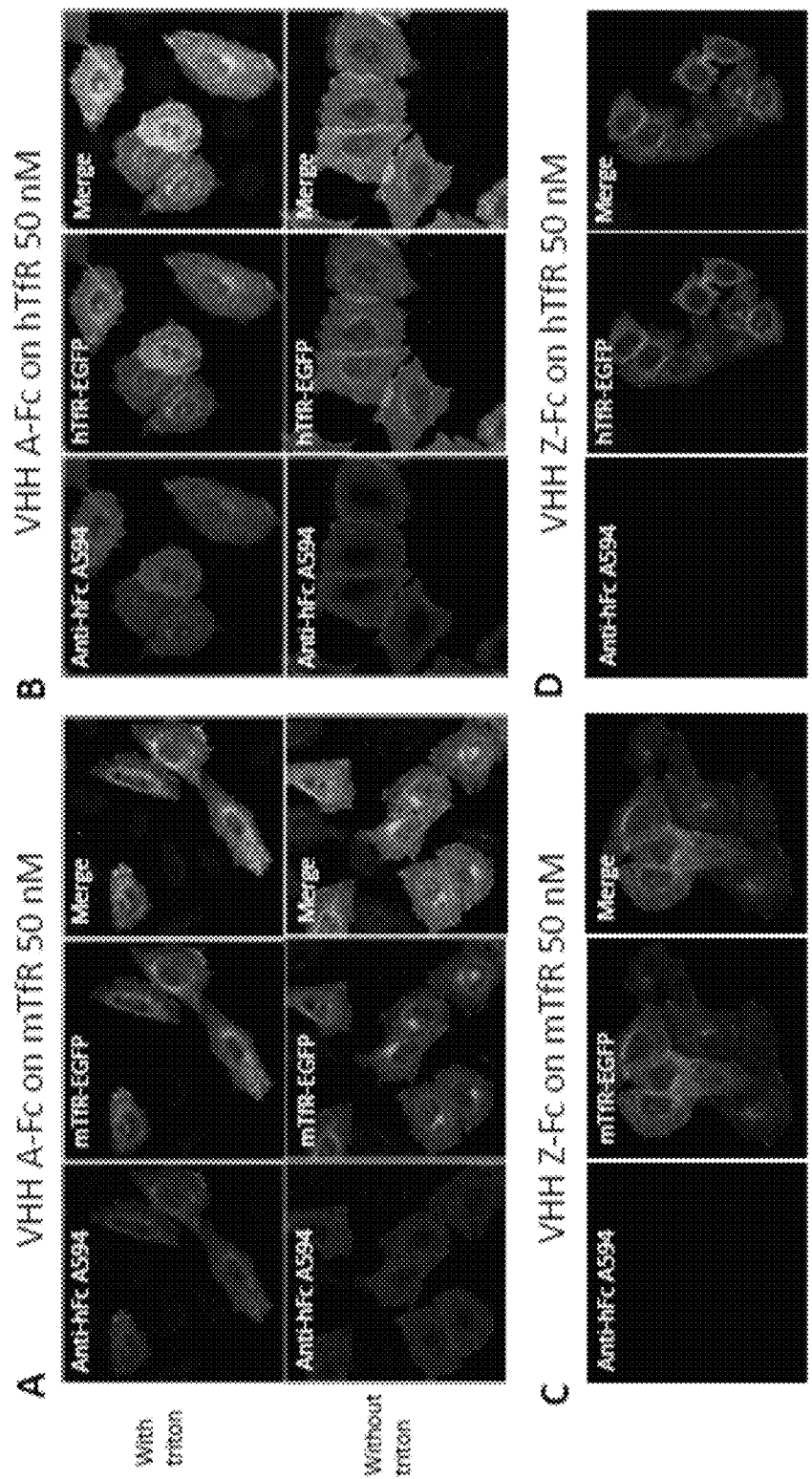

FIG. 7. Cell surface binding and endocytosis of VHH A-Fc and VHH Z-Fc fusion proteins on hTfR- and mTfR-expressing CHO cells. Representative confocal photomicrographs of CHO-hTfR-EGFP and CHO-mTfR-EGFP cells (green) incubated 1 hr at 37° C. with 50 nM of VHH A-Fc (A, B) and with the control VHH Z-Fc (C, D), detected post-PFA fixation and following or not triton X-100 permeabilization of cell membranes, with an Alexa594-conjugated anti-hFc antibody (1/1000, red). Cell nuclei were labeled with Hoechst #33342 at 0.5 µg/ml (blue). Co-labeling appears in yellow/orange in the merged pictures.

Figure 8:
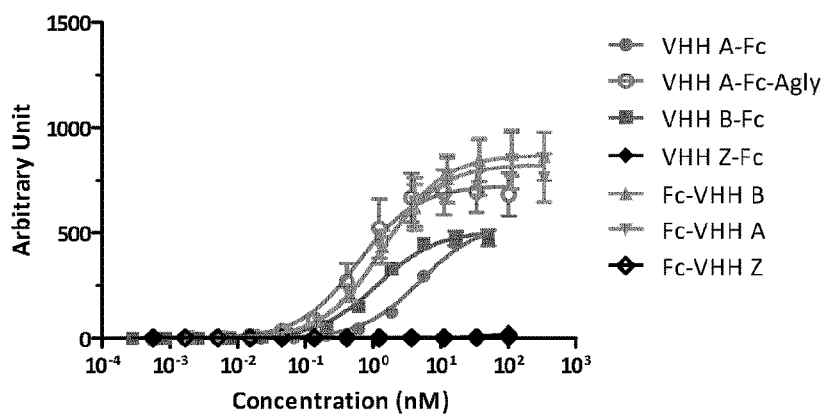
Figure 8:
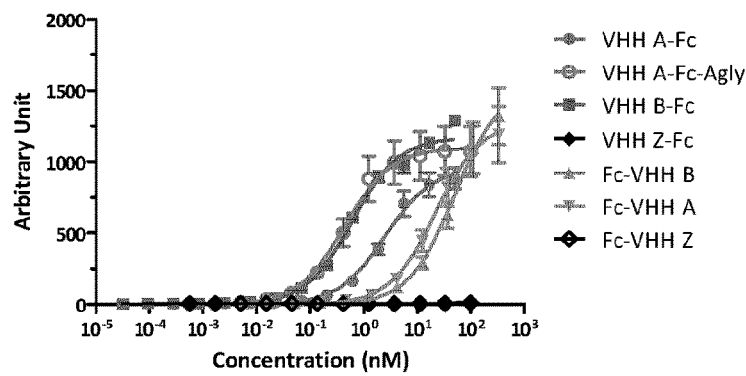

FIG. 8. Apparent $K_d$ determination of VHH-Fcs and Fc-VHHs on hTfR- and mTfR-expressing CHO cell lines. (A) CHO-hTfR-EGFP and CHO-mTfR-EGFP cells were incubated 1 hr at 4° C. with various concentrations of VHH-Fcs or Fc-VHHs, detected with an Alexa647-conjugated anti-hFc antibody (1/400). Measurements were performed using flow cytometry. The ratio of fluorescence intensity for each point was normalized with the corresponding EGFP signal (receptor expression) and gave rise to the arbitrary unit. Data are presented as mean±SEM of 3 independent experiments. (B) Characteristics of selected VHH-Fcs and Fc-VHHs: Molecular Weight (Da); Apparent $K_d$ on human TfR (nM); Apparent $K_d$ on mouse TfR (nM). Data are presented as mean±SEM of 3 independent experiments. NB: no binding for the control VHH (VHH Z).

Figure 9:
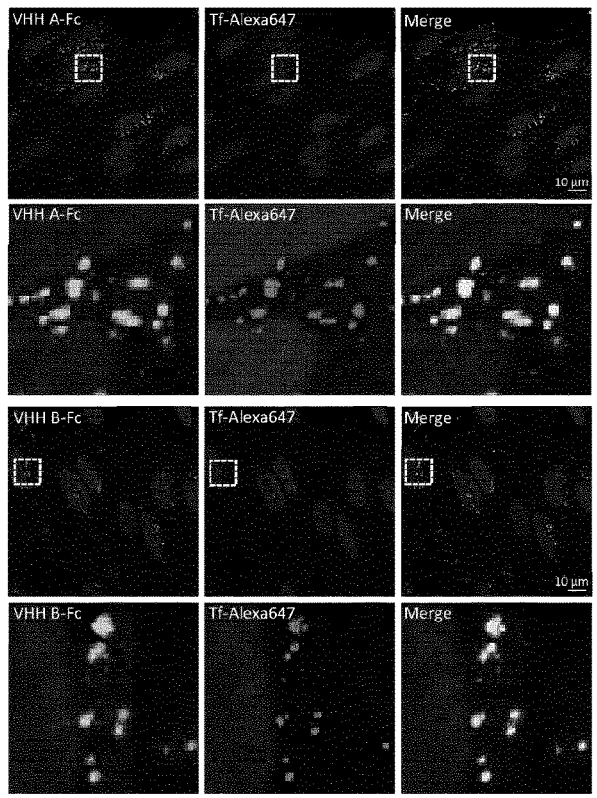
Figure 9:
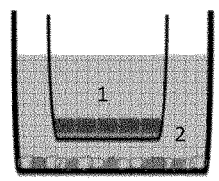
Figure 9:
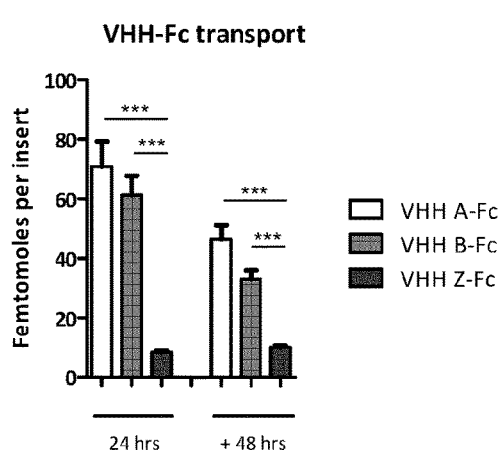
Figure 9:
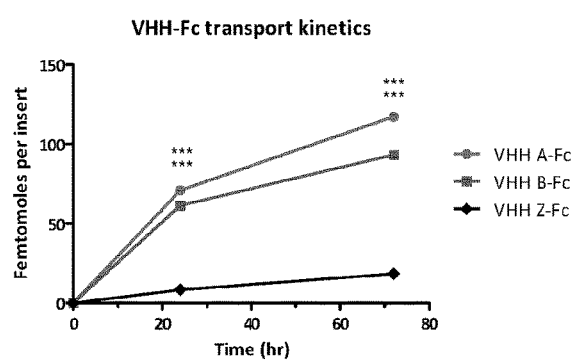

FIG. 9. Uptake and transport of VHH A-Fc and VHH B-Fc fusion proteins in an in vitro BBB model. (A) Representative photomicrographs of rat brain microvascular endothelial cell (rBMEC) monolayers probed for uptake of 500 nM VHH A-Fc and VHH B-Fc, co-incubated with Tf-Alexa647 at 200 nM (red), for 2 hrs on live cells, detected following PFA fixation and triton X-100 permeabilization of cell membranes with an Alexa488-conjugated anti-hFc antibody (1/50, green). Cell nuclei were labeled with Hoechst #33342 at 0.5 µg/ml (blue). Co-labeling appears in yellow in the merged pictures. (B) Schematic representation of the in vitro BBB model, a co-culture system with primary rBMECs plated on collagen type IV/fibronectin-coated filter in the upper compartment (1) and primary astrocytes in the lower compartment (2). (C, D) Transport of VHH A-Fc, VHH B-Fc and VHH Z-Fc fusion proteins across rBMEC monolayers from the luminal (upper) to the abluminal (lower) compartment. (C) VHH A-Fc, VHH B-Fc and VHH Z-Fc were incubated at 10 nM in the luminal compartment for 24 hrs and transport to the abluminal compartment was evaluated (named 24 hrs). Then the inserts containing the VHH-Fc solutions were transferred to another 96-well plate containing fresh transport buffer for another transport interval of 48 hrs (named +48 hrs) to the abluminal compartment. (D) Kinetic presentation of the experiment described in (C) (the 72 hrs transport is the sum of the 24 hrs and 48 hrs transport intervals). The content of Fc fragment in the abluminal compartment was quantified using an in-house anti-Fc ELISA assay. Absorbance units were transformed in femtomoles per insert (surface area of 0.143 $cm^2$ for inserts of a 96-well plate). Three independent experiments of at least 12 inserts were assayed for each conjugate. Data are presented as mean±SEM (*** p≤0.001).

Figure 10:
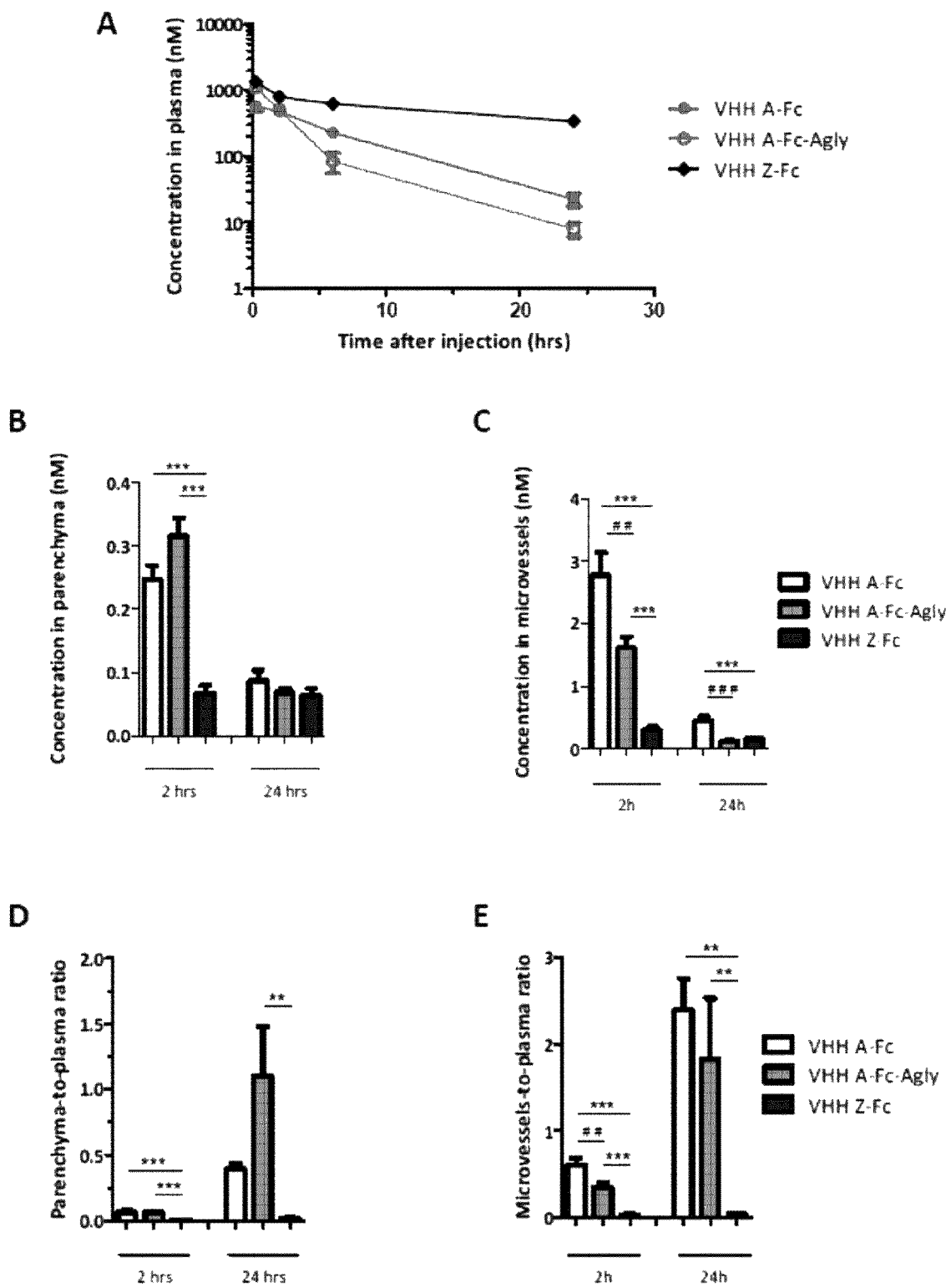

FIG. 10. Distribution of VHH-Fc fusion proteins in WT C57Bl/6 mice at 2 and 24 hrs post-injection (p.i.). VHH A-Fc, VHH A-Fc-Agly and VHH Z-Fc fusions were injected into the tail vein at 5 mg/kg and mice were perfused with saline at either 2 or 24 hrs p.i., after collection of plasmas. Intermediate plasma samples were also collected using retro-orbital sampling at 15 min and 6 hrs p.i. Brains were processed to isolate brain parenchyma from capillary. Amounts of VHH-Fcs in each tissue were assessed using an in-house anti-Fc ELISA assay. Data are presented as mean±SEM of VHH-Fc concentrations in plasma (A), parenchyma (B) and microvessels (C), or by mean±SEM of parenchyma-to-plasma ratio (D), and microvessel-to-plasma ratio (E). (4<n<12 per group per time point; * p≤0.05,  p≤0.01, * p≤0.001).

Figure 11:
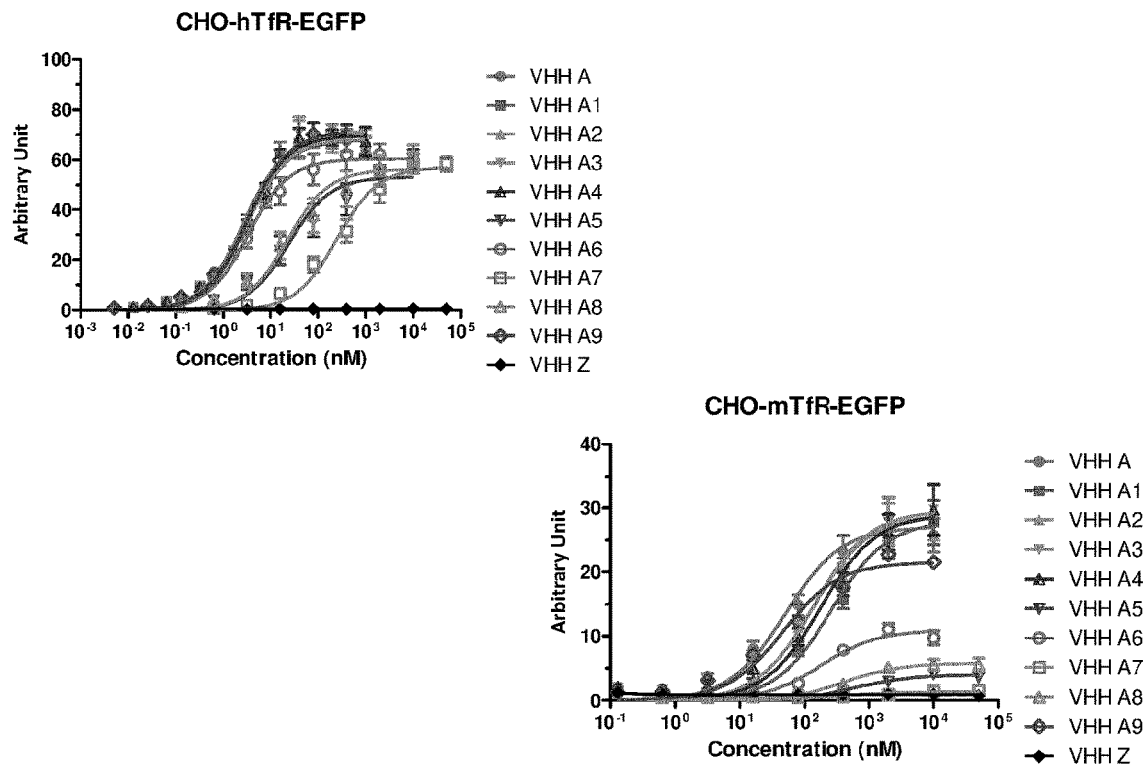

FIG. 11. Apparent $K_d$ determination of VHH A1 to A9 on CHO cell lines stably expressing hTfR and mTfR. (A) CHO-hTfR-EGFP and CHO-mTfR-EGFP cells were incubated 1 hr at 4° C. with various concentrations of VHHs, detected with a mouse anti-6His (1/1000) and an Alexa647-conjugated anti-mouse secondary antibody (1/400). Measurements were performed using flow cytometry. The ratio of fluorescence intensity for each point was normalized with the corresponding EGFP signal (receptor expression) and gave rise to the arbitrary unit. Data are presented as mean±SEM of 3 independent experiments. (B) Characteristics of VHHs: Molecular Weight (Da); Theoretical pI; Apparent $K_d$ on human TfR (nM); Apparent $K_d$ on mouse TfR (nM). Data are presented as mean±SEM of 3 independent experiments. NB: no binding, LB: low binding.

Figure 12:
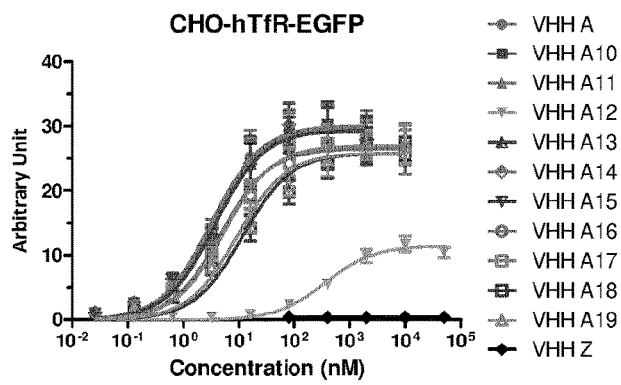
Figure 12:
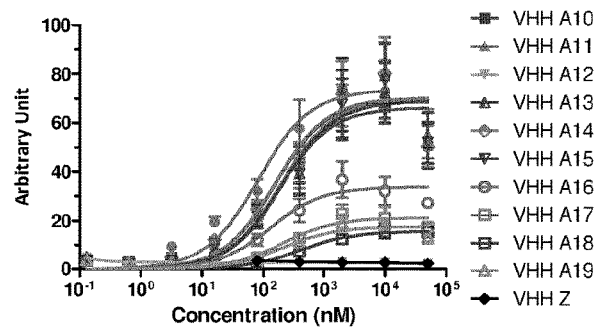

FIG. 12. Apparent $K_d$ determination of VHH A10 to A19 on CHO cell lines stably expressing hTfR and mTfR. (A) CHO-hTfR-EGFP and CHO-mTfR-EGFP cells were incubated 1 hr at 4° C. with various concentrations of VHHs, detected with a mouse anti-6His (1/1000) and an Alexa647-conjugated anti-mouse secondary antibody (1/400). Measurements were performed using flow cytometry. The ratio of fluorescence intensity for each point was normalized with the corresponding EGFP signal (receptor expression) and gave rise to the arbitrary unit. Data are presented as mean±SEM of 3 independent experiments. (B) Characteristics of VHHs: Molecular Weight (Da); Theoretical pI; Apparent $K_d$ on human TfR (nM); Apparent $K_d$ on mouse TfR (nM). Data are presented as mean±SEM of 3 independent experiments. NB: no binding.

Figure 13:
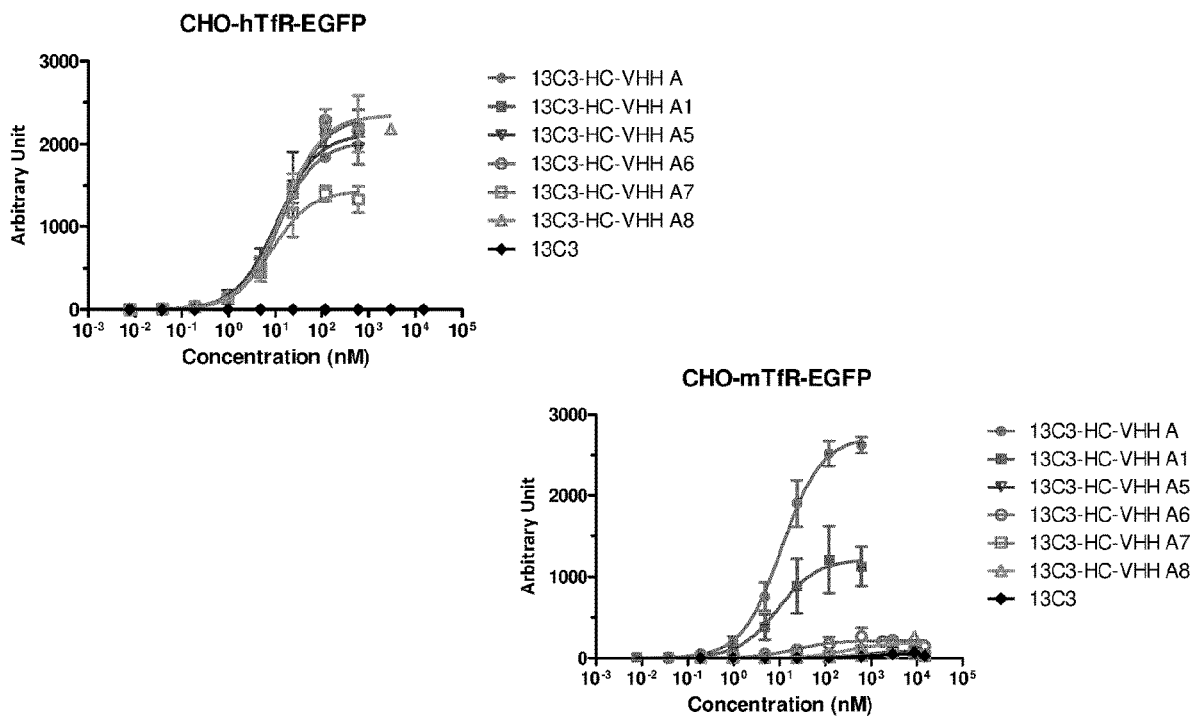

FIG. 13. Apparent $K_d$ determination of 13C3-HC-VHH fusions on hTfR- and mTfR-expressing CHO cell lines. (A) CHO-hTfR-EGFP and CHO-mTfR-EGFP cells were incubated 1 hr at 4° C. with various concentrations of 13C3 fusions and detected with an Alexa647-conjugated anti-mouse antibody (1/400). Measurements were performed using flow cytometry. The ratio of fluorescence intensity for each point was normalized with the corresponding EGFP signal (receptor expression) and gave rise to the arbitrary unit. Data are presented as mean±SEM of 3 independent experiments. (B) Characteristics of 13C3 fusions: Molecular Weight (Da); Apparent $K_d$ on human TfR (nM); Apparent $K_d$ on mouse TfR (nM). Data are presented as mean±SEM of 3 independent experiments. NB: no binding, LB: low binding.

Figure 14:
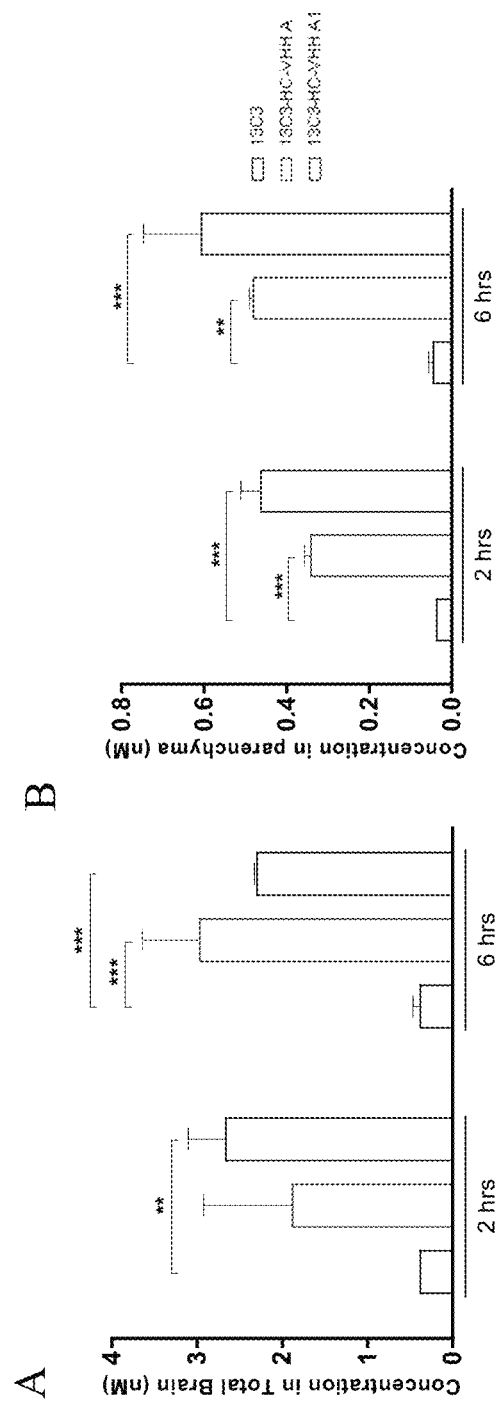

FIG. 14. Distribution of 13C3 monoclonal antibody and 13C3-HC-VHH fusions in WT C57Bl/6 mice at 2 and 6 hrs post-injection (p.i). 13C3, 13C3-HC-VHH A, and 13C3-HC-VHH A1, were injected into the tail vein at 35 nmoles/kg and mice were perfused with saline at either 2 or 6 hrs p.i. Brains were processed to isolate brain parenchyma from capillary. Amounts of 13C3 and 13C3-HC-VHH A/A1 in each tissue/compartment were assessed using a qualified Meso Scale Discovery (MSD) direct coating (Abeta) immunoassay (% CV<20% and recovery±30%). Data are presented as mean±SEM of 13C3 and 13C3-HC-VHH A/A1 concentration in total brain (A) and parenchyma (B) (1<n<4 per group per time point; * p≤0.05,  p≤0.01, * p≤0.001).

FIG. 15. In vitro gene silencing activity of VHH-siGFPst1 bioconjugates. (A) The VHH A-siGFPst1 and VHH B-siGFPst1 bioconjugates bind hTfR. CHO-hTfR-EGFP cells were incubated 1 hr at 4° C. with various concentrations of the indicated compounds. Detection of VHHs was performed using a primary mouse anti-6His (1/1000) and an Alexa647-conjugated anti-mouse secondary antibody (1/400). Measurements of cell-surface signal associated to VHH were performed using flow cytometry. The results are expressed as the ratio of Alexa647-associated fluorescence intensity of test compounds to that of background fluorescence. (B) The VHH A-siGFPst1 bioconjugate displays gene silencing efficiency. CHO-hTfR-EGFP cells were transfected with the indicated compound at 25 nM using Dharmafect 1 (Dharmacon) during 72 h at 37° C. The total fluorescence associated to the EGFP protein was then quantified using flow cytometry and rationalized to that of untreated (control) cells (set at 100%) * p≤0.001. (C) The VHH A-siGFPst1 bioconjugate displays an intrinsic gene silencing activity in the picomolar range upon direct delivery into the cytosol. CHO-hTfR-EGFP cells were transfected with various concentrations of the VHH A-siGFPst1 bioconjugate using Dharmafect 1 (Dharmacon) during 120 hrs at 37° C. The total fluorescence associated with the EGFP protein was then quantified using flow cytometry and rationalized to that of untreated (control) cells (set at 100%). Data were fit using a nonlinear regression using GraphPad Prism® software (solid line) to estimate the IC50 (concentration allowing 50% reduction of GFP protein levels) and the maximum effect (bottom plateau). (D) The VHH A-siGFPst1 bioconjugate triggers specific and efficient TfR-mediated gene silencing. CHO-hTfR-EGFP cells were incubated with the indicated compounds at 1 µM during 120 hrs at 37° C. Data were processed and analyzed as described in (B). * p≤0.001 vs. untreated cells. (E) hTfR-mediated binding and uptake of the VHH A-siGFPst1 bioconjugate allows cytosol delivery and subsequent gene silencing at nanomolar concentrations. CHO-hTfR-EGFP cells were incubated with various concentrations of the VHH A-siGFPst1 bioconjugate during 120 hrs at 37° C. The total fluorescence associated with the EGFP protein was then quantified using flow cytometry and rationalized to that of untreated (control) cells (set at 100%). Data were processed and analyzed as described in (C). (F) The gene silencing effect of the VHH A-siGFPst1 bioconjugate is inhibited by co-incubation with an excess of free TfR-binding VHHs A and B but not with the irrelevant VHH Z. CHO-hTfR-EGFP cells were incubated with VHH A-siGFPst1 at 30 nM alone or in the presence of a 100× excess of the free VHHs A, B or Z during 120 hrs at 37° C. Data were processed and analyzed as described in (C). (G) Cellular exposure to the VHH A-siGFPst1 bioconjugate during a short 6-hour pulse is sufficient to trigger efficient gene silencing. CHO-hTfR-EGFP cells were incubated with various concentrations of the VHH A-siGFPst1 bioconjugate during a short 6-hour pulse followed by chase up to 120 hrs in ligand-free medium. Data were processed and analyzed as described in (B). (H) The gene silencing effect of the VHH B-siGFPst1 bioconjugate was similar to that observed with VHH A-siGFPst1. CHO-hTfR-EGFP cells were incubated with VHH A-siGFPst1 or VHH B-siGFPst1 at 30 nM (saturating concentration based on the IC50 obtained with VHH A-siGFPst1) during 120 hrs at 37° C. Data were processed and analyzed as described in (C).

Figure 16:
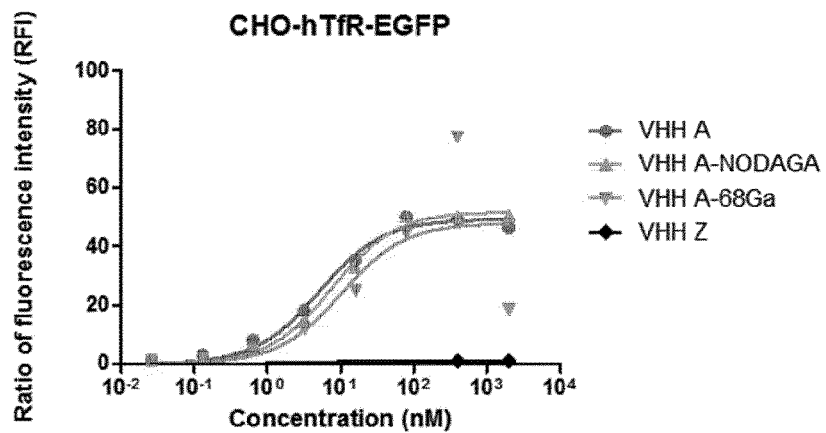
Figure 16:

FIG. 16. PET imaging of VHH A-68Ga bioconjugate in a subcutaneous mouse model of glioblastoma tumor. (A) The VHH A-NODAGA and VHH A-68Ga bioconjugates bind hTfR as efficiently as the non-conjugated VHH A compound. CHO-hTfR-EGFP cells were incubated 1 hr at 4° C. with various concentrations of the indicated compounds. Detection of VHHs was performed using a primary mouse anti-6His (1/1000) and an Alexa647-conjugated anti-mouse secondary antibody (1/400). Measurements of cell-surface signal associated with VHH were performed using flow cytometry. The results are expressed as the ratio of Alexa647-associated fluorescence intensity of test compounds to that of background fluorescence. (B) PET imaging of mice administered with VHH A-68Ga at day 28 after implantation with U87-MG cells (2 hrs post injection). The glioblastoma tumor is indicated by a circle in the sagittal view.

DETAILED DESCRIPTION OF THE INVENTION

The present invention provides novel TfR-binding agents which can be used to transport molecules, such as therapeutic, imaging or diagnostic agents, across the BBB. More particularly, the invention discloses improved VHH molecules which bind TfR, and the uses thereof.

The TfR is involved in the incorporation of iron, transported by its transferrin ligand, and in the regulation of cell growth (Neckers and Trepel 1986, Ponka and Lok 1999). There are two types of transferrin receptors: the TfR1 receptor and a homologous receptor, TfR2, expressed primarily in the liver. In the context of the invention, the term TfR is used to designate the TfR1 homologue.

TfR is a type II homodimeric transmembrane glycoprotein consisting of two identical 90 kDa subunits linked by two disulfide bridges (Jing and Trowbridge 1987, McClelland et al., 1984). Each monomer has a short cytoplasmic N-terminal domain of 61 amino acids containing a YTRF (Tyrosine-Threonine-Arginine-Phenylalanine) internalization motif, a single hydrophobic transmembrane segment of 27 amino acids, and a broad C-terminal extracellular domain of 670 amino acids, containing a trypsin cleavage site and a transferrin binding site (Aisen, 2004). Each subunit is capable of binding a transferrin molecule. The extracellular domain has one O-glycosylation site and three N-glycosylation sites, the latter being particularly important for the proper folding and transport of the receptor to the cell surface (Hayes et al., 1997). There are also palmitylation sites in the intramembranous domain, that presumably anchor the receptor and allow its endocytosis (Alvarez et al., 1990, Omary and Trowbridge, 1981). In addition, an intracellular phosphorylation site is present, whose functions are uncertain, and which plays no role in endocytosis (Rothenberger et al., 1987).

The TfR receptor is expressed at high level by highly proliferating cells, whether healthy or neoplastic (Gatter et al., 1983). Many studies have shown high levels of TfR expression in cancer cells compared to healthy cells. Thus, pathologies such as breast cancer (Yang et al., 2001), gliomas (Prior et al., 1990), pulmonary adenocarcinoma (Kondo et al., 1990), chronic lymphocytic leukemia (Das Gupta and Shah, 1990) or non-Hodgkin's lymphoma (Habeshaw et al., 1983) show increased TfR expression, correlated with tumor grade and stage of disease or prognosis.

Targeting drugs to TfR may thus be suitable for cancer treatment, as well as for crossing the BBB.

Using purified membrane preparations from cells expressing high levels of hTfR and mTfR, we generated and selected VHH molecules that bind both the human and non-human TfR. We showed that when fused to a human IgG1 Fc region or drug (such as an antibody, siRNA) or imaging agent, these VHH molecules retain TfR binding capacity, transmigrate across an in vitro BBB model, and demonstrate brain-targeting properties in vivo. We also showed that when fused to a siRNA or NODAGA scaffold, these VHH molecules retain TfR binding capacity and efficient cell and organ delivery in vivo. The VHH molecules exhibit suitable levels of affinity and specificity to undergo proper endocytosis following TfR binding. The invention thus provides novel TfR-binding molecules which represent valuable agents for drug targeting.

An object of the invention thus relates to VHH molecules, wherein said VHH molecules bind both a human and a non-human (e.g., rodent, such as rat or murine) TfR. Preferably, the VHH can cross the human BBB or bind TfR-expressing tissues such as cancers. The invention also relates to chimeric agents comprising such VHH, their manufacture, compositions comprising the same and the use thereof.

VHH Molecules

VHH molecules correspond to the variable region of heavy chain only camelid antibodies that are naturally devoid of light chains. VHH have a very small size of around 15 kDa. They contain a single chain molecule that can bind its cognate antigen using a single domain. The antigen-binding surfaces of VHHs are usually more convex (or protruding) than those of conventional antibodies, which are usually flat or concave. More specifically, VHHs are composed of 4 Framework Regions (or FRs) whose sequences and structures are defined as conserved, and three Complementarity Determining Regions (or CDRs) showing high variability both in sequence content and structure conformation, which are involved in antigen binding and provide antigen specificity. Compared to conventional human antibody VH, a few amino acids are substituted in the FR2 region and complementarity-determining regions (CDRs) of VHH. For instance, highly conserved hydrophobic amino acids (such as Val47, Gly49, Leu50, and/or Trp52) in FR2 region are often replaced by hydrophilic amino acids (Phe42, Glu49, Arg50, Gly52), rendering the overall structure more hydrophilic and contributing to high stability, solubility and resistance to aggregation.

VHH molecules according to the present invention are polypeptides comprising (or consisting of, or consisting essentially of) an antigen-binding domain of a heavy chain only antibody (HcAb).

In order to generate VHH molecules having suitable properties, the inventors tested over 700 TfR-binding VHH from a library of VHH produced by *lama* immunization with a TfR immunogen. Following analysis of said clones for binding and specificity, the inventors further selected about 100 clones which had the required affinity, specificity and cross species binding. Said clones were all sequenced and their structure was analyzed and compared. Further VHH with controlled/improved binding properties were produced by mutagenesis. The sequences of the relevant domains and preferred VHH are provided in the experimental section and sequence listing. The properties of the VHH and conjugates thereof are also illustrated in the experimental section.

VHH molecules of the invention typically comprise or consist of the formula:

FR1-CDR1-FR2-CDR2-FR3-CDR3-FR4, wherein FRn designates framework regions and CDRn designates complementarity determining regions.

In a particular embodiment, VHH molecules of the invention comprise a CDR1 domain comprising or consisting of an amino acid sequence selected from SEQ ID NOs: 1, 5, 9, 13, 17, 19, 67 or 69, or variants thereof having at least 75% amino acid identity to anyone of said sequences over the entire length thereof, preferably at least 85%, said variants retaining a TfR binding capacity. Preferred VHH molecules of the invention contain a CDR1 domain having an amino acid sequence selected from SEQ ID NOs: 1, 5, 9, 13, 17, 19, 67 or 69, or variants thereof having at most 1 amino acid modification.

The "% identity" between amino acid (or nucleic acid) sequences may be determined by techniques known per se in the art. Typically, the % identity between two nucleic acid or amino acid sequences is determined by means of computer programs such as GAP provided in the GCG program package (Program Manual for the Wisconsin Package, Version 8, August 1996, Genetics Computer Group, 575 Science Drive, Madison, Wisconsin, USA 53711) (Needleman, S. B. and Wunsch, C. D., (1970), Journal of Molecular Biology, 48, 443-453). The % identity between two sequences designates the identity over the entire length of said sequences.

Specific examples of VHH molecules of the invention comprise a CDR1 sequence comprising, or consisting essentially of SEQ ID NO: 1, 5, 9, 13, 17, 19, 67 or 69.

In a further particular embodiment, VHH molecules of the invention comprise a CDR2 domain comprising or consisting of an amino acid sequence selected from SEQ ID NOs: 2, 6, 10, 14, 21, 23, 71, 73 or 75, or variants thereof having at least 70% amino acid identity to anyone of said sequences over the entire length thereof, preferably at least 85%, said variants retaining a TfR binding capacity. Preferred VHH molecules of the invention contain a CDR2 domain having an amino acid sequence selected from SEQ ID NOs: 2, 6, 10, 14, 21, 23, 71, 73 or 75, or variants thereof having at most 1 amino acid modification.

Specific examples of VHH molecules of the invention comprise a CDR2 sequence comprising, or consisting essentially of SEQ ID NO: 2, 6, 10, 14, 21, 23, 71, 73 or 75.

In a further particular embodiment, VHH molecules of the invention comprise a CDR3 domain comprising or consisting of an amino acid sequence selected from SEQ ID NOs: 3, 7, 11, 15, 25, 27, 29, 31, 33, 77, 79, 81, 83, or 85, or variants thereof having at least 60% amino acid identity to anyone of said sequences over the entire length thereof, preferably at least 80%, more preferably at least 85%, said variants retaining a TfR binding capacity. Preferred VHH molecules of the invention contain a CDR3 domain having an amino acid sequence selected from SEQ ID NOs: 3, 7, 11, 15, 25, 27, 29, 31, 33, 77, 79, 81, 83, or 85, or variants thereof having at most 1 amino acid modification.

Specific examples of VHH molecules of the invention comprise a CDR3 sequence comprising, or consisting essentially of SEQ ID NOs: 3, 7, 11, 15, 25, 27, 29, 31, 33, 77, 79, 81, 83, or 85.

In a further particular embodiment, VHH molecules of the invention comprise:
  a CDR1 domain comprising or consisting of an amino acid sequence selected from SEQ ID NOs: 1, 5, 9, 13, 17, 19, 67 or 69, or variants thereof having at least 75% amino acid identity to anyone of said sequences over the entire length thereof, preferably at least 85%, more preferably at least 95%; and
  a CDR2 domain comprising or consisting of an amino acid sequence selected from SEQ ID NOs: 2, 6, 10, 14, 21, 23, 71, 73 or 75, or variants thereof having at least 70% amino acid identity to anyone of said sequences over the entire length thereof, preferably at least 85%, more preferably at least 95%; and
  a CDR3 domain comprising or consisting of an amino acid sequence selected from SEQ ID NOs: 3, 7, 11, 15, 25, 27, 29, 31, 33, 77, 79, 81, 83, or 85, or variants thereof having at least 60% amino acid identity to anyone of said sequences over the entire length thereof, preferably at least 80%, more preferably at least 95%,
said VHH having a TfR-binding capacity.

In a preferred embodiment, the VHH molecules of the invention comprise:
  a CDR1 domain having an amino acid sequence selected from SEQ ID NOs: 1, 5, 9, 13, 17, 19, 67 or 69, or variants thereof having at most 1 amino acid modification; and
  a CDR2 domain having an amino acid sequence selected from SEQ ID NOs: 2, 6, 10, 14, 21, 23, 71, 73 or 75, or variants thereof having at most 1 amino acid modification; and
  a CDR3 domain having an amino acid sequence selected from SEQ ID NOs: 3, 7, 11, 15, 25, 27, 29, 31, 33, 77, 79, 81, 83, or 85, or variants thereof having at most 1 amino acid modification.

In a more preferred embodiment, the VHH molecules of the invention comprise a CDR1, a CDR2 and a CDR3, wherein said CDR1, CDR2 and CDR3 domains comprise or consist of, respectively:
  SEQ ID NOs: 1, 2 and 3; or
  SEQ ID NOs: 17, 2 and 3; or
  SEQ ID NOs: 19, 2 and 3; or
  SEQ ID NOs: 67, 2 and 3; or
  SEQ ID NOs: 69, 2 and 3; or
  SEQ ID NOs: 1, 21 and 3; or
  SEQ ID NOs: 1, 23 and 3; or
  SEQ ID NOs: 1, 71 and 3; or
  SEQ ID NOs: 1, 73 and 3; or
  SEQ ID NOs: 1, 75 and 3; or
  SEQ ID NOs: 1, 2 and 25; or
  SEQ ID NOs: 1, 2 and 27; or
  SEQ ID NOs: 1, 2 and 29; or
  SEQ ID NOs: 1, 2 and 31; or
  SEQ ID NOs: 1, 2 and 33; or
  SEQ ID NOs: 1, 2 and 77; or
  SEQ ID NOs: 1, 2 and 79; or
  SEQ ID NOs: 1, 2 and 81; or
  SEQ ID NOs: 1, 2 and 83; or
  SEQ ID NOs: 1, 2 and 85; or
  SEQ ID NOs: 5, 6 and 7; or
  SEQ ID NOs: 9, 10 and 11; or
  SEQ ID NOs: 13, 14 and 15, or
variants thereof as defined above.

Preferred VHH molecules of the invention comprise FRs domains as defined below.

In a particular embodiment, the FR1 domain comprises or consists of SEQ ID NO: 35 as represented below, or variants thereof having at least 85% amino acid identity to this sequence over the entire length thereof, preferably at least 90%, more preferably at least 95%:

```
                                          (SEQ ID NO: 35)
EVQLVESGGGLVQPGGSLKLSCAAS
```

More preferably, the bold amino acid residues are present and the variability occurs only on the other positions.

In a specific embodiment, the E in position 1 may be replaced with Q.

In a specific embodiment, the V in position 5 may be replaced with Q.

In a specific embodiment, the E in position 6 may be replaced with Q.

In a specific embodiment, the G in position 10 may be replaced with K or A.

In a specific embodiment, the L in position 11 may be replaced with V or E.

In a specific embodiment, the A in position 23 may be replaced with V or T.

More preferably, the FR1 contains at most 4 amino acid modifications by reference to this sequence, even more preferably at most 3, even more preferably at most 2 amino acid modifications in non-bold amino acid residues.

In a further specific embodiment, the FR1 has an amino acid sequence selected from anyone of the amino acid sequences listed below:

```
                                          (SEQ ID NO: 36)
EVQLVESGGGVVQPGGSLKLSCVAS (SEQ ID NO: 37)
EVQLVESGGGVVQPGGSLRLSCAAS (SEQ ID NO: 38)
EVQLVESGGGLVQPGGSLRLSCTAS (SEQ ID NO: 39)
EVQLVESGGGEVQPGGSLKLSCVAS.
```

In a particular embodiment, VHH molecules of the invention comprise a FR2 domain comprising or consisting of SEQ ID NO: 40 as represented below, or variants thereof having at least 85% amino acid identity to this sequence over the entire length thereof, preferably at least 90%, or at least 95%:

```
                                          (SEQ ID NO: 40)
MRWYRQAPGKQRELVAT
```

More preferably, the bold amino acid residues are present and the variability occurs only on the other positions.

In a specific embodiment, the M in position 1 may be replaced with I or V.

In a specific embodiment, the R in position 2 may be replaced with G.

In a specific embodiment, the Y in position 4 may be replaced with F.

In a specific embodiment, the Q in position 6 may be replaced with R.

In a specific embodiment, the A in position 7 may be replaced with R.

In a specific embodiment, the Q in position 11 may be replaced with E.

In a specific embodiment, the L in position 14 may be replaced with F or W.

In a specific embodiment, the T in position 17 may be replaced with G or S.

More preferably, the FR2 contains at most 6 amino acid modifications by reference to this sequence, even more preferably at most 5, at most 3, even more preferably at most 2 amino acid modifications in non-bold amino acid residues.

In a particular embodiment, VHH molecules of the invention comprise at least one of the following amino acids in the FR2 domain: Phe42, Glu49, Arg50 or Gly52.

In a further specific embodiment, the FR2 has an amino acid sequence selected from anyone of the amino acid sequences listed below:

```
                               (SEQ ID NO: 41)
IRWYRQAPGKQREFVAG (SEQ ID NO: 42)
MRWYRQAPGKQREWVAG (SEQ ID NO: 43)
MGWFRRAPGKERELVAS (SEQ ID NO: 44)
VRWYRQRPGKQREWVAG
```

In a particular embodiment, VHH molecules of the invention comprise a FR3 domain comprising or consisting of SEQ ID NO: 45 as represented below, or variants thereof having at least 85% amino acid identity to this sequence over the entire length thereof, preferably at least 90%, more preferably at least 95%:

```
                                      (SEQ ID NO: 45)
YYADSVKGRFTISRDNAKNTVYLQMNSLKPEDTAVYYC
```

More preferably, the bold amino acid residues are present and the variability occurs only on the other positions.

In a specific embodiment, the Y in position 1 may be replaced with N.

In a specific embodiment, the Y in position 2 may be replaced with A.

In a specific embodiment, the A in position 3 may be replaced with P or I.

In a specific embodiment, the D in position 4 may be replaced with S.

More preferably, the FR3 contains at most 7 amino acid modifications by reference to this sequence, even more preferably at most 6, at most 3, even more preferably at most 2 amino acid modifications in non-bold amino acid residues.

In a further specific embodiment, the FR3 has an amino acid sequence selected from anyone of the amino acid sequences listed below:

```
                                       (SEQ ID NO: 46)
NYADSMKGRFTISRDNTKNAVYLQIDSLKPEDTAVYYC (SEQ ID NO: 47)
NYPDSAKGRFTISRDNAKNTVYLQIDSLKPEDTAVYYC (SEQ ID NO: 48)
YAISSVKGRFTISRDNAENTVFLQMNSLKPDDTAVYYC (SEQ ID NO: 49)
NYPDSMKGRFTISRDNAKNTVYLQINSLKSEDTAVYYC
```

In a particular embodiment, VHH molecules of the invention comprise a FR4 domain comprising or consisting of SEQ ID NO: 50 as represented below, or variants thereof having at least 85% amino acid identity to this sequence over the entire length thereof, preferably at least 90%, more preferably at least 95%:

```
                               (SEQ ID NO: 50)
WGQGTQVTVSS
```

More preferably, the bold amino acid residues are present and the variability occurs only on the other positions.

More preferably, the FR4 contains at most 4 amino acid modifications by reference to this sequence, even more preferably at most 3, even more preferably at most 2 amino acid modifications in non-bold amino acid residues.

A specific illustrative example of a FR4 sequence is SEQ ID NO: 50.

Specific examples of TfR-binding VHH molecules of the invention are molecules comprising or consisting of an amino acid sequence selected from anyone of SEQ ID NOs: 4 (VHH A), 8 (VHH B), 12 (VHH C), 16 (VHH D), 18 (VHH A1), 20 (VHH A2), 22 (VHH A3), 24 (VHH A4), 26 (VHH A5), 28 (VHH A6), 30 (VHH A7), 32 (VHH A8), 34 (VHH A9), 68 (VHH A10), 70 (VHH A11), 72 (VHH A12), 74 (VHH A13), 76 (VHH A14), 78 (VHH A15), 80 (VHH A16), 82 (VHH A17), 84 (VHH A18), 86 (VHH A19), 87 (VHH A20), 88 (VHH A21), 89 (VHH A22), 90 (VHH A23), 91 (VHH A24), and 92 (VHH A25) wherein x is 0.

In a particular embodiment, the VHH of the invention are humanized.

For humanization, one or more of the FR and/or CDR domains may be (further) modified by one or more amino acid substitutions.

In this respect, in a particular embodiment, the VHH are humanized by modification (e.g., amino acid substitution) of the FR1 domain. A typical humanized position in FR1 is selected from 19R and 23A, or both (by reference to e.g., anyone of SEQ ID NOs: 35-39 or variants thereof). A specific example of such a humanized FR1 thus comprises SEQ ID NO: 36 wherein K19 and/or V23 are respectively modified into 19R and 23A.

In another particular embodiment, the VHH are humanized by modification of the CDR1 domain. A typical humanized position in CDR1 (by reference to e.g., anyone of SEQ ID NO: 1, 5, 9, 13, 17, 19, 67 or 69 or variants thereof) is 8A.

In another particular embodiment, the VHH are humanized by modification of the FR2 domain. A typical humanized position in FR2 is selected from 1M, 2S or 2H, 4V, 11G, 12L, 14W, or combinations thereof (by reference to e.g., anyone of SEQ ID NOs: 40-44 or variants thereof). A specific example of such a humanized FR2 thus comprises SEQ ID NO: 41 wherein one or more or all of I1, R2, Y4, Q11, R12, and F14 are respectively modified into 1M, 2S or 2H, 4V, 11G, 12L, and 14W.

In another particular embodiment, the VHH are humanized by modification of the CDR2 domain. A typical humanized position in CDR2 (by reference to e.g., anyone of SEQ ID NO: 2, 6, 10, 14, 21, 23, 71, 73, 75 or variants thereof) is 11.

In another particular embodiment, the VHH are humanized by modification of the FR3 domain. A typical humanized position in FR3 is selected from 6V, 17A, 20T, 21L, 25M, 26N, 29R, or combinations thereof (by reference to e.g., anyone of SEQ ID NOs: 45-49 or variants thereof). A specific example of such a humanized FR3 thus comprises SEQ ID NO: 46 wherein one or more or all of M6, T17, A20, V21, I25, D26, and K29, are respectively modified into 6V, 17A, 20T, 21L, 25M, 26N, and 29R.

In another particular embodiment, the VHH are humanized by modification of the CDR3 domain. A typical humanized position in CDR3 (by reference to e.g., anyone of SEQ ID NO: 3, 7, 11, 15, 25, 27, 29, 31, 33, 77, 79, 81, 83, 85 or variants thereof) is 1A or 2R, or both.

In a further particular embodiment, the FR1 and/or FR2 and/or FR3 and/or CDR1 and/or CDR2 and/or CDR3 domains are humanized.

Specific examples of humanized TfR-binding VHH molecules of the invention are molecules comprising or consisting of an amino acid sequence selected from anyone of SEQ ID NOs: 87 (VHH A20), 88 (VHH A21), 89 (VHH A22), 90 (VHH A23), 91 (VHH A24), and 92 (VHH A25), wherein x is 0.

In a further particular embodiment, the VHH molecules may further comprise one or several tags, suitable for e.g., purification, coupling, etc. Examples of such tags include a His tag (e.g., His$_6$), a Q-tag (LQR), or a myc tag (EQKLISEEDL). Typically, the one or several tags are located C-ter of the VHH.

As an illustration, the VHH may comprise, at the C-ter end, the following additional sequence (SEQ ID NO: 51)
AAA<u>EQKLISEEDL</u>NGAA<u>HHHHHH</u>GS, wherein simple underline is a myc tag and double underline is a His tag (the remaining residues being linkers or resulting from cloning).

Specific examples of such tagged TfR-binding VHH molecules of the invention are molecules comprising or consisting of an amino acid sequence selected from anyone of SEQ ID Nos: 4 (VHH A), 8 (VHH B), 12 (VHH C), 16 (VHH D), 18 (VHH A1), 20 (VHH A2), 22 (VHH A3), 24 (VHH A4), 26 (VHH A5), 28 (VHH A6), 30 (VHH A7), 32 (VHH A8), 34 (VHH A9), 68 (VHH A10), 70 (VHH A11), 72 (VHH A12), 74 (VHH A13), 76 (VHH A14), 78 (VHH A15), 80 (VHH A16), 82 (VHH A17), 84 (VHH A18), 86 (VHH A19), 87 (VHH A20), 88 (VHH A21), 89 (VHH A22), 90 (VHH A23), 91 (VHH A24), and 92 (VHH A25), wherein x is 1.

As another illustration, the VHH of the invention may comprise a Q-tag of sequence LQR, preferably located C-ter of the VHH.

As a further illustration, the VHH of the invention may comprise a Gly linker, preferably located C-ter of the VHH. The Gly linker may comprise a Gly repeat of e.g., 2-7 Gly residues, such as 3 to 6. Specific examples of Gly linkers include Gly3, Gly4, Gly5 or SerGlySerGly5.

In a particular embodiment, VHH of the invention may comprise a Gly linker and a Q-tag, preferably located C-terminally. More specific examples of such VHH comprise the following structure: VHH-GlyLinker-Qtag, wherein the GlyLinker comprises 2-6 Gly residues and the Q tag contains or consists of LQR.

As an illustration, the VHH may comprise, at the C-ter end, the following additional sequence GGG<u>LQR</u> wherein underline is the Q-tag and bold is a Gly linker.

In a further particular embodiment, VHH of the invention may comprise an Ala linker, a His tag, a Gly linker and a Q-tag. Preferably, the linkers and tags are located C-terminally of the VHH. In other embodiments, the Qtag at least may be located N-ter of the VHH. More specific examples of such VHH comprise the following structure: VHH-AlaLinker-HisTag-GlyLinker-Qtag, wherein the AlaLinker comprises 3 residues, the HisTag comprises 2-7 His residues, the GlyLinker comprises 2-6 Gly residues and the Q tag contains or consists of LQR.

As an illustration, the VHH may comprise, at the C-ter end, the following additional sequence AAA<u>HHHHHH</u>GGGL<u>QR</u> wherein underline is the Q-tag, bold are an Ala and a Gly linker, double underline is a His tag.

Further specific examples of TfR-binding VHH molecules of the invention are VHH molecules which competitively inhibit binding of a VHH as defined above to a human and a non-human TfR. The term "competitively inhibits" indicates that the VHH can reduce or inhibit or displace the binding of a said reference VHH to TfR, in vitro or in vivo. Competition assays can be performed using standard techniques such as, for instance, competitive ELISA or other binding assays. Typically, a competitive binding assay involves a recombinant cell or membrane preparation expressing a TfR, optionally bound to a solid substrate, an unlabeled test VHH (or a phage expressing the same) and a labeled reference VHH (or a phage expressing the same). Competitive inhibition is measured by determining the amount of labeled VHH bound in the presence of the test VHH. Usually the test VHH is present in excess, such as about 5 to 500 times the amount of reference VHH. Typically, for ELISA, the test VHH is in 100-fold excess. When a test VHH present in excess inhibits or displaces at least 70% of the binding of the reference VHH to TfR, it is considered as competitively inhibiting said reference VHH. Preferred competing VHH bind epitopes that share common amino acid residues.

As shown in the experimental section, VHH molecules are able to bind TfR in vitro and in vivo. They show adequate affinity, with an apparent Kd comprised between 0.1 nM and 10 μM, particularly between 1 μM and 1 nM. Furthermore, all of these molecules bind both human and murine TfR. Moreover, binding of said VHH of the invention to a human TfR receptor does not compete with binding of transferrin, the endogenous TfR ligand, and thus does not affect regular functions of said ligand. Conjugates produced with such VHH molecules have further been shown to bind TfR in vitro and to be transported across the BBB into the CNS in vivo, showing transcytosis. Such VHH thus represent potent agents for drug delivery or targeting.

The VHH of the invention can be synthesized by any technique known to those skilled in the art (chemical, biological or genetic synthesis, etc.). They can be preserved as-is, or be formulated in the presence of a substance of interest or any acceptable excipient.

For chemical syntheses, commercial apparatuses that can incorporate natural as well as non-natural amino acids, such as D enantiomers and residues with side chains with hydrophobicities and steric obstructions different from those of their natural homologues (so-called exotic, i.e., non-coded, amino acids), or a VHH sequence containing one or more peptidomimetic bonds that can include notably intercalation of a methylene (—CH$_2$—) or phosphate (—PO$_2$—) group, a secondary amine (—NH—) or an oxygen (—O—) or an N-alkylpeptide, are used.

During synthesis, it is possible to introduce various chemical modifications, such as for example, putting in the N-term or C-term position or on a side chain a lipid (or phospholipid) derivative or a constituent of a liposome or a nanoparticle, in order to be able to incorporate the VHH of the invention within a lipid membrane such as that of a liposome composed of one or more lipid layers or bilayers, or of a nanoparticle.

The VHH of the invention can also be obtained from a nucleic acid sequence coding for the same, as described further below.

Conjugates

A further object of the invention relates to conjugates (also interchangeably called herein "chimeric agents") comprising one or more VHH molecules as defined above, conjugated to at least one molecule or scaffold of interest.

The molecule of interest may be any molecule such as a medicament or drug, a diagnostic agent, an imaging molecule, a tracer, etc. Examples of conjugated molecules of interest include, without limitation, any chemical entity such as small chemical molecules (such as an antibiotic, antiviral, immunomodulator, antineoplastic, anti-inflammatory, adjuvant, etc.); peptides, polypeptides and proteins (such as an enzyme, hormone, neurotrophic factor, neuropeptide, cytokine, apolipoprotein, growth factor, antigen, antibody or part of an antibody, adjuvant, etc.); nucleic acids (such as RNA or DNA of human, viral, animal, eukaryotic or prokaryotic, plant or synthetic origin, etc., including e.g., coding genes, inhibitory nucleic acids such as ribozymes, antisense, interfering nucleic acids, full genomes or portions thereof, plasmids, etc); lipids, viruses, markers, or tracers, for instance. Generally, the "molecule of interest" can be any drug active ingredient, whether a chemical, biochemical, natural or synthetic compound. Generally, the expression "small chemical molecule" designates a molecule of pharmaceutical interest with a maximum molecular weight of 1000 Daltons, typically between 300 Daltons and 700 Daltons.

The conjugated compound is typically a medicament (such as a small drug, nucleic acid or polypeptide, e.g., an antibody or fragment thereof) or imaging agent suitable for treating or detecting neurological, infectious or cancerous pathologies, preferably of the CNS, such as the brain.

The chimeric agent may also contain, in addition to or instead of said compound of interest, a stabilizing group to increase the plasma half-life of the VHH or conjugate. Particular chimeric agents of the invention thus comprise at least one VHH, a stabilizing group, and an active compound, in any order.

The stabilizing group may be any group known to have substantial plasma half-life (e.g. at least 1 hour) and essentially no adverse biological activity Examples of such stabilizing group include, for instance, a Fc fragment of an immunoglobulin or variants thereof, large human serum proteins such as albumin, HSA, or IgGs or PEGs molecules. In a particular embodiment, the stabilizing group is a Fc fragment of a human IgG1. More preferably, the stabilizing group is an aglycosylated Fc fragment of an IgG1.

The VHH may be conjugated N-ter or C-ter of the stabilizing group, or both. When the stabilizing group is a Fc fragment, conjugation is typically by genetic fusion. The resulting protein may remain as a monomeric agent, or multimerize, depending on the nature of the stabilizing group. In the case of a Fc fragment, the fusion protein Fc-VHH or VHH-Fc usually forms homodimers.

In the conjugate compounds of the invention, coupling can be performed by any acceptable means of bonding taking into account the chemical nature, obstruction and number of conjugated entities. Coupling can thus be carried out by one or more covalent, ionic, hydrogen, hydrophobic or Van der Waals bonds, cleavable or non-cleavable in physiological medium or within cells. Furthermore, coupling can be made at various reactive groups, and notably at one or more terminal ends and/or at one or more internal or lateral reactive groups. Coupling can also be carried out using genetic engineering.

It is preferable that the interaction is sufficiently strong so that the VHH is not dissociated from the active substance before having reached its site of action. For this reason, the preferred coupling of the invention is covalent coupling, although non-covalent coupling may also be employed. The compound of interest can be coupled with the VHH either at one of the terminal ends (N-term or C-term), or at a side chain of one of the constitutive amino acids of the sequence (Majumdar and Siahaan, *Med Res Rev.*, Epub ahead of print). The compound of interest can be coupled directly to a VHH, or indirectly by means of a linker or spacer. Means of covalent chemical coupling, calling upon a spacer or not, include for instance those selected from bi- or multifunctional agents containing alkyl, aryl or peptide groups by esters, aldehydes or alkyl or aryl acids, anhydride, sulfhydryl or carboxyl groups, groups derived from cyanogen bromide or chloride, carbonyldiimidazole, succinimide esters or sulfonic halides.

Illustrative strategies for conjugating a VHH of the invention to a molecule or scaffold are disclosed in FIG. 6.

In a particular embodiment, coupling (or conjugation) is by genetic fusion. Such strategy can be used when the coupled molecule is a peptide or polypeptide. In such a case, a nucleic acid molecule encoding the VHH fused to the molecule is prepared and expressed in any suitable expression system, to produce the conjugate.

In another particular embodiment, coupling (or conjugation) is by enzymatic reaction. In particular, site-specific conjugation onto the VHH can be performed using the transglutaminase enzyme (TGase). TGase catalyzes the formation of a stable isopeptidic bond between (i) the side chain of a glutamine residue inserted in a tag sequence specifically recognized by the TGase (namely a Q-tag) and (ii) an amino-functionalized donor substrate. In this regard, the inventors have developed a particular tag sequence (named "Q-tag") which is recognized by TGase and may be used to couple VHH of the invention to any molecule of interest, particularly chemical drugs or agents. For this purpose, VHHs are prepared by genetic fusion to add in tandem (typically to their C-terminus) the following tags: first an optional trialanine linker, then an optional His-tag, then an optional small triglycine linker, and finally a Q-tag. The triglycine linker allows to space out the Q-tag to allow a better accessibility of the TGase to the glutamine while the His-tag aims at facilitating the purification of the VHH and its further functionalized versions.

The general conjugation strategy that was developed is a convergent synthesis that is based on a process comprising:

1) introduction onto the glutamine of the Q-tag of the VHH a reactive moiety for further conjugation to a molecule of interest. In this objective, a heterobifunctional linker having two different reactive ends is allowed to be processed by the TGase: one suitable primary amine-group toward the TGase and one orthogonal reactive moiety. Representative examples of such orthogonal and reactive groups include azides, constraints alkynes such as DBCO (dibenzocyclooctyne) or BCN (bicyclo[6.1.0]nonyne), tetrazines, TCO (trans-cyclooctene), free or protected thiols, etc.
2) introduction onto the molecule of interest of a reactive moiety complementary to the one incorporated onto the VHH Q-tag. Representative examples of such orthogonal and reactive groups include azides, constrained alkynes such as DBCO or BCN, tetrazines, TCO, free or protected thiols, etc.
3) conjugation of both the functionalized VHH and molecule owing to their complementary reactive groups.

Such conjugation strategy represents a further object of the present invention. In particular, an object of the invention resides in a method for coupling two molecules using a Q-tag as defined above through TGase coupling reaction. A further object of the invention is a VHH comprising a Q-tag. A further object of the invention is a VHH molecule comprising a linker, such as a Gly linker, and a Q-tag. Preferred VHH of the invention have the following structure:

VHH-Linker-His$_m$-Linker-LQR, wherein:
VHH is any VHH molecule;
Linker is any molecular linker such as an Ala or Gly linker (preferably the two linkers are different); and
m is an integer from 0 to 6.

In a particular embodiment, the invention relates to a conjugate comprising a VHH covalently linked to a chemical entity. Preferred variants of such conjugates contain 1 VHH and 1 chemical entity.

In another particular embodiment, the invention relates to a conjugate comprising a VHH covalently linked to a nucleic acid. The nucleic acid may be an antisense oligo, a ribozyme, an aptamer, a siRNA, etc. Preferred variants of such conjugates contain 1 VHH and 1 nucleic acid molecule.

In another particular embodiment, the invention relates to a conjugate comprising a VHH covalently linked to a peptide. The peptide may be an active molecule, a bait, a tag, a ligand, etc. Preferred variants of such conjugates contain 1 VHH and 1 peptide.

In another embodiment, the invention relates to a conjugate comprising a VHH covalently linked to a dye.

In another embodiment, the invention relates to a conjugate comprising a VHH covalently linked to a nanoparticle or liposome. The nanoparticle or liposome may be loaded or functionalized with active agents. Preferred variants of such conjugates contain several VHH molecules coupled to each nanoparticle or liposome.

In a further embodiment, the conjugate comprises an antibody or a fragment thereof to which one or several VHH molecules are coupled. Typically, a VHH molecule is coupled to a C- or N-ter of a heavy or light chain, or both, or to the C- or N-ter of an Fc fragment.

The invention also relates to a method for preparing a conjugate compound such as defined above, characterized in that it comprises a step of coupling between a VHH and a molecule or scaffold, preferably by a chemical, biochemical or enzymatic pathway, or by genetic engineering.

In a chimeric agent of the invention, when several VHH are present, they may have a similar or different binding specificity.

Nucleic Acids, Vectors and Host Cells

A further aspect of the invention relates to a nucleic acid encoding a VHH as defined above, or a conjugate thereof (when the conjugated moiety is an amino acid sequence). The nucleic acid may be single- or double-stranded. The nucleic acid can be DNA (cDNA or gDNA), RNA, or a mixture thereof. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and/or mutagenesis. The nucleic acid according to the invention may be deduced from the amino acid sequence of the VHH molecules according to the invention and codon usage may be adapted according to the host cell in which the nucleic acid shall be transcribed. These steps may be carried out according to methods well known to one of skill in the art and some of which are described in the reference manual Sambrook et al. (Sambrook J, Russell D (2001) Molecular cloning: a laboratory manual, Third Edition Cold Spring Harbor).

Specific examples of such nucleic acid sequences include the sequences comprising anyone of SEQ ID NOs: 52-64 and 95-110, and the complementary sequence thereto, as well as fragments thereof devoid of the optional tag-coding portion. The domains encoding CDR1, CDR2 and CDR3 are underlined. The tag-coding portion is in bold.

The invention also relates to a vector containing such a nucleic acid, optionally under control of regulatory sequences (e.g., promoter, terminator, etc). The vector may be a plasmid, virus, cosmid, phagemid, artificial chromosome, etc. In particular, the vector may comprise a nucleic acid of the invention operably linked to a regulatory region, i.e. a region comprising one or more control sequences. Optionally, the vector may comprise several nucleic acids of the invention operably linked to several regulatory regions.

The term "control sequences" means nucleic acid sequences necessary for expression of a coding region. Control sequences may be endogenous or heterologous. Well-known control sequences and currently used by the person skilled in the art will be preferred. Such control sequences include, but are not limited to, promoter, signal-peptide sequence and transcription terminator.

The term "operably linked" means a configuration in which a control sequence is placed at an appropriate position relative to a coding sequence, in such a way that the control sequence directs expression of the coding region.

The present invention further relates to the use of a nucleic acid or vector according to the invention to transform, transfect or transduce a host cell.

The present invention also provides a host cell comprising one or several nucleic acids of the invention and/or one or several vectors of the invention.

The term "host cell" also encompasses any progeny of a parent host cell that is not identical to the parent host cell due to mutations that occur during replication. Suitable host cells may be prokaryotic (e.g., a bacterium) or eukaryotic (e.g., yeast, plant, insect or mammalian cell). Specific illustrative examples of such cells include *E. coli* strains, CHO cells, *Saccharomyces* strains, plant cells, sf9 insect cells etc.

Uses

VHH molecules of the invention can bind to TfR and thus target/deliver molecules to TfR-expressing cells or organs.

Within the context of this invention, binding is preferably specific, so that binding to TfR occurs with higher affinity than binding to any other antigen in the same species. Preferred VHH molecules of the invention bind human TfR1 and a murine or rat TfR. More preferably, the VHH molecules bind the human and murine receptors with a substantially similar affinity.

The invention thus relates to methods of targeting/delivering a compound to/through a TfR-expressing cell or organ, comprising coupling said compound to at least one VHH of the invention.

The invention further relates to the use of a VHH such as defined above, as a vector for the transport of a compound to/through a TfR-expressing cell or organ.

The invention also relates to the use of a VHH such as defined above for preparing a drug capable of crossing the BBB.

The invention also relates to a method for enabling or improving the passage of a molecule across the BBB, comprising the coupling of the molecule to a VHH of the invention.

The VHH of the invention may be used to transport or deliver any compound, such as small drugs, proteins, polypeptides, peptides, amino acids, lipids, nucleic acids, viruses, liposomes, etc.

The invention also relates to a pharmaceutical composition characterized in that it comprises at least one VHH or VHH-drug conjugate such as defined above and one or more pharmaceutically acceptable excipients.

The invention also relates to a diagnostic composition characterized in that it comprises a VHH or VHH-diagnostic or medical imaging agent conjugate compound such as defined above.

The conjugate can be used in the form of any pharmaceutically acceptable salt. The expression "pharmaceutically acceptable salts" refers to, for example and in a non-restrictive way, pharmaceutically acceptable base or acid addition salts, hydrates, esters, solvates, precursors, metabolites or stereoisomers, said vectors or conjugates loaded with at least one substance of interest.

The expression "pharmaceutically acceptable salts" refers to nontoxic salts, which can be generally prepared by reacting a free base with a suitable organic or inorganic acid. These salts preserve the biological effectiveness and the properties of free bases. Representative examples of such salts include water-soluble and water-insoluble salts such as acetates, N-methylglucamine ammonium, amsonates (4,4-diaminostilbene-2,2'-disulphonates), benzenesulphonates, benzonates, bicarbonates, bisulphates, bitartrates, borates, hydrobromides, bromides, buryrates, camsylates, carbonates, hydrochlorates, chlorides, citrates, clavulanates, dichlorhydrates, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methylsulphates, mucates, napsylates, nitrates, 3-hydroxy-2-naphthoates, oleates, oxalates, palmitates, pamoates (1,1-methylene-bis-2-hydroxy-3-naphtoates, or emboates), pantothenates, phosphates, picrates, polygalacturonates, propionates, p-toluenesulphonates, salicylates, stearates, subacetates, succinates, sulphates, sulphosalicylates, suramates, tannates, tartrates, teoclates, tosylates, triethiodides, trifluoroacetates and valerianates.

The compositions of the invention advantageously comprise a pharmaceutically acceptable carrier or excipient. The pharmaceutically acceptable carrier can be selected from the carriers classically used according to each mode of administration. According to the mode of administration envisaged, the compounds can be in solid, semi-solid or liquid form. For solid compositions such as tablets, pills, powders, or granules that are free or are included in gelatin capsules, the active substance can be combined with: a) diluents, for example lactose, dextrose, sucrose, mannitol, sorbitol, cellulose and/or glycine; b) lubricants, for example silica, talc, stearic acid, its magnesium or calcium salt and/or polyethylene glycol; c) binders, for example magnesium and aluminum silicate, starch paste, gelatin, tragacanth, methylcellulose, sodium carboxymethyl cellulose and/or polyvinylpyrrolidone; d) disintegrants, for example starch, agar, alginic acid or its sodium salt, or effervescent mixtures; and/or d) absorbents, dyes, flavoring agents and sweeteners. The excipients can be, for example, mannitol, lactose, starch, magnesium stearate, sodium saccharin, talc, cellulose, glucose, sucrose, magnesium carbonate and analogues of pharmaceutical quality. For semi-solid compositions such as suppositories, the excipient can, for example, be an emulsion or oily suspension, or polyalkylene glycol-based, such as polypropylene glycol. Liquid compositions, in particular injectables or those included in a soft capsule, can be prepared, for example, by dissolution, dispersion, etc., of the active substance in a pharmaceutically pure solvent such as, for example, water, physiological saline solution, aqueous dextrose, glycerol, ethanol, oil and analogues thereof.

The compositions or conjugates of the invention can be administered by any suitable route and, in a non-restrictive way, by parenteral route, such as, for example, in the form of preparations that can be injected by subcutaneous, intravenous or intramuscular route; by oral route (or per os), such as, for example, in the form of coated or uncoated tablets, gelatin capsules, powders, pellets, suspensions or oral solutions (one such form for oral administration can be either with immediate release or with extended or delayed release); by rectal route such as, for example, in the form of suppositories; by topical route, in particular by transdermal route, such as, for example, in the form of patches, pomades or gels; by intranasal route such as, for example, in aerosol and spray form; by perlingual route; or by intraocular route.

The pharmaceutical compositions typically comprise an effective dose of a VHH or conjugate of the invention. A "therapeutically effective dose" as described herein refers to the dose that gives a therapeutic effect for a given condition and administration schedule. It is typically the average dose of an active substance to administer to appreciably improve some of the symptoms associated with a disease or a pathological state. For example, in treating a cancer of the brain or of other tissue, a pathology, a lesion or a disorder of the CNS, the dose of an active substance that decreases, prevents, delays, eliminates or stops one of the causes or symptoms of the disease or disorder would be therapeutically effective. A "therapeutically effective dose" of an active substance does not necessarily cure a disease or disorder but will provide a treatment for this disease or disorder so that its appearance is delayed, impeded or prevented, or its symptoms are attenuated, or its term is modified or, for example, is less severe, or the recovery of the patient is accelerated.

It is understood that the "therapeutically effective dose" for a person in particular will depend on various factors, including the activity/effectiveness of the active substance, its time of administration, its route of administration, its toxicity, its rate of elimination and its metabolism, drug combinations/interactions and the severity of the disease (or disorder) treated on a preventive or curative basis, as well as the age, weight, overall health, sex and/or diet of the patient.

Depending on the substance coupled, the conjugates and compositions of the invention can be used for treating, preventing, diagnosing or imaging numerous pathologies, notably pathologies affecting the CNS, infectious pathologies or cancers. The VHH of the invention have the capacity to target TfR-expressing cells, particularly cells which exhibit marked expression of said receptor, such as notably cancer cells, nervous or non-nervous tissue and/or to cross cell membranes, notably those of the physiological barriers of the CNS and more particularly the blood-tumor barrier (BTB) of cancerous nervous tissue. The TfR is enriched in organs such as bone marrow, placenta and in the gastrointestinal tract. TfR is also highly expressed in brain endothelial cells but not in endothelial cells lining the vessels in other tissues. TfR expression has been confirmed at the plasma membrane of purified brain microvessels and cultured endothelial cells from rat, mouse, pig and non-human primate.

In this respect, the invention relates to the use of pharmaceutical conjugates or compositions as described above for treating or preventing CNS pathologies or disorders, brain tumors or other cancer cells, and bacterial, viral, parasitic or fungal infectious pathologies of the brain or other tissues.

The invention also relates to a VHH, conjugate, or compositions as described above for use for diagnosing, imaging or treating CNS pathologies or disorders, brain tumors or other cancer cells, and bacterial, viral, parasitic or fungal infectious pathologies of the brain or other tissues.

The invention also relates to a VHH, conjugate, or compositions as described above for use for treating, imaging and/or diagnosing a brain tumor or other types of cancer.

The invention to a VHH, conjugate or composition such as defined above for use for treating, imaging and/or diagnosing neurodegenerative pathologies such as, in a non-restrictive manner, Alzheimer's disease, Parkinson's disease, stroke, Creutzfeldt-Jakob disease, bovine spongiform encephalopathy, multiple sclerosis, amyotrophic lateral sclerosis, etc.

The invention also relates to a VHH, conjugate or composition such as defined above for use for treating, imaging and/or diagnosing neurological pathologies such as, in a non-restrictive manner, epilepsy, migraine, encephalitis, CNS pain, etc.

The invention also relates to a VHH, conjugate or composition such as defined above for use for treating, imaging and/or diagnosing rare diseases such as, in non-restrictive manner lysosomal storage diseases, Farber disease, Fabry disease, Gangliosidosis GM1 and GM2, Gaucher disease, different mucopolysaccharidoses etc.

The invention also relates to a VHH, conjugate or composition such as defined above for use for treating, imaging and/or diagnosing neuropsychiatric pathologies such as, in a non-restrictive manner, depression, autism, anxiety, schizophrenia, etc.

The invention also relates to a VHH, conjugate or composition such as defined above for use for treating, imaging and/or diagnosing cancers such as, in a non-restrictive manner, glioblastoma, pancreatic cancer, ovarian cancer, hepatocellular cancer, etc.

The invention also relates to a VHH, conjugate or composition such as defined above, wherein the conjugated agent is a virus or a virus-like particle, such as a recombinant virus. The invention may indeed be used to increase brain or cancer or any TfR enriched tissue delivery of recombinant (e.g., replication-defective or attenuated) viruses used in gene therapy, such as adenoviruses, adeno-associated viruses, lentiviruses, retroviruses, etc, or virus-like particles. Coupling to a virus or VLP may be performed e.g., by coupling to the capsid protein of the virus.

The invention also relates to methods for treating any of the above conditions or diseases by administering to a subject in need thereof a VHH, conjugate or composition of the invention.

The invention also relates to the use of a VHH, conjugate or composition of the invention for the manufacture of a medicament for treating any of the above conditions or diseases.

Other aspects and advantages of the present invention will become apparent upon consideration of the examples below, which are only illustrative in nature and which do not limit the scope of the present application.

EXAMPLES

Example I

Validation of TfR Expression at the BBB.

We analyzed cell membrane expression profile of the TfR in brain endothelium of various species. The kit ProteoExtract Subcellular Proteome Extraction Kit (Calbiochem, La Jolla, CA, USA) was used to prepare membrane extracts of digested or non-digested brain microvessels (BMVs) and of primocultures of brain microvascular endothelial cells (BMEC) from rat, mouse, pig and non-human primate (NHP; rhesus monkey) (FIG. 1).

Membrane extracts were quantified using the BioRad DC Protein Assay (Bio-Rad, Hercules, CA, USA) following manufacturer's instructions. Membrane proteins were separated by sodium dodecyl sulfate polyacrylamide gel electrophoresis (SDS-PAGE) on 4-12% polyacrylamide gels, and transferred onto nitrocellulose membranes (ThermoFisher Scientific). Proteins were probed with a primary antibody against TfR (Genetex GTX102596; 1/1000), followed by an HRP-conjugated donkey anti-rabbit IgG secondary antibody (Jackson ImmunoResearch) diluted 1/10000. Finally, proteins were detected using chemiluminescence.

As shown in FIG. 1, TfR is expressed in digested and non-digested brain microvessels from rat, mouse, pig and non-human primate. TfR is also expressed in brain endothelial cells from mouse rat and pig (note that only 1 µg of membrane proteins was loaded on SDS-PAGE for brain microvascular endothelial cells versus 10 µg or 5 µg for brain microvessels). TfR expression is enhanced in digested NHP brain microvessels.

These data demonstrate that the TfR represents a valid target for designing molecules for in vivo applications.

Example II

Construction of CHO Cell Lines Stably Expressing Human and Mouse TfR.

The prerequisite to the identification and characterization of TfR-binding VHHs was the establishment in eukaryotic cells (Chinese hamster ovary cells, CHO) of stable cell lines expressing hTfR and mTfR, constitutively and at high rates. These cell lines were then used i) for the identification and characterization of agents binding to the receptor expressed at the cell surface, in its native configuration; and ii) to test whether the receptor could internalize such agents by endocytosis.

For the construction of these cell lines, the cDNA coding for the hTfR was cloned using sequence information available in databases (accession number: NM_003234.3). The primers necessary for cDNA amplification by RT-PCR were selected (see table below), comprising at their end (in bold type) the restriction sites (EcoRI and SalI) necessary for cloning in the pEGFP-C1 expression vector (Clontech) (FIG. 2-A).

```
Receptor Primer sequences hTfR    (F) ATATATGAATTCGGCTCGGGACGGAGGACGC (SEQ ID NO: 65)
        (R) TTAATTGTCGACAGAACTCATTGTCCCAACCGTCAC (SEQ ID NO: 66)
```

Total RNA prepared from human brain was used for RT-PCR amplification of the cDNA fragment coding for hTfR. After amplification, the PCR product was digested by EcoRI-SalI restriction enzymes, and ligated in the pEGFP-C1 expression vector (Clontech), digested by the same restriction enzymes. After transfection in eukaryotic cells, this vector enables the expression, under control of the CMV promoter, of the hTfR fused to EGFP at its N-Terminal end, i.e., at the end of its intracellular domain. After transforming competent E. coli DH5a bacteria, obtaining isolated colonies and preparing plasmid DNA, both strands of the construct were fully sequenced for verification.

Plasmid coding for the mTfR fused to EGFP was purchased from GeneCopoeia (plasmid reference: EX-Mm05845-M29).

Transient transfections in CHO-K1 cells were carried out and used to select stable transfectants by limit dilution and resistance to antibiotic (G418). These cell lines were amplified while maintaining selective pressure.

Confocal photomicrographs taken after immunocytochemistry on fixed (PFA) cell lines using Alexa647-conjugated Transferrin (Tf-Alexa647) confirm in FIG. 2-B co-localization between EGFP (in green) and Tf-Alexa647 (in red) and therefore, good expression and functional binding of the receptor.

Membrane expression of the receptors of the expected size was checked by western blot on cell membranes extracted with ProteoExtract Subcellular Proteome Extraction Kit. Antibodies were directed either against GFP or against the TfR. Proteins corresponding to the combined sizes of EGFP and h/mTfR (170 kDa), were recognized by an anti-GFP antibody and by an anti-TfR antibody (FIG. 2-C). A CHO K1 wild type (WT) cell line was used as negative control and antibodies detected no proteins.

These data confirm the expression of functional receptor at the cell surface of the CHO cell lines.

Example III

Generation of VHHs that Bind the TfR.

A llama (Lama glama) was immunized subcutaneously 4 times with membrane preparations from CHO stable cell lines expressing the human and murine receptors of interest. VHH library construction was performed as previously described (Alvarez-Rueda et al., 2007, Behar et al., 2009). Briefly, mRNAs coding for VHH were amplified by RT-PCR from the total RNAs of peripheral blood mononuclear cells isolated by ficoll gradient, and cloned into the pHEN1 phagemid. Reiterative selections enabled the isolation of phages presenting VHH exhibiting strong affinity for the TfR expressed at the cell surface.

In total, more than 700 clones were screened for their ability to bind the TfR, and roughly 100 clones were sequenced.

VHHs with improved binding (to both the murine and the human cell lines), cell penetration and transport properties were obtained. Illustrative VHH are VHH A, VHH B, VHH C, VHH D (see also the list of sequences). These VHHs do not bind to cells of the control CHO cell line.

Furthermore, TfR-binding VHH with appropriate, improved binding properties, were generated by site-directed mutagenesis. More particularly, site directed mutagenesis was performed to introduce single alanine substitutions into the VHH A complementarity-determining regions (CDR) 1, 2 and 3, giving rise to the VHH A1 to A9. VHH A1 and A2 were mutated in the CDR1, VHH A3 and A4 were mutated in the CDR2 and VHH A5 to A9 were mutated in the CDR3. Furthermore, single site directed mutagenesis was also performed by substituting some CDR amino acids by structurally-close amino acids. VHH A10-A19 were obtained, wherein VHH A10 and A11 were mutated in the CDR1, VHH A12 to A14 were mutated in the CDR2, and VHH A15 to A19 were mutated in the CDR3.

Moreover, humanized TfR-binding VHH were generated, to improve in vivo efficacy by, e.g., avoiding immunogenicity, and were designated VHH A20-A25.

In addition, tagged VHH molecules were produced, to facilitate purification and/or coupling.

The amino acid sequences of each of these VHH are provided in the Sequence Listing.

Example IV

Binding and Endocytosis of Purified VHHs of the Invention

To confirm the ability of selected VHH molecules to bind the TfR, and to be endocytosed, immunocytochemical experiments involving the incubation of VHHs on living CHO cell lines expressing the TfR fused to EGFP, detected using a mouse anti-cMyc primary antibody (ThermoFisher) followed by an Alexa594-conjugated donkey anti-mouse secondary antibody (Jackson ImmunoResearch), were performed and observed with a confocal microscope. The results obtained with VHH A are shown as an example.

As shown in FIG. 3, the VHH binds to the CHO-hTfR-EGFP (FIG. 3-B) and CHO-mTfR-EGFP (FIG. 3-A) cell lines and is incorporated by endocytosis to accumulate in the cells as shown using triton permeabilization, which is not the case for the control VHH (VHH Z) (FIG. 3-C, D).

Example V

Determination of Binding Affinity

The binding properties of VHHs with affinity for the TfR were tested using flow cytometry, and apparent affinities ($K_d$ $app$) were determined. All experiments were performed in 96 well plates using $2-3 \times 10^5$ cells/well, at 4° C. with shaking. CHO cell lines expressing the TfR fused to EGFP or CHO WT cells were saturated with PBS/BSA 2% solution during 30 min to avoid nonspecific binding, followed by incubation with purified VHHs at concentrations ranging from 2 µM to 1 µM for 1 hr. After one wash in PBS/BSA 2%, cells were incubated for 1 hr with an anti-6His tag antibody (mouse), washed twice with PBS/BSA 2%, and incubated for 45 min with an Alexa647-conjugated anti-mouse secondary antibody. After two last washes in PBS/BSA 2%, cells were fixed or not by incubation for 15 min with PBS/PFA 2%, washed once with PBS and finally resuspended in PBS. Fluorescence levels were assessed using a MACSQuant flow cytometer (Miltenyi) or an Attune NxT flow cytometer (Thermo Fisher Scientific).

There was no nonspecific labelling in the control conditions where cells were incubated with control VHH (VHH Z). All tested VHHs induced a concentration-dependent shift of the signal, confirming binding to the receptor of interest (FIG. 4-A). No labeling of the CHO WT control cells was detected with all the tested VHHs (not shown). The VHH $K_{d\ app}$ were calculated using GraphPad Prism software (FIG. 4-B). $K_{d\ app}$ were in the same range for all VHH, ranging from 7.5 nM (VHH B) to 56 nM (VHH D) on mTfR, and from 1.6 nM (VHH B) to 2.7 nM (VHH A) on hTfR.

Example VI

Competition Assays Between Purified VHHs with Affinity for the TfR and the Natural Ligand.

To evaluate the ability of selected VHHs to compete with Transferrin (Tf), the TfR natural ligand, for the binding to the receptor, competition assays using flow cytometry experiments were performed. In a first step, competitors in dilution series were incubated on CHO cells expressing the receptor of interest fused to EGFP, for 1 hr at 4° C. Secondly, tracers at EC90 were added and incubated 1 hr more, and were then detected with the appropriate revelation system (FIG. 5).

TfR-binding VHHs were used as tracers (FIG. 5-B) and competitors (FIG. 5-C). In all conditions, there was no competition between VHHs and the ligand Tf, suggesting than VHHs bind to TfR on an epitope different than that of Tf.

Example VII

Determination of Binding Affinity of VHH A1-A19

The binding properties of VHH A1-A19 for the TfR were tested using flow cytometry, and apparent affinities ($K_{d\ app}$) were determined. All experiments were performed in 96 well plates using 2×10$^5$ cells/well, at 4° C. with shaking. CHO cell lines stably expressing the hTfR or the mTfR fused to EGFP or CHO WT cells were saturated with PBS/BSA 2% solution during 30 min to avoid non-specific binding, followed by incubation with purified VHHs at concentrations ranging from 50 μM to 5 μM for 1 hr. After one wash in PBS/BSA 2%, cells were incubated for 1 hr with an anti-6His tag antibody (mouse), washed twice with PBS/BSA 2%, and incubated for 45 min with an Alexa647-conjugated anti-mouse secondary antibody. After two last washes in PBS/BSA 2%, cells were fixed by incubation for 15 min with PBS/PFA 2%, washed once with PBS and finally resuspended in PBS and stored at 4° C. Fluorescence levels were assessed using an Attune NxT Flow Cytometer (Thermo Fisher Scientific).

VHH A1-A19 all induced a concentration-dependent shift of the signal on both cell lines (with the exception of VHH A12) confirming their efficient binding to the receptor of interest (FIGS. 11; 12). While VHH A, VHH A1 to A4, and VHH A10 to A15, showed similar $B_{max}$ (plateau of the curve) on both hTfR and mTfR expressing cell lines, VHH A6 to A9 and VHH A16 to A19 showed slight to drastic lower $B_{max}$ on both cell lines, as well as slight to strong curve shift. Only VHH A12 showed a lower $B_{max}$ and a strong curve shift on the hTfR expressing cell line compared to the other VHH Ax. No labeling of the CHO WT control cells was detected with all the tested VHHs (not shown).

The VHH $K_{d\ app}$ were calculated using GraphPad Prism software (FIG. 11-B; 12-B). Regarding the binding to the human TfR, VHH A, A1 to A4, A6, A9 to A11, and A13 to A17, all showed similar $K_{d\ app}$ of about 3-4 nM. Conversely, VHH A5, A8, A18 and 19 showed slightly lower affinities of 9.2 to 25 nM, while VHH A7 and A12 showed drastically lower affinities of 255 nM and 363 nM, respectively.

Regarding the binding to the mouse TfR, VHH A and A9 showed similar $K_{d\ app}$ of about 50 nM. All other VHH Ax showed slightly lower affinities of 131 to 259 nM, with the exception of VHH A5, A8 and A18 that showed significantly lower affinities of 604 nM, 427 nM and 416 nM, respectively.

Example VIII

Binding and Endocytosis of Purified VHH-Fc Fusion Molecules with Affinity for TfR and Affinity Determination.

Anti-TfR VHH molecules of the invention were fused to an IgG Fc fragment. To produce the fusion protein, DNA fragments encoding the VHHs (with no tag) were amplified by PCR and cloned into the pINFUSE-IgG1-Fc2 vector (InvivoGen) in order to encode a human IgG1-Fc fragment encompassing in its N-ter or in its C-ter the VHHs. Fusion proteins were prepared using the Expi293 Expression System according to the manufacturer's instructions (Life Technologies). Seventy-two hrs post-transfection, supernatants were recovered and purified using Protein A GraviTrap columns (GE Healthcare). The purified fusion proteins were quantified using an in-house anti-Fc ELISA.

Immunocytochemistry experiments on CHO cell lines expressing the TfR fused to EGFP, involving the incubation of VHH-Fc fusion proteins on living cells, detected using an Alexa594-conjugated anti-hFc antibody (Jackson ImmunoResearch), photographed with a confocal microscope, were performed to confirm the ability of fusion proteins to bind the targeted receptor of interest.

The results demonstrate that conjugates of the invention can bind and be endocytosed by cells (FIG. 7). No binding of a control VHH-Fc conjugate (VHH Z-Fc) on cells was observed, showing the specificity of the interaction.

The binding properties of VHH-Fc and Fc-VHH fusion proteins with an affinity for the TfR were tested in flow cytometry experiments, and apparent affinity ($K_{d\ app}$) were determined. All experiments were performed in 96 well plates using 2-3×10$^5$ cells/well, at 4° C. with shaking. CHO cell lines expressing the receptors of interest fused to EGFP or CHO WT cells were saturated with PBS/BSA 2%, followed by an incubation with purified VHH-Fcs or Fc-VHHs at concentrations ranging from 350 nM to 0.03 μM for 1 hr. After washes, cells were incubated for 1 hr with an Alexa647-conjugated anti-hFc antibody (Jackson ImmunoResearch). After 3 last washes and cells resuspension in PBS, fluorescence was immediately measured using a MACSQuant flow cytometer (Miltenyi), and results were analyzed with the MACSQuant software.

All VHH-Fc and Fc-VHH fusion proteins induced a concentration-dependent shift of the signal, confirming binding to the receptor of interest. The VHH-Fc and Fc-VHH $K_{d\ app}$ were calculated using GraphPad Prism software (FIG. 8-B). The $K_{d\ app}$ of almost all VHHs were greatly improved by the conjugation with an Fc fragment, with $K_{d\ app}$ ranging from 0.44 nM to 51 nM for TfR-binding VHH-Fcs and Fc-VHHs.

Example IX

Endocytosis and Transport of VHHs of the Invention in an In Vitro BBB Model.

We used rat or mouse brain microvascular endothelial cells (BMEC) and rat or mouse astrocytes to set up the co-culture model. This type of in vitro BBB model is used to evaluate the passive passage or active transport of numerous molecules, notably pharmacological agents, across BMEC and thus, by extrapolation, their capacity to reach CNS tissue in vivo. The different models developed to date (bovine, porcine, murine, human) have ultrastructural properties characteristic of the brain endothelium, notably tight junctions, absence of fenestrations, low permeability to hydrophilic molecules and high electrical resistance. Moreover, these models have shown solid correlations between the results of measurements taken on various molecules evaluated in vitro and in vivo for their property of passing across the BBB. To date, all the data obtained show that these in vitro BBB models mimic the situation in vivo by reproducing some of the complexities of the cell environment that exist in vivo, while preserving the advantages associated with cell culture experimentation.

For example, the in vitro rat BBB model brings into play a co-culture of BMEC and astrocytes (Molino et al., 2014, J. Vis. Exp. 88, e51278). Prior to cell culture, membrane inserts (Corning, Transwell 1.0 m porosity, for 96-well or 12-well plates) were treated on the upper part with collagen type IV and fibronectin in order to enable optimal adhesion of BMEC and to create the conditions of a basal lamina. Primary cultures of mixed astrocytes were established from neonatal rat cerebral cortex. Briefly, meninges were removed and the cortical pieces were mechanically, then enzymatically dissociated in a trypsin solution. Dissociated cells were seeded into cell culture flasks in glial cell media (GCM) containing DMEM supplemented with 10% fetal bovine serum then frozen in liquid nitrogen for later use. Primary cultures of BMEC were prepared from 5-6 weeks old Wistar rats. Briefly, the cortical pieces were mechanically then enzymatically dissociated in a collagenase/dispase solution. The digested tissues were separated by a density-dependent centrifugation in 25% bovine serum albumin. The microvessels pellet were seeded on culture flask, pre-coated with collagen type IV and fibronectin, in endothelial cell media (ECM) containing DMEM/FF12 supplemented with 20% bovine platelet poor plasma derived serum and basic fibroblast growth factor (bFGF) 2 ng/ml. Five days before the establishment of the co-culture, astrocytes were thawed and plated in 12-well or 96-well plates (abluminal compartment). The BMEC were then distributed on the upper surface of the filters (luminal compartment) in co-culture. Under these conditions, in vitro models differentiate, express junction-related proteins within 3 days and remain optimally differentiated during 3 more days.

The binding/uptake at the BBB of inventive VHHs conjugated to the human Fc fragment of an IgG1 antibody (VHH-Fc) was verified on the in vitro rat model described above (FIG. 9). VHH A-Fc or VHH B-Fc were co-incubated with Tf-Alexa647 for 2 hrs on live rBMEC monolayers at 37° C. (FIG. 9A). Following this co-incubation, the cell monolayer was washed extensively and fixed with PFA 4%. The cell monolayer was permeabilized with a solution of 0.1% triton X-100. VHH-Fcs were detected using immunostaining with an antibody against the human Fc fragment. Then confocal microscopy was used to assess the co-localization between fluorescence signal of VHH A-Fc or VHH B-Fc with Tf-A647 (FIG. 9A).

The results show that, following this 2 hr co-incubation, VHH A-Fc and VHH B-Fc were readily endocytosed and co-localized almost perfectly with Tf-Alexa647. This analysis of co-localization of different TfR ligands (VHH A-Fc, VHH B-Fc and Tf-A647) confirmed the specificity of the inventive VHHs to their target receptor.

For transport across the rBMEC monolayers to the abluminal compartment, the VHH-Fcs were incubated at 10 nM in the luminal compartment of the culture system for 24 hrs to 72 hrs (FIG. 9-C, D). Prior to experiment, filter inserts, containing rBMEC monolayers were placed in 96-well plates containing fresh transport buffer (75 µl in the luminal and 250 µl in the abluminal compartments). To evaluate the integrity of the BBB in vitro and the absence of toxicity for the endothelial cells, VHH-Fcs were co-incubated with lucifer yellow (LY), a small fluorescent molecule that does not cross the BBB. 24 hrs after incubation, the inserts were transferred to another 96-well plate containing fresh transport buffer for another interval of 48 hrs. At the end of transport, LY accumulated in the abluminal compartment was quantified by fluorescence spectrophotometry and results were expressed as endothelial surface permeability (or Pe) in $10^{-3}$ cm/min. The in vitro barrier was considered "permeable" or "open" if the Pe value of LY was greater than $0.6 \times 10^{-3}$ cm/min. Transendothelial electrical resistance (TEER), measured with an ohmmeter and expressed in ohm·cm², also makes it possible to measure BBB integrity in vitro during tests of passage across the BBB. The quality threshold value is set at >400 ohm·cm². The experiments carried out show an absence of toxicity of the VHH-Fcs, and an absence of deleterious effects on the permeability properties of the BBB (not shown). The content of Fc-fragment of inventive VHH-Fcs in the inputs (TO), the luminal compartments at the end of transport experiment (T72 hrs, product recovery) and the abluminal compartments (transport intervals of 24 hrs and +48 hrs) were quantified using an in-house anti-Fc ELISA assay with sensitivity between 0.5-50 femtomoles. Absorbance units were transformed in femtomoles per insert (surface area of 0.143 cm² for inserts of a 96-well plate).

Our results show that VHH B-Fc and VHH A-Fc conjugates show higher transport than VHH Z-Fc (negative control), around 10-fold at 24 hrs and 5-fold at 72 hrs. This transport reached an apparent saturation between 24 hrs and 72 hrs, further suggesting the involvement of a specific and saturable receptor mediated process (FIG. 9-D).

Example X

Pharmacokinetic and Organ Uptake of VHH-Fc Conjugates In Vivo.

To assess the potential of VHH-Fc conjugates of the invention to target organs enriched with receptors of interest in vivo, conjugates VHH A-Fc, VHH A-Fc-Agly and VHH Z-Fc were injected into tail vein at 5 mg/kg and the mice were perfused with saline at different times. Plasmas and brains were collected. Brains were processed by the capillary depletion method to isolate brain parenchyma from capillary. The amount of VHH-Fc in plasma, brain parenchyma and microvessels was measured using an in-house anti-Fc ELISA. Results are presented as concentrations (nM), or by organ-to-plasma ratio (FIG. 10).

TfR-binding conjugates VHH A-Fc and VHH A-Fc-Agly, exhibit a significant brain targeting at 2 hrs pi, with concentrations of 0.25 and 0.32 nM in brain parenchyma for VHH A-Fc and VHH A-Fc-Agly respectively, compared to 0.07 nM for the control VHH Z-Fc (FIG. 10-B). When looking at parenchyma-to-plasma ratios, a clear advantage is confirmed, especially at 24 hrs pi where VHH A-Fc-Agly is still measurable in brain parenchyma whereas there is only 8 nM present in plasma (FIG. 10-D). In microvessels, VHH A-Fc and VHH A-Fc-Agly accumulate significantly more than VHH Z-Fc at 2 hrs pi, with concentrations 9 and 5 times higher, respectively. Moreover, VHH A-Fc concentration in microvessels is still 3 times higher than VHH Z-Fc at 24 hrs pi (FIG. 10-C). These results were confirmed when looking at microvessel-to-plasma ratios (FIG. 10-E). These results demonstrate that TfR-targeting VHH of the invention can be used to effectively deliver or to improve pharmacokinetic properties of agents, notably protein cargos.

Example XI

Design and Production of a Therapeutic Antibody Fused to a VHH

Anti-TfR VHH A, A1, A5, A6, A7 and A8 of the invention (with no tag) were fused to the mouse IgG1 13C3 monoclonal antibody, with high specific affinity for the protofibril form of β-amyloid peptide (WO2009/065054). To produce the 13C3-HC-VHH fusion proteins, a DNA fragment encoding the selected VHH was synthetized and cloned into the 13C3 heavy chain (HC) vector in order to encode the 13C3-HC-VHH conjugate containing, in its C-ter, the selected VHH sequence fused to the antibody heavy chain C-ter amino acid residue. In another set of experiments, the DNA fragment encoding the selected VHH was cloned into the 13C3 light chain (LC) vector in order to encode the 13C3 LC conjugate containing in its C-ter the selected VHH sequence fused to the antibody light chain C-ter amino acid residue.

Fusion proteins were produced using the Expi293™ Expression System according to the manufacturer's instructions (Life Technologies). Seventy-two hrs post-transfection, supernatants were recovered and purified using HiTrap® Protein G High Performance columns (GE Healthcare). The purified fusion proteins were quantified using 280 nm absorbance measurement.

The amino acid sequence of a 13C3-HC-VHHA conjugate is provided as SEQ ID NO: 93:

QVQLQQSGPELVRPGVSVKISCKGSGYTFTDYAMHWVKQSHAKSLEWI

GVISTKYGKTNYNQKFKGKATMTVDKSSSTAYMELARLTSEDSAIYYC

ARGDDGYSWGQGTSVTVSSAKTTPPSVYPLAPGSAAQTNSMVTLGCLV

KGYFPEPVTVTWNSGSLSSGVHTFPAVLQSDLYTLSSSVTVPSSTWPS

ETVTCNVAHPASSTKVDKKIVPRDCGCKPCICTVPEVSSVFIFPPKPK

DVLTITLTPKVTCVVVDISKDDPEVQFSWFVDDVEVHTAQTQPREEQF

NSTFRSVSELPIMHQDWLNGKEFKCRVNSAAFPAPIEKTISKTKGRPK

APQVYTIPPPKEQMAKDKVSLTCMITDFFPEDITVEWQWNGQPAENYK

NTQPIMDTDGSYFVYSKLNVQKSNWEAGNTFTCSVLHEGLHNHHTEKS

LSHSPGGGGMAEVQLVESGGGVVQPGGSLKLSCVASGTDESINFIRW

YRQAPGKQREEVAGETATGNTNYADSMKGRFTISRDNTKNAVYLQIDS

LKPEDTAVYYCMLDKWGQGTQVTVSSAAA

In bold is the 13C3 Variable Heavy Chain sequence; underlined is the 13C3 Constant Heavy Chain sequence; bold and underlined is a Gly linker; double underline MA and C-ter AAA residues result from cloning and may be optionally removed. The remaining is the VHH.

The amino acid sequence of a 13C3-LC-VHHA conjugate is provided as SEQ ID NO: 94:

DVVMTQTPLSLPVSLGDQASISCRSGQSLVHSNGNTYLHWYLQKPGQS

PKLLIYTVSNRFSGVPDRFSGSGSGSDFTLKISRVEAEDLGVYFCSQN

TFVPWTFGGGTKLEIKRADAAPTVSIFPPSSEQLTSGGASVVCFLNNF

YPKDINVKWKIDGSERQNGVLNSWTDQDSKDSTYSMSSTLTLTKDEYE

RHNSYTCEATHKTSTSPIVKSFNRNECSGSGGGGMAEVQLVESGGGV

VQPGGSLKLSCVASGTDFSINFIRWYRQAPGKQREFVAGFTATGNTNY

ADSMKGRFTISRDNTKNAVYLQIDSLKPEDTAVYYCMLDKWGQGTQV

TVSSAAA

In bold is the 13C3 Variable kappa Light Chain sequence; FGGGTK is the J region; LEIKR is a multiple cloning site; underlined is the 13C3 Constant kappa Light Chain sequence; bold and underlined is a Gly linker; double underline MA and C-ter AAA residues result from cloning and may be optionally removed. The remaining is the VHH.

Determination of Binding Affinity

The binding properties of 13C3 conjugates of the invention for the TfR were tested using flow cytometry, and apparent affinities ($K_{d\ app}$) were determined. All experiments were performed in the same conditions than described in example VII, with 13C3 constructs incubated at concentrations ranging from 15 µM to 7 µM and detected with an Alexa647-conjugated anti-mouse antibody.

All 13C3-HC-VHH fusion proteins induced a concentration-dependent shift of the signal on both hTfR and mTfR expressing cell lines, confirming binding to the receptor (FIG. 13). All 13C3 fusion proteins showed the same hTfR binding profile, with the exception of the VHH A7 fusion that showed a slightly lower $B_{max}$. All fusion proteins showed different binding profiles on the mTfR, with the 13C3-HC-VHH A1 fusion showing a 2-fold lower $B_{max}$ than the 13C3-HC-VHH A, while A5 to A8 13C3 fusions showed very low $B_{max}$.

The 13C3 fusions $K_{d\ app}$ were calculated using GraphPad Prism software (FIG. 13-B). Affinities for the hTfR were similar for all fusions, with $K_{d\ app}$ of about 10-20 nM. Despite different $B_{max}$, VHH A, A1 and A6 13C3 HC fusions showed similar affinities of 10 to 20 nM, while 13C3-HC-VHH A8 and 13C3-LC-VHH A fusions showed lower affinities of 315 nM and 106 nM, respectively.

Example XII

Brain Uptake of 13C3-HC-VHH and 13C3-LC-VHH Fusions In Vivo.

To assess the potential of VHH of the invention to promote the brain uptake of antibodies, 13C3-HC-VHH A and 13C3-HC-VHH A1 conjugates, or unvectorized 13C3 were injected into C57Bl6 mice tail vein at the dose of 35 nmoles/kg. The mice were perfused with saline solution at different times. Brains were collected at 2 hrs and 6 hrs time points post-injection (p.i.). Half of mice brains were processed to isolate the capillary network from the brain parenchyma by a capillary depletion method that consists in centrifugation on 20% Dextran solution (Sigma Aldrich) of the resuspended half brain homogenate and recovery of the parenchyma fraction. The second halves of mice brains were directly processed (homogenized and lysed) for total brain quantification. The amount of 13C3-HC-VHH conjugate in total brain and brain parenchyma was measured using an in-house qualified Meso Scale Discovery (MSD) direct coating (Abeta) immunoassay. (CV<20% and recovery±30%). Results are presented as concentrations (nM) (FIG. 14).

Results show that TfR-binding conjugates 13C3-HC-VHH A and 13C3-HC-VHH A1 exhibited a significant brain uptake advantage at 2 and 6 hrs p.i. by comparison to the control unvectorized 13C3 antibody (FIG. 14-A). The total brain concentrations of 13C3-HC-VHH A and 13C3-HC-VHH A1 are 8 and 5-fold more important than that of the unvectorized 13C3 antibody at 6 hrs pi, respectively.

Crossing of the BBB by 13C3-HC-VHH A and 13C3-HC-VHH A1 was confirmed by the fact that, at 6 hrs pi, the concentrations measured in brain parenchyma, depleted of the microcapillary network, were 10- and 9-fold more important than that of the unvectorized 13C3, respectively (FIG. 14-B).

Additional brain uptake investigations further confirmed that 13C3-HC-VHH A and 13C3-LC-VHH A (the light chain vectorized version) demonstrated BBB crossing at the dose of 70 nmoles/kg with parenchyma accumulation respectively 6-fold and 5-fold higher than unvectorized 13C3 antibody at 4 hrs p.i..

Example XIII

Synthesis of VHH-siRNA Conjugates

An anti-GFP siRNA comprising chemical modifications for high resistance to nucleases, namely siGFPst1, was conjugated to a tagged VHH A to generate a VHH A-siGFPst1 bioconjugate. The same conjugation strategy was used to conjugate siGFPst1 to the irrelevant VHH Z as a negative control with the same structure and size as the VHH A-siGFPst1 conjugate but with no TfR-targeting capacity.

The conjugation strategy involved a convergent synthesis with the parallel modification of: i) the VHH to site-specifically introduce an azido-linker; and ii) the siGFPst1 to introduce a constrained azido moiety complementary to the azido functional group. In a final step, both functionalized VHH-azide and alkyne-siGFPst1 precursors are linked to each other using a copper-free click reaction.

Synthesis of the VHH-Azide

Site-specific conjugation to the VHH was performed using a Bacterial Transglutaminase (BTG)-based ligation strategy. The BTG enzyme catalyzes the formation of an isopeptidic bond between a glutamine residue inserted in a tag sequence specifically recognized by the BTG enzyme (namely a Q-tag) and an amino-functionalized substrate. The amino-functionalized substrate introduced was a heterobifunctional linker containing at one end an amino moiety that we proved to be a substrate of the BTG enzyme and at the other end an azido moiety for the conjugation to the siGFPst1 through copper-free click chemistry.

BTG-Conjugation Protocol:

3-azido-1-propanamine (20.eq/Gln) was dissolved in PBS (1×) and added to the Q-tagged VHH produced in-house. BTG (Zedira, Darmstadt, Germany) was then introduced in the mixture (0.1 U/nmol of Gln) which was allowed to react at 37° C. overnight. Purification of the crude mixture was performed through chromatography on a Protino Ni-ida 1000 packed column according to the manufacturer's instructions to isolate the VHH-azide from excess of starting material as well as potential by-products. Absorbance was read at 280 nm to calculate the amount of purified VHH-azide construct and thus the conjugation yield (in the 70-80% range).

Final VHH-azide were characterized by LCMS analysis to check their identity and purity.

Synthesis of the Alkyne-siGFPst1 siGFPst1 was purchased from Dharmacon with a 3' amine modification on the sense strand (N6-siGFPst1) to allow its further functionalization by the alkyne moiety required for the click chemistry conjugation with the VHH-azide.

siGFPst1 Functionalization Protocol

N6-siGFPst1 (1 eq) was dissolved in a NaB (0.09M; pH 8.5) conjugation buffer to obtain a final concentration between 0.3 and 0.8 mM. DBCO-NHS (20 eq, DMSO) was then added to this solution. Reaction mixture was stirred for 2 hours at room temperature. Alkyne-siGFPst1 was purified by precipitation in cold absolute ethanol. Absorbance was read at 260 nm to calculate the amount of purified alkyne-siGFPst1 construct and thus the conjugation yield (in the 40-50% range).

Final alkyne-siGFPst1 was characterized by analytical HPLC to check its identity and purity.

Synthesis of the VHH-siGFPst1

Both VHH-azide and alkyne-siGFPst1 precursors were finally conjugated by a copper-free click chemistry reaction to obtain the final conjugate VHH-siGFPst1.

VHH-siGFPst1 Conjugation Protocol:

Alkyne-siGFPst1 (2 eq.) was dissolved in PBS (1×) and added to the VHH-azide (1 eq., final concentration in the 100 µM range in PBS (1×)). Reaction mixture was allowed to stir overnight at room temperature. Final conjugate was first purified by gel filtration chromatography onto a Superdex75 column and second, concentrated using an Amicon Ultra-centrifugation filter (10K). Absorbance was read at 260 nm to calculate the amount of purified VHH-siGFPst1 construct and thus the conjugation yield (overall yield in the 30% range).

Final VHH-siGFPst1 (VHH A-siGFPst1 and VHH Z-siGFPst1) were characterized by analytical SEC-HPLC and agarose-gel electrophoresis to check their identity and purity.

Example XIV

In Vitro Gene Silencing Activity of a VHH-siRNA Bioconjugate

Specific cellular targeting and productive intracellular delivery of therapeutic nucleic acids, especially siRNAs, oligonucleotides remain a major challenge. The structural and physico-chemical features of these molecules, being multiply charged hydrophilic oligomers, prevent them from entering any subcellular compartment if unassisted. VHH of the invention were used to transport a small interfering RNA (siRNA) across cellular membranes to access the cytosol.

First, the apparent hTfR-binding affinity ($K_{d\ app}$) of the VHH A-siGFPst1 and VHH B-siGFPst1 bioconjugates was evaluated as described in Example VII (Determination of binding affinity of VHH A1-A19) by adding concentrations ranging from 2 µM to 30 µM during 1 hr at 4° C. on the same CHO-hTfR-GFP cells. Quantification of the cell-surface bound molecules was performed by anti-6His immunocytochemistry and experimental data were fit with a nonlinear regression using GraphPad Prism® software. As previously shown with the free VHH A and VHH B, the VHH A-siGFPst1 and VHH B-siGFPst1 bioconjugates demonstrated concentration-dependent and saturable binding to the cell-surface target hTfR, with $K_{d\ app}$ values in the same low nanomolar range as unconjugated VHH A and VHH B (FIG. 15A). No significant binding was observed with the control VHH Z. This, in turn, confirmed that coupling of the VHH A and VHH B to an siRNA does not alter their ability to bind specifically and efficiently to hTfR.

Second, the intrinsic silencing activity of the VHH-siGFPst1 bioconjugate was assessed in living CHO cell lines stably expressing the TfR fused to EGFP (CHO-hTfR-EGFP cells) by transfection of the conjugate at 25 nM using Dharmafect 1 (Dharmacon) for direct delivery into the cytosol. The total cellular amount of GFP was quantified 72 hours post-transfection using flow cytometry. The results demonstrate that the VHH A-siGFPst1 conjugate induced a ca. 85% reduction of GFP protein levels, in the same range than the unconjugated siGFPst1 or the control VHH Z-siGFPst1 conjugate (FIG. 15B). This confirms that coupling of either the VHH A or Z does not hamper the siRNA to undergo RISC loading and exert its silencing activity. In another series of experiments, the VHH A-siGFPst1 conjugate was transfected on CHO-hTfR-EGFP cells at concentrations ranging from 10 nM to 1 µM and the total cellular amount of GFP was quantified 120 hours post-transfection using flow cytometry. This resulted in a concentration-dependent reduction of GFP protein levels, with an IC50 of 50.4 µM and a maximum silencing efficiency in this condition of −90.2% (FIG. 15C).

Third, the ability of the VHH A, once conjugated to siGFPst1, to trigger hTfR-mediated endocytosis and subsequent delivery into the cytosol of target cells in pharmacological amounts was assessed. The VHH A-siGFPst1 or the control VHH Z-siGFPst1 bioconjugates were incubated on CHO-hTfR-GFP cells at 1 µM during 120 hrs at 37° C. to allow free uptake, delivery to the cytosol and gene silencing to take place at the mRNA transcript and protein levels. This led to a significant ca. −70% reduction of GFP protein levels with the TfR-binding VHH A-siGFPst1 bioconjugate, while no silencing was observed with the control VHH Z-siGFPst1 bioconjugate (FIG. 15D). Next, the VHH A-siGFPst1 bioconjugate was incubated on CHO-hTfR-GFP cells at concentrations ranging from 3 µM to 10 µM during 120 hrs. This resulted in a concentration-dependent reduction of GFP protein levels, with an IC50 of 2.73±0.23 nM and a maximum silencing efficiency in this condition of −61.6±2.9% (FIG. 15E). This demonstrates that cell-surface binding to hTfR and subsequent endocytosis of VHH A-siGFPst1 bioconjugate allows its delivery into the cytosol in pharmacological amounts, with an IC50 in the same nanomolar range than hTfR-binding affinity of the bioconjugate.

Fourth, the involvement of the hTfR in the observed silencing effect of the VHH A-siGFPst1 bioconjugate upon free uptake on CHO-hTfR-GFP cells was confirmed in a competition assay. In this experiment, VHH A-siGFPst1 was incubated during 120 hrs at 37° C. at the saturating concentration of 30 nM, as defined from the previous experiment, either alone or in the presence of a 100× excess of the free VHHs A, B or Z. The results demonstrated that the ca. 60% reduction of GFP protein levels was almost completely abrogated in the presence of the free VHH A or VHH B (GFP protein levels were maintained at 85% and 96% of the control levels, respectively). Importantly, no competition was observed when using an excess of the irrelevant VHH Z (FIG. 15F). This unequivocally confirmed that the silencing effect of the VHH A-siGFPst1 bioconjugate was indeed due to hTfR-mediated cellular uptake and subsequent delivery into the cell cytoplasm.

Fifth, the TfR-mediated GFP-silencing effect of the VHH A-siGFPst1 bioconjugate was evaluated using a pulse-chase procedure. CHO-hTfR-GFP cells were exposed to VHH A-siGFPst1 at concentrations ranging from 300 nM to 1 µM during a short duration (6 hours), followed by chase in ligand-free medium up to a total duration of 120 hrs. This experiment allowed to evaluate the contribution of early cellular uptake to the silencing effect previously observed by continuous incubation during 120 hrs. As observed using continuous incubation, the VHH A-siGFPst1 bioconjugate again induced a concentration-dependent reduction of GFP protein levels, with a similar IC50 of 1.24 nM and a maximum silencing efficiency of −54.2% (FIG. 15G). This result suggests that most of the effect previously observed upon 120 hrs continuous incubation was due to productive TfR-mediated uptake within the first 6 hrs. This finding is of particular interest since in vivo the plasma pharmacokinetic profile of such bioconjugates generally allows tissue exposure at therapeutic levels during only a few hours when administered by intravenous or subcutaneous bolus injection. The TfR-targeting VHH described here hence represents a viable tool for targeted and efficient gene silencing in vivo.

Finally, the ability of the VHH B to trigger hTfR-mediated endocytosis and subsequent gene silencing was evaluated by incubating the VHH B-siGFPst1 bioconjugate on CHO-hTfR-GFP cells at 30 nM during 120 hrs. The result showed a ca. −60% reduction in GFP levels, similar to that obtained with the VHH A-siGFPst1 bioconjugate, confirming that these VHHs display a similar TfR-targeting and intracellular delivery potential (FIG. 15H).

To the best of our knowledge, receptor-mediated hepatocyte uptake through the asialoglycoprotein receptor (ASGPR) using triantennary GalNAc as a targeting ligand is the only ligand/receptor system able to trigger specific and efficient gene silencing at nanomolar concentrations. However, the use of this system for in vivo therapeutic applications with therapeutic nucleic acids is restricted to hepatic targets, since ASGPR is expressed in vivo exclusively in hepatocytes. Therefore, the present invention provides a new ligand/receptor system for the targeting and intra-cytoplasmic delivery at nanomolar concentrations of therapeutic nucleic acids, such as siRNAs, into extra-hepatic organs and tissues expressing the TfR.

Example XV

Synthesis of VHH-NODAGA Conjugates
Design of the Q-Tagged VHH A

In the present example, a DNA fragment encoding VHH A with an AlaLinker, a HisTag, a GlyLinker and a Q-tag (AAA-HisTag-GGG-LQR sequence) introduced at its C-terminal end) was synthetized and cloned into the pHEN1 vector.

BTG-Based Preparation of the VHH A-Azide:

3-azido-1-propanamine (20.eq/Gln) was dissolved in PBS (1×) and added to the LQR-tagged VHH A produced in-house. BTG (Zedira, Darmstadt, Germany) was introduced in the mixture (0.1 U/nmol of Gln). The reaction mixture was then allowed to react at 37° C. overnight. Purification of the crude mixture was performed through chromatography on a Protino Ni-ida 1000 packed column according to the manufacturer's instructions to isolate the VHH A-azide from excess of starting material as well as potential by-products. Absorbance was read at 280 nm to calculate the amount of purified VHH A-azide construct and thus the conjugation yield (in the 70-80% range). Final VHH A-azide was characterized by LCMS analysis to check its identity and the purity.

Click Chemistry Reaction to Conjugate VHH A-Azide to Commercial Alkyne-NODAGA

VHH A-azide (1 eq.) was allowed to react with the heterobifunctional NODAGA-BCN (5 eq.) (Chematech, Dijon, France) in PBS at room temperature. Reaction was monitored by LCMS. After completion of the reaction, the final conjugate was purified through chromatography on a Protino Ni-ida 1000 packed column according to the manufacturer's instructions to isolate the VHH A-azide from excess of starting material as well as potential by-products. Absorbance was read at 280 nm to calculate the amount of purified VHH A-NODAGA construct and thus the conjugation yield (in the 50-60% range). Final VHH A-NODAGA was characterized by LCMS analysis to check its identity and purity.

Example XVI

PET Imaging of a VHH-68Ga Bioconjugate in a Subcutaneous Mouse Model of Glioblastoma Tumor.

Glioblastoma is the most common primary malignant brain tumor and the U87 cell line, a human primary glioblastoma cell line, is known to express a high TfR levels. In order to assess the glioblastoma targeting of VHH of the invention, the radiolabeled VHH A-NODAGA bioconjugate was intravenously administered to mice previously implanted with glioblastoma cells (xenograft model) and PET-Scan imaging was performed.

Radiolabeling of VHH A-NODAGA and Binding Affinity Validation

First, VHH A-NODAGA was radiolabeled using 68Ga chloride. Gallium was obtained in 68Ga3+ form using a commercial TiO2-based 68Ge/68Ga generator (Obninsk). A radiolabeling reaction was conducted by reacting 60 μg of VHH A-NODAGA with 74-148 MBq (2-4 mCi) of 68Ga in 400 μL of ammonium acetate buffer (1M, pH 6) at 25° C. for 10 minutes. The VHH A-68Ga radiochemical purity (RPC) obtained was >95%.

Following radiolabeling, the apparent hTfR-binding affinities ($K_{d\ app}$) of the VHH A-NODAGA and VHH A-68Ga bioconjugates were evaluated as described in Example VII (Determination of binding affinity of VHH A1-19) by adding concentrations ranging from 2 μM to 30 μM during 1 hr at 4° C. on the same CHO-hTfR-GFP cells. Quantification of the cell-surface bound VHH A bioconjugates was performed by anti-6His immunocytochemistry and experimental data were fit with a nonlinear regression using GraphPad Prism® software. VHH A-NODAGA and VHH A-68Ga bioconjugates demonstrated concentration-dependent and saturable binding to the cell-surface target receptor hTfR, with $K_{d\ app}$ values in the same low nanomolar range as the unconjugated VHH A (FIG. 16A). No significant binding was observed with the control VHH Z. This confirmed that coupling of the VHH A to a NODAGA ligand and radiolabeling protocol does not alter its ability to bind specifically to hTfR.

PET-Scan Imaging

Animal studies were performed according to the protocols approved by the Aix-Marseille Ethic comity (Comity 14). Four weeks old BALB/c Nude Mouse female were obtained from Charles River Inc. Mice (n=6) were implanted subcutaneously between the shoulders with U87-MG cells ($2 \times 10^6$) in 100 μL of complete medium containing 50% Matrigel (Corning). On day 28 following implantation (when the tumors reached a volume comprised between 300-700 mm3), the animals were administered with an intravenous single bolus dose of 5±1 MBq of VHH A-68Ga. Following administration, the biodistribution in the glioblastoma cancer xenograft and other tissues was assessed using PET-imaging.

PET/CT scans were acquired during 2 hrs for 3 mice and at 2 hrs post injection (p.i.) for the 3 other mice. PET and PET/CT studies were performed on a microPET/microCT rodent model scanner (nanoPET/CT®, Mediso). Anesthesia was induced with 5% isoflurane and maintained at 1.5%. To improve image quality, 20 million coincidence events per mouse were acquired for every static PET emission scan (energy window, 400-600 keV; time: 20 minutes for one FOV). For dual modality PET/CT, CT images (35 kVp, exposure time of 350 ns and medium zoom) were obtained, and anatomical registration, as well as attenuation of correction, was applied to the corresponding PET scans.

Imaging pictures of animals injected with VHH A-68Ga showed a significant accumulation at the tumor site (FIG. 16B, 1.46% of ID/g) and a good tumor/muscle ratio (4.0). Thus, experiments showed a clear and selective imaging and labeling of glioblastoma cancer with VHH A-68Ga at day 28, consistent with the known high expression levels of the TfR.

LIST OF SEQUENCES

| sdAb | Amino acid sequence | CDR1 | CDR2 | CDR3 |
|---|---|---|---|---|
| A | EVQLVESGGGVVQPGGSLKLSCVASGTDFSINFIRWYRQAPGKQREFVAGFTATGNTNYADSMKGRFTISRDNTKNAVYLQIDSLKPEDTAVYYCYMLDKWGQGTQVTVSS(AAAEQKLISEEDLNGAAHHHHHHGS)$_x$ SEQ4 | GTDFSINF SEQ 1 | FTATGNT SEQ 2 | YMLDK SEQ 3 |
| B | EVQLVESGGGVVQPGGSLRLSCAASGEIFSINFMRWYRQAPGKQREWVAGFTRDGSTNYPDSAKGRFTISRDNAKNTVYLQIDSLKPEDTAVYYCYMLDTWGQGTQVTVSS(AAAEQKLISEEDLNGAAHHHHHHGS)$_x$ SEQ8 | GEIFSINF SEQ5 | FTRDGST SEQ6 | YMLDT SEQ7 |
| C | EVQLVESGGGLVQPGGSLRLSCTASGGPIEQYPMGWFRRAPGKERELVASISRGDGTYYAISSVKGRFTISRDNAENTVFLQMNSLKPDDTAVYYCGAGINPTKIWGQGTQVTVSS(AAAEQKLISEEDLNGAAHHHHHHGS)$_x$ SEQ12 | GGPIEQYP SEQ9 | ISRGDGTY SEQ10 | GAGINPTKI SEQ11 |

| | | LIST OF SEQUENCES | | |
|---|---|---|---|---|
| D | EVQLVESGGGEVQPGGSLKLSCVASG<u>TDF</u><br><u>SINF</u>VRWYRQRPGKQREWVAGF<u>TANGDT</u><br><u>NY</u>PDSMKGRFTISRDNAKNTV<u>Y</u>LQINSLK<br>SEDTAVYYC<u>YMLDN</u>VVGQGTQVTVSS(AA<br>AEQKLIS<u>EE</u>DLNGAAHHHHHHGS)<sub>x</sub><br>SEQ16 | GTDFSINF<br>SEQ13 | FTANGDT<br>SEQ14 | YMLDN<br>SEQ15 |
| A1 | EVQLVESGGGVVQPGGSLKLSCVASG<u>AD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMLDK</u>WGQGTQVTVSS(AA<br>AEQKLIS<u>EE</u>DLNGAAHHHHHHGS)<sub>x</sub><br>SEQ18 | GADSIN<br>F<br>SEQ17 | FTATGNT<br>SEQ2 | YMLDK<br>SEQ3 |
| A2 | EVQLVESGGGVVQPGGSLKLSCVASG<u>TA</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMLDK</u>WGQGTQVTVSS(AA<br>AEQKLIS<u>EE</u>DLNGAAHHHHHHGS)<sub>x</sub><br>SEQ20 | GTAFSINF<br>SEQ19 | FTATGNT<br>SEQ2 | YMLDK<br>SEQ3 |
| A3 | EVQLVESGGGVVQPGGSLKLSCVASG<u>TD</u><br><u>FSINF</u>IRWYRQAPGKQREFVAGF<u>TAAGNT</u><br><u>NY</u>ADSMKGRFTISRDNTKNAV<u>Y</u>LQIDSLK<br>PEDTAVYYC<u>YMLDK</u>WGQGTQVTVSS(AA<br>AEQKLIS<u>EE</u>DLNGAAHHHHHHGS)<sub>x</sub><br>SEQ22 | GTDFSINF<br>SEQ1 | FTAAGNT<br>5EQ21 | YMLDK<br>SEQ3 |
| A4 | EVQLVESGGGVVQPGGSLKLSCVASG<u>TD</u><br><u>FSINF</u>IRWYRQAPGKQREFVAGF<u>TATGAT</u><br><u>NY</u>ADSMKGRFTISRDNTKNAV<u>Y</u>LQIDSLK<br>PEDTAVYYC<u>YMLDK</u>WGQGTQVTVSS(AA<br>AEQKLIS<u>EE</u>DLNGAAHHHHHHGS)<sub>x</sub><br>SEQ24 | GTDFSINF<br>SEQ1 | FTATGAT<br>SEQ23 | YMLDK<br>SEQ3 |
| A5 | EVQLVESGGGVVQPGGSLKLSCVASG<u>TD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>AMLDK</u>WGQGTQVTVSS(AA<br>AEQKLIS<u>EE</u>DLNGAAHHHHHHGS)<sub>x</sub><br>SEQ26 | GTDFSINF<br>SEQ1 | FTATGNT<br>SEQ2 | AMLDK<br>SEQ25 |
| A6 | EVQLVESGGGVVQPGGSLKLSCVASG<u>TD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YALDK</u>WGQGTQVTVSS(AA<br>AEQKLIS<u>EE</u>DLNGAAHHHHHHGS)<sub>x</sub><br>SEQ28 | GTDFSINF<br>SEQ1 | FTATGNT<br>SEQ2 | YALDK<br>SEQ27 |
| A7 | EVQLVESGGGVVQPGGSLKLSCVASG<u>TD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMADK</u>WGQGTQVTVSS(A<br>AAEQKLIS<u>EE</u>DLNGAAHHHHHHGS)<sub>x</sub><br>SEQ30 | GTDFSINF<br>SEQ1 | FTATGNT<br>SEQ2 | YMADK<br>SEQ29 |
| A8 | EVQLVESGGGVVQPGGSLKLSCVASG<u>TD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMLAK</u>WGQGTQVTVSS(AA<br>AEQKLIS<u>EE</u>DLNGAAHHHHHHGS)<sub>x</sub><br>SEQ32 | GTDFSINF<br>SEQ1 | FTATGNT<br>SEQ2 | YMLAK<br>SEQ31 |
| A9 | EVQLVESGGGVVQPGGSLKLSCVASG<u>TD</u><br><u>FSINF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMLDA</u>WGQGTQVTVSS(AA<br>AEQKLIS<u>EE</u>DLNGAAHHHHHHGS)<sub>x</sub><br>SEQ34 | GTDFSINF<br>SEQ1 | FTATGNT<br>SEQ2 | YMLDA<br>SEQ33 |
| A10 | EVQLVESGGGVVQPGGSLKLSCVASG<u>TD</u><br><u>FSLNF</u>IRWYRQAPGKQREFVAGF<u>TATGNT</u><br><u>NY</u>ADSMKGRFTISRDNTKNAV<u>Y</u>LQIDSLK<br>PEDTAVYYC<u>YMLDK</u>WGQGTQVTVSS(AA<br>AEQKLIS<u>EE</u>DLNGAAHHHHHHGS)x<br>SEQ68 | GTDFSLN<br>F<br>SEQ67 | FTATGNT<br>SEQ2 | YMLDK<br>SEQ3 |

| | LIST OF SEQUENCES | | | |
|---|---|---|---|---|
| A11 | EVQLVESGGGVVQPGGSLKLSCVASGTDFSINYIRWYRQAPGKQREFVAGFTATGNTNYADSMKGRFTISRDNTKNAVYLQIDSLKPEDTAVYYCYMLDKWGQGTQVTVSS(AAAEQKLISEEDLNGAAHHHHHHGS)x SEQ70 | GTDFSINY SEQ69 | FTATGNT SEQ2 | YMLDK SEQ3 |
| A12 | EVQLVESGGGVVQPGGSLKLSCVASGTDFSINFIRWYRQAPGKQREFVAGITATGNTNYADSMKGRFTISRDNTKNAVYLQIDSLKPEDTAVYYCYMLDKWGQGTQVTVSS(AAAEQKLISEEDLNGAAHHHHHHGS)x SEQ72 | GTDFSINF SEQ1 | ITATGNT SEQ71 | YMLDK SEQ3 |
| A13 | EVQLVESGGGVVQPGGSLKLSCVASGTDFSINFIRWYRQAPGKQREFVAGFSATGNTNYADSMKGRFTISRDNTKNAVYLQIDSLKPEDTAVYYCYMLDKWGQGTQVTVSS(AAAEQKLISEEDLNGAAHHHHHHGS)x SEQ74 | GTDFSINF SEQ1 | FSATGNT SEQ73 | YMLDK SEQ3 |
| A14 | EVQLVESGGGVVQPGGSLKLSCVASGTDFSINFIRWYRQAPGKQREFVAGFTATGNSNYADSMKGRFTISRDNTKNAVYLQIDSLKPEDTAVYYCYMLDKWGQGTQVTVSS(AAAEQKLISEEDLNGAAHHHHHHGS)x SEQ76 | GTDFSINF SEQ1 | FTATGNS SEQ75 | YMLDK SEQ3 |
| A15 | EVQLVESGGGVVQPGGSLKLSCVASGTDFSINFIRWYRQAPGKQREFVAGFTATGNTNYADSMKGRFTISRDNTKNAVYLQIDSLKPEDTAVYYCFMLDKWGQGTQVTVSS(AAAEQKLISEEDLNGAAHHHHHHGS)x SEQ78 | GTDFSINF SEQ1 | FTATGNT SEQ2 | FMLDK SEQ77 |
| A16 | EVQLVESGGGVVQPGGSLKLSCVASGTDFSINFIRWYRQAPGKQREFVAGFTATGNTNYADSMKGRFTISRDNTKNAVYLQIDSLKPEDTAVYYCYILDKWGQGTQVTVSS(AAAEQKLISEEDLNGAAHHHHHHGS)x SEQ80 | GTDFSINF SEQ1 | FTATGNT SEQ2 | YILDK SEQ79 |
| A17 | EVQLVESGGGVVQPGGSLKLSCVASGTDFSINFIRWYRQAPGKQREFVAGFTATGNTNYADSMKGRFTISRDNTKNAVYLQIDSLKPEDTAVYYCYMIDKWGQGTQVTVSS(AAAEQKLISEEDLNGAAHHHHHHGS)x SEQ82 | GTDFSINF SEQ1 | FTATGNT SEQ2 | YMIDK SEQ81 |
| A18 | EVQLVESGGGVVQPGGSLKLSCVASGTDFSINFIRWYRQAPGKQREFVAGFTATGNTNYADSMKGRFTISRDNTKNAVYLQIDSLKPEDTAVYYCYMVDKWGQGTQVTVSS(AAAEQKLISEEDLNGAAHHHHHHGS)x SEQ84 | GTDFSINF SEQ1 | FTATGNT SEQ2 | YMVDK SEQ83 |
| A19 | EVQLVESGGGVVQPGGSLKLSCVASGTDFSINFIRWYRQAPGKQREFVAGFTATGNTNYADSMKGRFTISRDNTKNAVYLQIDSLKPEDTAVYYCYMLEKWGQGTQVTVSS(AAAEQKLISEEDLNGAAHHHHHHGS)x SEQ86 | GTDFSINF SEQ1 | FTATGNT SEQ2 | YMLEK SEQ85 |
| A20 | EVQLVESGGGVVQPGGSLRLSCAASGTDFSINFMSWVRQAPGKGLEWVAGFTATGNTNYADSVKGRFTISRDNAKNTLYLQMNSLRPEDTAVYYCYMLDKWGQGTQVTVSS(AAAEQKLISEEDLNGAAHHHHHHGS)x SEQ87 | GTDFSINF SEQ1 | FTATGNT SEQ2 | YMLDK SEQ3 |
| A21 | EVQLVESGGGVVQPGGSLRLSCAASGTDFSINFIRWVRQAPGKQREFVAGFTATGNTNYADSVKGRFTISRDNAKNTLYLQMNSLRPEDTAVYYCYMLDKWGQGTQVTVSS(AAAEQKLISEEDLNGAAHHHHHHGS)x SEQ88 | GTDFSINF SEQ1 | FTATGNT SEQ2 | YMLDK SEQ3 |

LIST OF SEQUENCES

| | | | | |
|---|---|---|---|---|
| A22 | EVQLVESGGGVVQPGGSLRLSCAASGTDF SINFMHWVRQAPGKGLEWVAGFTATGNT NYADSVKGRFTISRDNAKNTLYLQMNSL RPEDTAVYYCYMLDKWGQGTQVTVSS(A AAEQKLISEEDLNGAAHHHHHHGS)x SEQ89 | GTDFSINF SEQ1 | FTATGNT SEQ2 | YMLDK SEQ3 |
| A23 | EVQLVESGGGVVQPGGSLRLSCAASGTDF SINFMSWVRQAPGKQREFVAGFTATGNT NYADSVKGRFTISRDNAKNTLYLQMNSL RPEDTAVYYCYMLDKWGQGTQVTVSS(A AAEQKLISEEDLNGAAHHHHHHGS)x SEQ90 | GTDFSINF SEQ1 | FTATGNT SEQ2 | YMLDK SEQ3 |
| A24 | EVQLVESGGGVVQPGGSLRLSCAASGTDF SINFIRWVRQAPGKGLEWVAGFTATGNT NYADSVKGRFTISRDNAKNTLYLQMNSL RPEDTAVYYCYMLDKWGQGTQVTVSS(A AAEQKLISEEDLNGAAHHHHHHGS)x SEQ91 | GTDFSINF SEQ1 | FTATGNT SEQ2 | YMLDK SEQ3 |
| A25 | EVQLVESGGGVVQPGGSLRLSCAASGTDF SINFIHWVRQAPGKGLEWVAGFTATGNT NYADSVKGRFTISRDNAKNTLYLQMNSL RPEDTAVYYCYMLDKWGQGTQVTVSS(A AAEQKLISEEDLNGAAHHHHHHGS)x SEQ92 | GTDFSINF SEQ1 | FTATGNT SEQ2 | YMLDK SEQ3 |

| sdAb | SEQ ID | nucleotide sequences (including optional tags) |
|---|---|---|
| A | 52 | GAGGTgcAGCTGGTGGAGTCTGGGGGAGGCGTGGTGCAGCCTGGGGGGTCTCTAAAACTCTC CTGCGTAGCCTCGGGAACGGACTTCAGTATCAATTTTATACGCTGGTACCGCCAGGCTCCAG GGAAGCAGCGCGAGTTCGTCGCAGGATTTACTGCGACTGGTAACACAAACTATGCAGACTCC ATGAAGGGGCGATTCACCATCTCCAGAGACAACACCAAGAACGCGGTGTATCTGCAAATAGA CAGCCTGAAACCTGAGGACACGGCCGTGTATTACTGCTATATGTTGGACAAGTGGGGCCAGG GGACCCAGGTCACCGTCTCCTCAGCGGCCGCAGAACAAAAACTCATCTCAGAAGAGGATCTG AATGGGGCCGCACATCACCACCATCACCATGGGAGCTAG |
| A1 | 53 | GAGGTgcAGCTGGTGGAGTCTGGGGGAGGCGTGGTGCAGCCTGGGGGGTCTCTAAAACTCTC CTGCGTAGCCTCGGGAGCGGACTTCAGTATCAATTTTATACGCTGGTACCGCCAGGCTCCAG GGAAGCAGCGCGAGTTCGTCGCAGGATTTACTGCGACTGGTAACACAAACTATGCAGACTCC ATGAAGGGGCGATTCACCATCTCCAGAGACAACACCAAGAACGCGGTGTATCTGCAAATAGA CAGCCTGAAACCTGAGGACACGGCCGTGTATTACTGCTATATGTTGGACAAGTGGGGCCAGG GGACCCAGGTCACCGTCTCCTCAGCGGCCGCAGAACAAAAACTCATCTCAGAAGAGGATCTG AATGGGGCCGCACATCACCACCATCACCATGGGAGCTAG |
| A2 | 54 | GAGGTgcAGCTGGTGGAGTCTGGGGGAGGCGTGGTGCAGCCTGGGGGGTCTCTAAAACTCTC CTGCGTAGCCTCGGGAACGGCGTTCAGTATCAATTTTATACGCTGGTACCGCCAGGCTCCAG GGAAGCAGCGCGAGTTCGTCGCAGGATTTACTGCGACTGGTAACACAAACTATGCAGACTCC ATGAAGGGGCGATTCACCATCTCCAGAGACAACACCAAGAACGCGGTGTATCTGCAAATAGA CAGCCTGAAACCTGAGGACACGGCCGTGTATTACTGCTATATGTTGGACAAGTGGGGCCAGG GGACCCAGGTCACCGTCTCCTCAGCGGCCGCAGAACAAAAACTCATCTCAGAAGAGGATCTG AATGGGGCCGCACATCACCACCATCACCATGGGAGCTAG |
| A3 | 55 | GAGGTgcAGCTGGTGGAGTCTGGGGGAGGCGTGGTGCAGCCTGGGGGGTCTCTAAAACTCTC CTGCGTAGCCTCGGGAACGGACTTCAGTATCAATTTTATACGCTGGTACCGCCAGGCTCCAG GGAAGCAGCGCGAGTTCGTCGCAGGATTTACTGCGGCGGGTAACACAAACTATGCAGACTCC ATGAAGGGGCGATTCACCATCTCCAGAGACAACACCAAGAACGCGGTGTATCTGCAAATAGA CAGCCTGAAACCTGAGGACACGGCCGTGTATTACTGCTATATGTTGGACAAGTGGGGCCAGG GGACCCAGGTCACCGTCTCCTCAGCGGCCGCAGAACAAAAACTCATCTCAGAAGAGGATCTG AATGGGGCCGCACATCACCACCATCACCATGGGAGCTAG |
| A4 | 56 | GAGGTgcAGCTGGTGGAGTCTGGGGGAGGCGTGGTGCAGCCTGGGGGGTCTCTAAAACTCTC CTGCGTAGCCTCGGGAACGGACTTCAGTATCAATTTTATACGCTGGTACCGCCAGGCTCCAG GGAAGCAGCGCGAGTTCGTCGCAGGATTTACTGCGACTGGTGCGACAAACTATGCAGACTCC ATGAAGGGGCGATTCACCATCTCCAGAGACAACACCAAGAACGCGGTGTATCTGCAAATAGA CAGCCTGAAACCTGAGGACACGGCCGTGTATTACTGCTATATGTTGGACAAGTGGGGCCAGG GGACCCAGGTCACCGTCTCCTCAGCGGCCGCAGAACAAAAACTCATCTCAGAAGAGGATCTG AATGGGGCCGCACATCACCACCATCACCATGGGAGCTAG |
| A5 | 57 | GAGGTgcAGCTGGTGGAGTCTGGGGGAGGCGTGGTGCAGCCTGGGGGGTCTCTAAAACTCTC CTGCGTAGCCTCGGGAACGGACTTCAGTATCAATTTTATACGCTGGTACCGCCAGGCTCCAG GGAAGCAGCGCGAGTTCGTCGCAGGATTTACTGCGACTGGTAACACAAACTATGCAGACTCC |

| | | |
|---|---|---|
| | | LIST OF SEQUENCES |
| | | ATGAAGGGGCGATTCACCATCTCCAGAGACAACACCAAGAACGCGGTGTATCTGCAAATAGA<br>CAGCCTGAAACCTGAGGACACGGCCGTGTATTACTGC<u>GCGATGTTGGACAAGTGGGGCCAGG</u><br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A6 | 58 | GAGGTGcAGCTGGTGGAGTCTGGGGGAGGCGTGGTGCAGCCTGGGGGGTCTCTAAAACTCTC<br>CTGCGTAGCCTCGGGAACGGACTTCAGTATCAATTTTATACGCTGGTACCGCCAGGCTCCAG<br>GGAAGCAGCGCGAGTTCGTCGCAGGATTTACTGCGACTGGTAACACAAACTATGCAGACTCC<br>ATGAAGGGGCGATTCACCATCTCCAGAGACAACACCAAGAACGCGGTGTATCTGCAAATAGA<br>CAGCCTGAAACCTGAGGACACGGCCGTGTATTACTGC<u>TATGCGTTGGACAAGTGGGGCCAGG</u><br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A7 | 59 | GAGGTGcAGCTGGTGGAGTCTGGGGGAGGCGTGGTGCAGCCTGGGGGGTCTCTAAAACTCTC<br>CTGCGTAGCCTCGGGAACGGACTTCAGTATCAATTTTATACGCTGGTACCGCCAGGCTCCAG<br>GGAAGCAGCGCGAGTTCGTCGCAGGATTTACTGCGACTGGTAACACAAACTATGCAGACTCC<br>ATGAAGGGGCGATTCACCATCTCCAGAGACAACACCAAGAACGCGGTGTATCTGCAAATAGA<br>CAGCCTGAAACCTGAGGACACGGCCGTGTATTACTGC<u>TATATGGCGGACAAGTGGGGCCAGG</u><br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A8 | 60 | GAGGTGcAGCTGGTGGAGTCTGGGGGAGGCGTGGTGCAGCCTGGGGGGTCTCTAAAACTCTC<br>CTGCGTAGCCTCGGGAACGGACTTCAGTATCAATTTTATACGCTGGTACCGCCAGGCTCCAG<br>GGAAGCAGCGCGAGTTCGTCGCAGGATTTACTGCGACTGGTAACACAAACTATGCAGACTCC<br>ATGAAGGGGCGATTCACCATCTCCAGAGACAACACCAAGAACGCGGTGTATCTGCAAATAGA<br>CAGCCTGAAACCTGAGGACACGGCCGTGTATTACTGC<u>TATATGTTGGCGAAGTGGGGCCAGG</u><br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A9 | 61 | GAGGTGcAGCTGGTGGAGTCTGGGGGAGGCGTGGTGCAGCCTGGGGGGTCTCTAAAACTCTC<br>CTGCGTAGCCTCGGGAACGGACTTCAGTATCAATTTTATACGCTGGTACCGCCAGGCTCCAG<br>GGAAGCAGCGCGAGTTCGTCGCAGGATTTACTGCGACTGGTAACACAAACTATGCAGACTCC<br>ATGAAGGGGCGATTCACCATCTCCAGAGACAACACCAAGAACGCGGTGTATCTGCAAATAGA<br>CAGCCTGAAACCTGAGGACACGGCCGTGTATTACTGC<u>TATATGTTGGACGCGTGGGGCCAGG</u><br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| B | 62 | GAgGTGCAGCTGGTGGAGTCTGGGGGagGCGTGGTGCAGCCTGGGGGGTCTCTGAGACTCTC<br>CTGTGCAGCCTCTGGAGAGATCTTCAGTATCAATTTTATGCGCTGGTACCGCCAGGCTCCAG<br>GGAAGCAGCGCGAGTGGGTCGCAGG<u>TTTTACTAGGGATGGAAGCAC</u>AAACTATCCAGACTCC<br>GCGAAGGGCCGATTCACCATCTCTAGAGACAACGCCAAGAACACGGTGTATCTGCAAATAGA<br>CAGCCTGAAACCTGAGGACACGGCCGTCTATTATTGTTATATGTTGGACACCTGGGCCAGG<br>GGACCCAGGTCACTGTCTCCTCAGCGCCGCAGAACAAAAACTCATCTCAGAAGAGGATCTG<br>AATGGGGCCGCACATCACCACCATCACCATGGGAGCTAG |
| C | 63 | GAGGTGCAGCTGGTGGAGTCTGGGGGAGGCTTGGTGCAGCCTGGGGGTTCTCTGAGACTCTC<br>CTGTACAGCCTCTGGAGGCCCCATCGAGCAGTATCCCATGGGCTGGTTCCGCCGGGCCCCAG<br>GAAAGGAGCGTGAATTGGTAGCAAGTATTAGCCGAAGTGGAGATGGCACATAC<u>TATGCAATC</u><br><u>TCTTCCGTGAAGGGCCGATTCACCATCTCTAGAGACAACGCCGAGAACACGGTATTTCTGCA</u><br><u>AATGAACAGCCTGAAACCTGACGACACGGCCGTTTATTACTGTGGGGCTGGTATAAACCCAA</u><br><u>CCAAGATCTGGGGCCAGGGGACCCAGGTCACCGTCTCCTCA</u>GCGGCCGCAGAACAAAAACTC<br>ATCTCAGAAGAGGATCTGAATGGGGCCGCACATCACCACCATCACCATGGGAGCTAG |
| D | 64 | GAGGTGCAGCTGGTGGAgTCTGGGGGAggCGAGGTGCAGCCTgGGGGGTCTCTGAGAACTCTC<br>CTGTGTAGCCTCTGGAACCGACTTCAGTATCAATTTTGTGCGCTGGTACCGTCAGCGTCCAG<br>GGAAGCAGCGCGAGTGGGTCGCAGGATTTACTGCGAATGGTGATACAAACTATCCAGACTCC<br>ATGAAGGGGCGATTCACCATTTCCAGAGACAACGCCaGAATACGGTGTATCTACAGATAAA<br>CAGCCTGAAATCTGAGGACACGGCCGTCTATTATTGCTATATGTTAgATAATTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A10 | 95 | GagGTGCAGCTGGTGGagtCTGGGGgaGgCGTGGTGCAGCctGGGGGGTCTCtAAAACTCTC<br>CTGCgtAGCCTCGGGAACGGACTTCagtctgAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A11 | 96 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTacATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |

| | | LIST OF SEQUENCES |
|---|---|---|
| A12 | 97 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGAATTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A13 | 98 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTTCAGCGACTGgTAACACAAACTATGCAGACTCC<br>AtgAAGGGGCGATTCACCATCTCCAG<u>AGACAACACCAAGAACGCGGT</u>GTATCTGCAAATAGA<br>CAGCCTGAAACCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A14 | 99 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACTCAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A15 | 100 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTTTATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A16 | 101 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATTTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A17 | 102 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGATTGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A18 | 103 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAGAGACAACACCAAGAACGCGGTGTATCTGCAAATAGA<br>CAGCCTGAAACCTGAGGACACGGCCGTGTATTACTGCTATATGGTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A19 | 104 | GagGTGCAGCTGGTGGagtCTGGGGgaGgCGTGGTGCAGCctGGGGGGTCTCtAAAACTCTC<br>CTGCgtAGCCTCGGGAACGGACTTCagtATCAATTTTATACGCTGGTACCGCCAGGCTCCAG<br>GGAAGCAGCGCGAGTTCGTCGCAGGATTTACTGCGACTGgTAACACAAACTATGCAGACTCC<br>AtgAAGGGGCGATTCACCATCTCCAG<u>AGACAACACCAAGAACGCGGT</u>GTATCTGCAAATAGA<br>CAGCCTGAAACCTGAGGACACGGCCGTGTATTACTGCTATATGTTG<u>GAAAAGT</u>GGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A20 | 105 | GAGGTGcAGCTGGTGGAGTCTGGGGGAGGCGTGGTGCAGCCTGGGGGGTCTCTACGTCTCTC<br>CTGCGCAGCCTCGGGAACGGACTTCAGTATCAATTTATGAGCTGGTTCGCCAGGCTCCAG<br>GGAAGGGTCTGGAGTGGGTCGCAGGATTTACTGCGACTGGTAACACAAACTATGCAGACTCC<br>GTTAAGGGGCGATTCACCATCTCCAGAGACAACGCAAAGAACACCCTGTATCTGCAAATGAA<br>TAGCCTGCGTCCTGAGGACACGGCCGTGTATTACTGCTATATGTTGGACAAGTGGGGCCAGG<br>GGACCCAGGTCACCGTCTCCTCAGCGGCCGCAGAACAAAAACTCATCTCAGAAGAGGATCTG<br>AATGGGGCCGCACATCACCACCATCACCATGGGAGCTAG |
| A21 | 106 | GAGGTGcAGCTGGTGGAGTCTGGGGGAGGCGTGGTGCAGCCTGGGGGGTCTCTACGTCTCTC<br>CTGCGCAGCCTCGGGAACGGACTTCAGTATCAATTTTATACGCTGGTTCGCCAGGCTCCAG<br>GGAAGCAGCGCGAGTTCGTCGCAGGATTTACTGCGACTGGTAACACAAACTATGCAGACTCC<br>GTTAAGGGGCGATTCACCATCTCCAGAGACAACGCAAAGAACACCCTGTATCTGCAAATGAA<br>TAGCCTGCGTCCTGAGGACACGGCCGTGTATTACTGC<u>TATATGTTGGACAAGT</u>GGGGCCAGG |

| | | |
|---|---|---|
| | | GGACCCAGGTCACCGTCTCCTCAGCGGCCGCAGAACAAAAACTCATCTCAGAAGAGGATCTGAATGGGGCCGCACATCACCACCATCACCATGGGAGCTAG |
| A22 | 107 | GAGGTGcAGCTGGTGGAGTCTGGGGGAGGCGTGGTGCAGCCTGGGGGGTCTCTACGTCTCTCCTGCGCAGCCTCGGGAACGGACTTCAGTATCAATTTTATGCATTGGGTTCGCCAGGCTCCAGGGAAGGGTCTGGAGTGGGTCGCAGGATTTACTGCGACTGGTAACACAAACTATGCAGACTCCGTTAAGGGGCGATTCACCATCTCCAGAGACAACGCAAAGAACACCCTGTATCTGCAAATGAATAGCCTGCGTCCTGAGGACACGGCCGTGTATTACTGCTATATGTTGGACAAGTGGGGCCAGGGGACCCAGGTCACCGTCTCCTCAGCGGCCGCAGAACAAAAACTCATCTCAGAAGAGGATCTGAATGGGGCCGCACATCACCACCATCACCATGGGAGCTAG |
| A23 | 108 | GAGGTGcAGCTGGTGGAGTCTGGGGGAGGCGTGGTGCAGCCTGGGGGGTCTCTACGTCTCTCCTGCGCAGCCTCGGGAACGGACTTCAGTATCAATTTTATGAGCTGGGTTCGCCAGGCTCCAGGGAAGCAGCGCGAGTTCGTCGCAGGATTTACTGCGACTGGTAACACAAACTATGCAGACTCCGTTAAGGGGCGATTCACCATCTCCAGAGACAACGCAAAGAACACCCTGTATCTGCAAATGAATAGCCTGCGTCCTGAGGACACGGCCGTGTATTACTGCTATATGTTGGACAAGTGGGGCCAGGGGACCCAGGTCACCGTCTCCTCAGCGGCCGCAGAACAAAAACTCATCTCAGAAGAGGATCTGAATGGGGCCGCACATCACCACCATCACCATGGGAGCTAG |
| A24 | 109 | GAGGTGcAGCTGGTGGAGTCTGGGGGAGGCGTGGTGCAGCCTGGGGGGTCTCTACGTCTCTCCTGCGCAGCCTCGGGAACGGACTTCAGTATCAATTTTATACGCTGGGTTCGCCAGGCTCCAGGGAAGGGTCTGGAGTGGGTCGCAGGATTTACTGCGACTGGTAACACAAACTATGCAGACTCCGTTAAGGGGCGATTCACCATCTCCAGAGACAACGCAAAGAACACCCTGTATCTGCAAATGAATAGCCTGCGTCCTGAGGACACGGCCGTGTATTACTGCTATATGTTGGACAAGTGGGGCCAGGGGACCCAGGTCACCGTCTCCTCAGCGGCCGCAGAACAAAAACTCATCTCAGAAGAGGATCTGAATGGGGCCGCACATCACCACCATCACCATGGGAGCTAG |
| A25 | 110 | GAGGTGcAGCTGGTGGAGTCTGGGGGAGGCGTGGTGCAGCCTGGGGGGTCTCTACGTCTCTCCTGCGCAGCCTCGGGAACGGACTTCAGTATCAATTTTATACATTGGGTTCGCCAGGCTCCAGGGAAGGGTCTGGAGTGGGTCGCAGGATTTACTGCGACTGGTAACACAAACTATGCAGACTCCGTTAAGGGGCGATTCACCATCTCCAGAGACAACGCAAAGAACACCCTGTATCTGCAAATGAATAGCCTGCGTCCTGAGGACACGGCCGTGTATTACTGCTATATGTTGGACAAGTGGGGCCAGGGGACCCAGGTCACCGTCTCCTCAGCGGCCGCAGAACAAAAACTCATCTCAGAAGAGGATCTGAATGGGGCCGCACATCACCACCATCACCATGGGAGCTAG |

The invention claimed is:

1. A VHH molecule of formula FR1-CDR1-FR2-CDR2-FR3-CDR3-FR4, wherein said VHH molecule binds both a human and a non-human animal transferrin receptor (TfR) with an affinity (Kd) comprised between 0.1 nM and 10 μM, optionally conjugated to at least one molecule or scaffold, wherein the CDR1 sequence, the CDR2 sequence, and the CDR3 sequence comprise SEQ ID NOs: 1, 2 and 3, respectively; or SEQ ID NOs: 5, 6 and 7, respectively; or SEQ ID NOs: 9, 10 and 11, respectively; or SEQ ID NOs: 13, 14 and 15, respectively; SEQ ID NOs: 17, 2 and 3, respectively; or SEQ ID NOs: 19, 2 and 3, respectively; or SEQ ID NOs: 1, 21 and 3, respectively; or SEQ ID NOs: 1, 23 and 3, respectively; or SEQ ID NOs: 1, 2 and 25, respectively; or SEQ ID NOs: 1, 2 and 27, respectively; or SEQ ID NOs: 1, 2 and 29, respectively; or SEQ ID NOs: 1, 2 and 31, respectively; or SEQ ID NOs: 1, 2 and 33, respectively; or SEQ ID NOs: 67, 2 and 3, respectively; or SEQ ID NOs: 69, 2 and 3, respectively; or SEQ ID NOs: 1, 71 and 3, respectively; or SEQ ID NOs: 1, 73 and 3, respectively; or SEQ ID NOs: 1, 75 and 3, respectively; or SEQ ID NOs: 1, 2 and 77, respectively; or SEQ ID NOs: 1, 2 and 79, respectively; or SEQ ID NOs: 1, 2 and 81, respectively; or SEQ ID NOs: 1, 2 and 83, respectively; or SEQ ID NOs: 1, 2 and 85, respectively.

2. The VHH molecule of claim 1, wherein said VHH can cross the blood brain barrier.

3. The VHH molecule of claim 1, wherein binding of said molecule to a human TfR does not compete with binding of transferrin.

4. The VHH molecule of claim 1, said VHH binding both a human and a rodent TfR1.

5. The VHH molecular of claim 1, which comprises:
a) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMLDKWGQGTQV TVSS (AAAEQKLISEEDLNGAAHHHHHHGS)$_x$, (SEQ ID NO: 4), wherein x is 0 or 1;
b) EVOLVESGGGVVQPGGSLRLSCAASGEIFS-INFMRWYRQAPGKQREWVAG FTRDGSTNYPD-SAKGRFTISRDNAKNTVYLQIDSLKPED- TAVYYCYMLDTWGQGTQVT VSS (AAAEQKLISEEDLNGAAHHHHHHGS)$_x$ (SEQ ID NO: 8), wherein x is 0 or 1;

c) EVOLVESGGGLVQPGGSLRLSCTASGG-PIEQYPMGWFRRAPGKERELVAS ISRSGDGTYYAISSVKGRFTISRDNAE-NTVFLQMNSLKPDDTAVYYCGAGINPTKIWGQ GTQVTVSS(AAAEQKLISEEDLN-GAAHHHHHHGS)$_x$ (SEQ ID NO: 12), wherein x is 0 or 1;

d) EVOLVESGGGEVQPGGSLKLSCVASGTDFS-INFVRWYRQRPGKQREWVA GFTANGDTNYPDSMKGRFTISRD-NAKNTVYLQINSLKSED-TAVYYCYMLDNWGQGTQ VTVSS(AAAEQKLI-SEEDLNGAAHHHHHHGS)$_x$ (SEQ ID NO: 16), wherein x is 0 or 1;

e) EVOLVESGGGVVQPGGSLKLSCVASGADFSIN-FIRWYRQAPGKQREFVA GFTATGNTNY-ADSMKGRFTISRDNTKNAVYLQIDSLKPED-TAVYYCYMLDKWGQGTQ VTVSS (AAAEQKLISEEDLNGAAHHHHHHGS)$_x$ (SEQ ID NO: 18), wherein x is 0 or 1;

f) EVQLVESGGGVVQPGGSLKLSCVASGTAFSIN-FIRWYRQAPGKQREFVAG FTATGNTNY-ADSMKGRFTISRDNTKNAVYLQIDSLKPED-TAVYYCYMLDKWGQGTQV TVSS (AAAEQKLISEEDLNGAAHHHHHHGS)$_x$ (SEQ ID NO: 20), wherein x is 0 or 1;

g) EVOLVESGGGVVQPGGSLKLSCVASGTDFSIN-FIRWYRQAPGKQREFVAG FTAAGNTNY-ADSMKGRFTISRDNTKNAVYLQIDSLKPED-TAVYYCYMLDKWGQGTQV TVSS (AAAEQKLISEEDLNGAAHHHHHHGS)$_x$ (SEQ ID NO: 22), wherein x is 0 or 1;

h) EVOLVESGGGVVQPGGSLKLSCVASGTDFSIN-FIRWYRQAPGKQREFVAG FTATGATNY-ADSMKGRFTISRDNTKNAVYLQIDSLKPED-TAVYYCYMLDKWGQGTQV TVSS (AAAEQKLISEEDLNGAAHHHHHHGS)$_x$ (SEQ ID NO: 24), wherein x is 0 or 1;

i) EVQLVESGGGVVQPGGSLKLSCVASGTDFSIN-FIRWYRQAPGKQREFVAG FTATGNTNY-ADSMKGRFTISRDNTKNAVYLQIDSLKPED-TAVYYCAMLDKWGQGTQV TVSS (AAAEQKLISEEDLNGAAHHHHHHGS)$_x$ (SEQ ID NO: 26), wherein x is 0 or 1;

j) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYALDKWGQGTQVT VSS (AAAEQKLISEEDLNGAAHHHHHHGS)$_x$ (SEQ ID NO: 28), wherein x is 0 or 1;

k) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMADKWGQGTQV TVSS (AAAEQKLISEEDLNGAAHHHHHHGS)$_x$ (SEQ ID NO: 30), wherein x is 0 or 1;

l) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMLAKWGQGTQV TVSS (AAAEQKLISEEDLNGAAHHHHHHGS)$_x$ (SEQ ID NO: 32), wherein x is 0 or 1;

m) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMLDAWGQGTQV TVSS (AAAEQKLISEEDLNGAAHHHHHHGS)$_x$ (SEQ ID NO: 34), wherein x is 0 or 1.

6. The VHH molecular of claim 1, which comprises:

a) EVOLVESGGGVVQPGGSLKLSCVASGTDFSLN-FIRWYRQAPGKQREFVA GFTATGNTNY-ADSMKGRFTISRDNTKNAVYLQIDSLKPED-TAVYYCYMLDKWGQGTQ VTVSS (AAAEQKLISEEDLNGAAHHHHHHGS)$_x$ (SEQ ID NO: 68), wherein x is 0 or 1;

b) EVOLVESGGGVVQPGGSLKLSCVASGTDFS-INYIRWYRQAPGKQREFVA GFTATGNTNY-ADSMKGRFTISRDNTKNAVYLQIDSLKPED-TAVYYCYMLDKWGQGTQ VTVSS (AAAEQKLISEEDLNGAAHHHHHHGS)$_x$ (SEQ ID NO: 70), wherein x is 0 or 1;

c) EVOLVESGGGVVQPGGSLKLSCVASGTDFSIN-FIRWYRQAPGKQREFVAG ITATGNTNY-ADSMKGRFTISRDNTKNAVYLQIDSLKPED-TAVYYCYMLDKWGQGTQVT VSS (AAAEQKLISEEDLNGAAHHHHHHGS)$_x$ (SEQ ID NO: 72), wherein x is 0 or 1;

d) EVOLVESGGGVVQPGGSLKLSCVASGTDFSIN-FIRWYRQAPGKQREFVAG FSATGNTNY-ADSMKGRFTISRDNTKNAVYLQIDSLKPED-TAVYYCYMLDKWGQGTQV TVSS (AAAEQKLISEEDLNGAAHHHHHHGS)$_x$ (SEQ ID NO: 74), wherein x is 0 or 1;

e) EVOLVESGGGVVQPGGSLKLSCVASGTDFSIN-FIRWYRQAPGKQREFVAG FTATGNSNY-ADSMKGRFTISRDNTKNAVYLQIDSLKPED-TAVYYCYMLDKWGQGTQV TVSS (AAAEQKLISEEDLNGAAHHHHHHGS)$_x$ (SEQ ID NO: 76), wherein x is 0 or 1;

f) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCFMLDKWGQGTQVT VSS (AAAEQKLISEEDLNGAAHHHHHHGS)$_x$ (SEQ ID NO: 78), wherein x is 0 or 1;

g) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYILDKWGQGTQVT VSS (AAAEQKLISEEDLNGAAHHHHHHGS)$_x$ (SEQ ID NO: 80), wherein x is 0 or 1;

h) EVQLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMIDKWGQGTQVT VSS (AAAEQKLISEEDLNGAAHHHHHHGS)$_x$ (SEQ ID NO: 82), wherein x is 0 or 1;

i) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMVDKWGQGTQV TVSS (AAAEQKLISEEDLNGAAHHHHHHGS)$_x$ (SEQ ID NO: 84), wherein x is 0 or 1;

j) EVOLVESGGGVVQPGGSLKLSCVASGTDFSIN-FIRWYRQAPGKQREFVAG FTATGNTNY-ADSMKGRFTISRDNTKNAVYLQIDSLKPED-TAVYYCYMLEKWGQGTQV TVSS (AAAEQKLISEEDLNGAAHHHHHHGS)$_x$ (SEQ ID NO: 86), wherein x is 0 or 1;

k) EVOLVESGGGVVQPGGSLRLSCAASGTDFS-INFMSWVRQAPGKGLEWVA GFTATGNTNY-

ADSVKGRFTISRDNAKNTLYLQMNSLRPED-TAVYYCYMLDKWGQGTQ VTVSS (AAAEQKLISEEDLNGAAHHHHHHGS)$_x$ (SEQ ID NO: 87), wherein x is 0 or 1;

l) EVOLVESGGGVVQPGGSLRLSCAASGTDFSIN-FIRWVRQAPGKQREFVAG FTATGNTNY-ADSVKGRFTISRDNAKNTLYLQMNSLRPED-TAVYYCYMLDKWGQGTQV TVSS (AAAEQKLISEEDLNGAAHHHHHHGS)$_x$ (SEQ ID NO: 88), wherein x is 0 or 1;

m) EVOLVESGGGVVQPGGSLRLSCAASGTDFS-INFMHWVRQAPGKGLEWV AGFTATGNTNY-ADSVKGRFTISRDNAKNTLYLQMNSLRPED-TAVYYCYMLDKWGQGT QVTVSS (AAAEQKLISEEDLNGAAHHHHHHGS)$_x$ (SEQ ID NO: 89), wherein x is 0 or 1;

n) EVOLVESGGGVVQPGGSLRLSCAASGTDES-INFMSWVRQAPGKQREFVA GFTATGNTNY-ADSVKGRFTISRDNAKNTLYLQMNSLRPED-TAVYYCYMLDKWGQGTQ VTVSS (AAAEQKLISEEDLNGAAHHHHHHGS)$_x$ (SEQ ID NO: 90), wherein x is 0 or 1;

o) EVOLVESGGGVVQPGGSLRLSCAASGTDFSIN-FIRWVRQAPGKGLEWV AGFTATGNTNY-ADSVKGRFTISRDNAKNTLYLQMNSLRPED-TAVYYCYMLDKWGQGT QVTVSS (AAAEQKLISEEDLNGAAHHHHHHGS)$_x$ (SEQ ID NO: 91), wherein x is 0 or 1;

p) EVQLVESGGGVVQPGGSLRLSCAASGTDESIN-FIHWVRQAPGKGLEWVA GFTATGNTNY-ADSVKGRFTISRDNAKNTLYLQMNSLRPED-TAVYYCYMLDKWGQGTQ VTVSS (AAAEQKLISEEDLNGAAHHHHHHGS)$_x$ (SEQ ID NO: 92), wherein x is 0 or 1.

7. The VHH molecule of claim 1, which is humanized.

8. The VHH molecule of claim 1, said VHH being conjugated to at least one molecule.

9. A chimeric agent comprising one or more VHH of claim 1 conjugated to at least one molecule or scaffold.

10. The chimeric agent of claim 9, wherein the at least one molecule is an active compound, a virus or virus-like particle, or a stabilizing group.

11. The chimeric agent of claim 9, which comprises a VHH, a stabilizing group and an active compound, in any order.

12. A pharmaceutical composition comprising a chimeric agent of claim 9.

13. A method of making a chimeric agent, comprising conjugating one or more VHH of claim 1 to at least one molecule, covalently or non-covalently.

14. The chimeric agent of claim 10, wherein the active compound is a therapeutic, diagnostic or imaging agent.

* * * * *

SEQUENCE LISTING

<160> NUMBER OF SEQ ID NOS: 112

<210> SEQ ID NO 1
<211> LENGTH: 8
<212> TYPE: PRT
<213> ORGANISM: Artificial Sequence
<220> FEATURE:
<223> OTHER INFORMATION: Protein or domain

<400> SEQUENCE: 1

Gly Thr Asp Phe Ser Ile Asn Phe
1               5

<210> SEQ ID NO 2
<211> LENGTH: 7
<212> TYPE: PRT
<213> ORGANISM: artificial
<220> FEATURE:
<223> OTHER INFORMATION: Protein or domain

<400> SEQUENCE: 2

Phe Thr Ala Thr Gly Asn Thr
1               5

<210> SEQ ID NO 3
<211> LENGTH: 5
<212> TYPE: PRT
<213> ORGANISM: artificial
<220> FEATURE:
<223> OTHER INFORMATION: Protein or domain

<400> SEQUENCE: 3

```
Tyr Met Leu Asp Lys
1               5

<210> SEQ ID NO 4
<211> LENGTH: 136
<212> TYPE: PRT
<213> ORGANISM: artificial
<220> FEATURE:
<223> OTHER INFORMATION: Protein or domain

<400> SEQUENCE: 4

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 5
<211> LENGTH: 8
<212> TYPE: PRT
<213> ORGANISM: artificial
<220> FEATURE:
<223> OTHER INFORMATION: Protein or domain

<400> SEQUENCE: 5

Gly Glu Ile Phe Ser Ile Asn Phe
1               5

<210> SEQ ID NO 6
<211> LENGTH: 7
<212> TYPE: PRT
<213> ORGANISM: artificial
<220> FEATURE:
<223> OTHER INFORMATION: Protein or domain

<400> SEQUENCE: 6

Phe Thr Arg Asp Gly Ser Thr
1               5

<210> SEQ ID NO 7
<211> LENGTH: 5
<212> TYPE: PRT
<213> ORGANISM: artificial
<220> FEATURE:
<223> OTHER INFORMATION: Protein or domain

<400> SEQUENCE: 7

Tyr Met Leu Asp Thr
1               5
```

<210> SEQ ID NO 8
<211> LENGTH: 136
<212> TYPE: PRT
<213> ORGANISM: artificial
<220> FEATURE:
<223> OTHER INFORMATION: Protein or domain

<400> SEQUENCE: 8

Glu Val Gln Leu Val Glu Ser Gly Gly Gly Val Val Gln Pro Gly Gly
1               5                   10                  15

Ser Leu Arg Leu Ser Cys Ala Ala Ser Gly Glu Ile Phe Ser Ile Asn
            20                  25                  30

Phe Met Arg Trp Tyr Arg Gln Ala Pro Gly Lys Gln Arg Glu Trp Val
        35                  40                  45

Ala Gly Phe Thr Arg Asp Gly Ser Thr Asn Tyr Pro Asp Ser Ala Lys
    50                  55                  60

Gly Arg Phe Thr Ile Ser Arg Asp Asn Ala Lys Asn Thr Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Thr Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 9
<211> LENGTH: 8
<212> TYPE: PRT
<213> ORGANISM: artificial
<220> FEATURE:
<223> OTHER INFORMATION: Protein or domain

<400> SEQUENCE: 9

Gly Gly Pro Ile Glu Gln Tyr Pro
1               5

<210> SEQ ID NO 10
<211> LENGTH: 9
<212> TYPE: PRT
<213> ORGANISM: artificial
<220> FEATURE:
<223> OTHER INFORMATION: Protein or domain

<400> SEQUENCE: 10

Ile Ser Arg Ser Gly Asp Gly Thr Tyr
1               5

<210> SEQ ID NO 11
<211> LENGTH: 9
<212> TYPE: PRT
<213> ORGANISM: artificial
<220> FEATURE:
<223> OTHER INFORMATION: Protein or domain

<400> SEQUENCE: 11

Gly Ala Gly Ile Asn Pro Thr Lys Ile
1               5

<210> SEQ ID NO 12

<211> LENGTH: 142
<212> TYPE: PRT
<213> ORGANISM: artificial
<220> FEATURE:
<223> OTHER INFORMATION: Protein or domain

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Thr Ala Ser Gly Pro Ile Glu Gln Tyr
            20                  25                  30

Pro Met Gly Trp Phe Arg Arg Ala Pro Gly Lys Glu Arg Glu Leu Val
                35                  40                  45

Ala Ser Ile Ser Arg Ser Gly Asp Gly Thr Tyr Tyr Ala Ile Ser Ser
    50                  55                  60

Val Lys Gly Arg Phe Thr Ile Ser Arg Asp Asn Ala Glu Asn Thr Val
65                  70                  75                  80

Phe Leu Gln Met Asn Ser Leu Lys Pro Asp Asp Thr Ala Val Tyr Tyr
                85                  90                  95

Cys Gly Ala Gly Ile Asn Pro Thr Lys Ile Trp Gly Gln Gly Thr Gln
            100                 105                 110

Val Thr Val Ser Ser Ala Ala Ala Glu Gln Lys Leu Ile Ser Glu Glu
        115                 120                 125

Asp Leu Asn Gly Ala Ala His His His His His His Gly Ser
    130                 135                 140

<210> SEQ ID NO 13
<211> LENGTH: 8
<212> TYPE: PRT
<213> ORGANISM: artificial
<220> FEATURE:
<223> OTHER INFORMATION: Protein or domain

<400> SEQUENCE: 13

Gly Thr Asp Phe Ser Ile Asn Phe
1               5

<210> SEQ ID NO 14
<211> LENGTH: 7
<212> TYPE: PRT
<213> ORGANISM: artificial
<220> FEATURE:
<223> OTHER INFORMATION: Protein or domain

<400> SEQUENCE: 14

Phe Thr Ala Asn Gly Asp Thr
1               5

<210> SEQ ID NO 15
<211> LENGTH: 5
<212> TYPE: PRT
<213> ORGANISM: artificial
<220> FEATURE:
<223> OTHER INFORMATION: Protein or domain

<400> SEQUENCE: 15

Tyr Met Leu Asp Asn
1               5

<210> SEQ ID NO 16
<211> LENGTH: 136
<212> TYPE: PRT
<213> ORGANISM: artificial

<220> FEATURE:
<223> OTHER INFORMATION: Protein or domain

<400> SEQUENCE: 16

Glu Val Gln Leu Val Glu Ser Gly Gly Gly Val Gln Pro Gly Gly
1               5                   10                  15

Ser Leu Lys Leu Ser Cys Val Ala Ser Gly Thr Asp Phe Ser Ile Asn
            20                  25                  30

Phe Val Arg Trp Tyr Arg Gln Arg Pro Gly Lys Gln Arg Glu Trp Val
        35                  40                  45

Ala Gly Phe Thr Ala Asn Gly Asp Thr Asn Tyr Pro Asp Ser Met Lys
    50                  55                  60

Gly Arg Phe Thr Ile Ser Arg Asp Asn Ala Lys Asn Thr Val Tyr Leu
65                  70                  75                  80

Gln Ile Asn Ser Leu Lys Ser Glu Asp Thr Ala Val Tyr Tyr Cys Tyr
                85                  90                  95

Met Leu Asp Asn Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His Gly Ser
    130                 135

<210> SEQ ID NO 17
<211> LENGTH: 8
<212> TYPE: PRT
<213> ORGANISM: artificial
<220> FEATURE:
<223> OTHER INFORMATION: Protein or domain

<400> SEQUENCE: 17

Gly Ala Asp Phe Ser Ile Asn Phe
1               5

<210> SEQ ID NO 18
<211> LENGTH: 136
<212> TYPE: PRT
<213> ORGANISM: artificial
<220> FEATURE:
<223> OTHER INFORMATION: Protein or domain

<400> SEQUENCE: 18

Glu Val Gln Leu Val Glu Ser Gly Gly Gly Val Val Gln Pro Gly Gly
1               5                   10                  15

Ser Leu Lys Leu Ser Cys Val Ala Ser Gly Ala Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

```
His His His His His Gly Ser
    130             135

<210> SEQ ID NO 19
<211> LENGTH: 8
<212> TYPE: PRT
<213> ORGANISM: artificial
<220> FEATURE:
<223> OTHER INFORMATION: Protein or domain

<400> SEQUENCE: 19

Gly Thr Ala Phe Ser Ile Asn Phe
1               5

<210> SEQ ID NO 20
<211> LENGTH: 136
<212> TYPE: PRT
<213> ORGANISM: artificial
<220> FEATURE:
<223> OTHER INFORMATION: Protein or domain

<400> SEQUENCE: 20

Glu Val Gln Leu Val Glu Ser Gly Gly Gly Val Val Gln Pro Gly Gly
1               5                   10                  15

Ser Leu Lys Leu Ser Cys Val Ala Ser Gly Thr Ala Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His Gly Ser
    130             135

<210> SEQ ID NO 21
<211> LENGTH: 7
<212> TYPE: PRT
<213> ORGANISM: artificial
<220> FEATURE:
<223> OTHER INFORMATION: Protein or domain

<400> SEQUENCE: 21

Phe Thr Ala Ala Gly Asn Thr
1               5

<210> SEQ ID NO 22
<211> LENGTH: 136
<212> TYPE: PRT
<213> ORGANISM: artificial
<220> FEATURE:
<223> OTHER INFORMATION: Protein or domain

<400> SEQUENCE: 22

Glu Val Gln Leu Val Glu Ser Gly Gly Gly Val Val Gln Pro Gly Gly
1               5                   10                  15
```

```
Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Ala Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
        130                 135

<210> SEQ ID NO 23
<211> LENGTH: 7
<212> TYPE: PRT
<213> ORGANISM: artificial
<220> FEATURE:
<223> OTHER INFORMATION: Protein or domain

<400> SEQUENCE: 23

Phe Thr Ala Thr Gly Ala Thr
1               5

<210> SEQ ID NO 24
<211> LENGTH: 136
<212> TYPE: PRT
<213> ORGANISM: artificial
<220> FEATURE:
<223> OTHER INFORMATION: Protein or domain

<400> SEQUENCE: 24

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Ala Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
        130                 135

<210> SEQ ID NO 25
<211> LENGTH: 5
<212> TYPE: PRT
<213> ORGANISM: artificial
```

```
<220> FEATURE:
<223> OTHER INFORMATION: Protein or domain

<400> SEQUENCE: 25

Ala Met Leu Asp Lys
1               5

<210> SEQ ID NO 26
<211> LENGTH: 136
<212> TYPE: PRT
<213> ORGANISM: artificial
<220> FEATURE:
<223> OTHER INFORMATION: Protein or domain

<400> SEQUENCE: 26

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
                20                  25                  30

Phe Ile Arg Trp Tyr Arg Gln Ala Pro Gly Lys Gln Arg Glu Phe Val
            35                  40                  45

Ala Gly Phe Thr Ala Thr Gly Asn Thr Asn Tyr Ala Asp Ser Met Lys
        50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Ala
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 27
<211> LENGTH: 5
<212> TYPE: PRT
<213> ORGANISM: artificial
<220> FEATURE:
<223> OTHER INFORMATION: Protein or domain

<400> SEQUENCE: 27

Tyr Ala Leu Asp Lys
1               5

<210> SEQ ID NO 28
<211> LENGTH: 136
<212> TYPE: PRT
<213> ORGANISM: artificial
<220> FEATURE:
<223> OTHER INFORMATION: Protein or domain

<400> SEQUENCE: 28

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
                20                  25                  30

Phe Ile Arg Trp Tyr Arg Gln Ala Pro Gly Lys Gln Arg Glu Phe Val
            35                  40                  45

Ala Gly Phe Thr Ala Thr Gly Asn Thr Asn Tyr Ala Asp Ser Met Lys
        50                  55                  60
```

```
Gly Arg Phe Thr Ile Ser Arg Asp Asn Thr Lys Asn Ala Val Tyr Leu
 65                  70                  75                  80

Gln Ile Asp Ser Leu Lys Pro Glu Asp Thr Ala Val Tyr Tyr Cys Tyr
                 85                  90                  95

Ala Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 29
<211> LENGTH: 5
<212> TYPE: PRT
<213> ORGANISM: artificial
<220> FEATURE:
<223> OTHER INFORMATION: Protein or domain

<400> SEQUENCE: 29

Tyr Met Ala Asp Lys
1               5

<210> SEQ ID NO 30
<211> LENGTH: 136
<212> TYPE: PRT
<213> ORGANISM: artificial
<220> FEATURE:
<223> OTHER INFORMATION: Protein or domain

<400> SEQUENCE: 30

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
                20                  25                  30

Phe Ile Arg Trp Tyr Arg Gln Ala Pro Gly Lys Gln Arg Glu Phe Val
            35                  40                  45

Ala Gly Phe Thr Ala Thr Gly Asn Thr Asn Tyr Ala Asp Ser Met Lys
 50                  55                  60

Gly Arg Phe Thr Ile Ser Arg Asp Asn Thr Lys Asn Ala Val Tyr Leu
 65                  70                  75                  80

Gln Ile Asp Ser Leu Lys Pro Glu Asp Thr Ala Val Tyr Tyr Cys Tyr
                 85                  90                  95

Met Ala Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 31
<211> LENGTH: 5
<212> TYPE: PRT
<213> ORGANISM: artificial
<220> FEATURE:
<223> OTHER INFORMATION: Protein or domain

<400> SEQUENCE: 31

Tyr Met Leu Ala Lys
1               5
```

```
<210> SEQ ID NO 32
<211> LENGTH: 136
<212> TYPE: PRT
<213> ORGANISM: artificial
<220> FEATURE:
<223> OTHER INFORMATION: Protein or domain

<400> SEQUENCE: 32

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Ala Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 33
<211> LENGTH: 5
<212> TYPE: PRT
<213> ORGANISM: artificial
<220> FEATURE:
<223> OTHER INFORMATION: Protein or domain

<400> SEQUENCE: 33

Tyr Met Leu Asp Ala
1               5

<210> SEQ ID NO 34
<211> LENGTH: 136
<212> TYPE: PRT
<213> ORGANISM: artificial
<220> FEATURE:
<223> OTHER INFORMATION: Protein or domain

<400> SEQUENCE: 34

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Ala Trp Gly Gln Gly Thr Gln Val Thr Val Ser Ser Ala
```

```
                100             105             110
Ala Ala Glu Gln Lys Leu Ile Ser Glu Glu Asp Leu Asn Gly Ala Ala
        115                 120             125

His His His His His His Gly Ser
        130                 135

<210> SEQ ID NO 35
<211> LENGTH: 25
<212> TYPE: PRT
<213> ORGANISM: artificial
<220> FEATURE:
<223> OTHER INFORMATION: Protein or domain

<400> SEQUENCE: 35

Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 36
<211> LENGTH: 25
<212> TYPE: PRT
<213> ORGANISM: artificial
<220> FEATURE:
<223> OTHER INFORMATION: Protein or domain

<400> SEQUENCE: 36

Glu Val Gln Leu Val Glu Ser Gly Gly Gly Val Val Gln Pro Gly Gly
1               5                   10                  15

Ser Leu Lys Leu Ser Cys Val Ala Ser
            20                  25

<210> SEQ ID NO 37
<211> LENGTH: 25
<212> TYPE: PRT
<213> ORGANISM: artificial
<220> FEATURE:
<223> OTHER INFORMATION: Protein or domain

<400> SEQUENCE: 37

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 38
<211> LENGTH: 25
<212> TYPE: PRT
<213> ORGANISM: artificial
<220> FEATURE:
<223> OTHER INFORMATION: Protein or domain

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 39
<211> LENGTH: 25
<212> TYPE: PRT
<213> ORGANISM: artificial
<220> FEATURE:
<223> OTHER INFORMATION: Protein or domain
```

```
<400> SEQUENCE: 39

Glu Val Gln Leu Val Glu Ser Gly Gly Gly Glu Val Gln Pro Gly Gly
1               5                   10                  15

Ser Leu Lys Leu Ser Cys Val Ala Ser
            20                  25

<210> SEQ ID NO 40
<211> LENGTH: 17
<212> TYPE: PRT
<213> ORGANISM: artificial
<220> FEATURE:
<223> OTHER INFORMATION: Protein or domain

<400> SEQUENCE: 40

Met Arg Trp Tyr Arg Gln Ala Pro Gly Lys Gln Arg Glu Leu Val Ala
1               5                   10                  15

Thr

<210> SEQ ID NO 41
<211> LENGTH: 17
<212> TYPE: PRT
<213> ORGANISM: artificial
<220> FEATURE:
<223> OTHER INFORMATION: Protein or domain

<400> SEQUENCE: 41

Ile Arg Trp Tyr Arg Gln Ala Pro Gly Lys Gln Arg Glu Phe Val Ala
1               5                   10                  15

Gly

<210> SEQ ID NO 42
<211> LENGTH: 17
<212> TYPE: PRT
<213> ORGANISM: artificial
<220> FEATURE:
<223> OTHER INFORMATION: Protein or domain

<400> SEQUENCE: 42

Met Arg Trp Tyr Arg Gln Ala Pro Gly Lys Gln Arg Glu Trp Val Ala
1               5                   10                  15

Gly

<210> SEQ ID NO 43
<211> LENGTH: 17
<212> TYPE: PRT
<213> ORGANISM: artificial
<220> FEATURE:
<223> OTHER INFORMATION: Protein or domain

<400> SEQUENCE: 43

Met Gly Trp Phe Arg Arg Ala Pro Gly Lys Glu Arg Glu Leu Val Ala
1               5                   10                  15

Ser

<210> SEQ ID NO 44
<211> LENGTH: 17
<212> TYPE: PRT
<213> ORGANISM: artificial
<220> FEATURE:
<223> OTHER INFORMATION: Protein or domain

<400> SEQUENCE: 44
```

```
Val Arg Trp Tyr Arg Gln Arg Pro Gly Lys Gln Arg Glu Trp Val Ala
1               5                   10                  15

Gly
```

```
<210> SEQ ID NO 45
<211> LENGTH: 38
<212> TYPE: PRT
<213> ORGANISM: artificial
<220> FEATURE:
<223> OTHER INFORMATION: Protein or domain

<400> SEQUENCE: 45

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
                20                  25                  30

Thr Ala Val Tyr Tyr Cys
            35
```

```
<210> SEQ ID NO 46
<211> LENGTH: 38
<212> TYPE: PRT
<213> ORGANISM: artificial
<220> FEATURE:
<223> OTHER INFORMATION: Protein or domain

<400> SEQUENCE: 46

Asn Tyr Ala Asp Ser Met Lys Gly Arg Phe Thr Ile Ser Arg Asp Asn
1               5                   10                  15

Thr Lys Asn Ala Val Tyr Leu Gln Ile Asp Ser Leu Lys Pro Glu Asp
                20                  25                  30

Thr Ala Val Tyr Tyr Cys
            35
```

```
<210> SEQ ID NO 47
<211> LENGTH: 38
<212> TYPE: PRT
<213> ORGANISM: artificial
<220> FEATURE:
<223> OTHER INFORMATION: Protein or domain

<400> SEQUENCE: 47

Asn Tyr Pro Asp Ser Ala Lys Gly Arg Phe Thr Ile Ser Arg Asp Asn
1               5                   10                  15

Ala Lys Asn Thr Val Tyr Leu Gln Ile Asp Ser Leu Lys Pro Glu Asp
                20                  25                  30

Thr Ala Val Tyr Tyr Cys
            35
```

```
<210> SEQ ID NO 48
<211> LENGTH: 38
<212> TYPE: PRT
<213> ORGANISM: artificial
<220> FEATURE:
<223> OTHER INFORMATION: Protein or domain

<400> SEQUENCE: 48

Tyr Ala Ile Ser Ser Val Lys Gly Arg Phe Thr Ile Ser Arg Asp Asn
1               5                   10                  15

Ala Glu Asn Thr Val Phe Leu Gln Met Asn Ser Leu Lys Pro Asp Asp
                20                  25                  30

Thr Ala Val Tyr Tyr Cys
```

<210> SEQ ID NO 49
<211> LENGTH: 38
<212> TYPE: PRT
<213> ORGANISM: artificial
<220> FEATURE:
<223> OTHER INFORMATION: Protein or domain

<400> SEQUENCE: 49

Asn Tyr Pro Asp Ser Met Lys Gly Arg Phe Thr Ile Ser Arg Asp Asn
1               5                   10                  15

Ala Lys Asn Thr Val Tyr Leu Gln Ile Asn Ser Leu Lys Ser Glu Asp
            20                  25                  30

Thr Ala Val Tyr Tyr Cys
        35

<210> SEQ ID NO 50
<211> LENGTH: 11
<212> TYPE: PRT
<213> ORGANISM: artificial
<220> FEATURE:
<223> OTHER INFORMATION: Protein or domain

<400> SEQUENCE: 50

Trp Gly Gln Gly Thr Gln Val Thr Val Ser Ser
1               5                   10

<210> SEQ ID NO 51
<211> LENGTH: 25
<212> TYPE: PRT
<213> ORGANISM: Artificial Sequence
<220> FEATURE:
<223> OTHER INFORMATION: Protein or domain

<400> SEQUENCE: 51

Ala Ala Ala Glu Gln Lys Leu Ile Ser Glu Glu Asp Leu Asn Gly Ala
1               5                   10                  15

Ala His His His His His His Gly Ser
            20                  25

<210> SEQ ID NO 52
<211> LENGTH: 411
<212> TYPE: DNA
<213> ORGANISM: Artificial Sequence
<220> FEATURE:
<223> OTHER INFORMATION: VHH coding sequence

<400> SEQUENCE: 52
gaggtgcagc tggtggagtc tgggggaggc gtggtgcagc tgggggggtc tctaaaactc      60
tcctgcgtag cctcgggaac ggacttcagt atcaatttta tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
caaatagaca gcctgaaacc tgaggacacg gccgtgtatt actgctatat gttggacaag     300
tggggccagg ggacccaggt caccgtctcc tcagcggccg cagaacaaaa actcatctca     360
gaagaggatc tgaatggggc cgcacatcac caccatcacc atgggagcta g              411

<210> SEQ ID NO 53
<211> LENGTH: 411
<212> TYPE: DNA
<213> ORGANISM: Artificial Sequence
<220> FEATURE:
<223> OTHER INFORMATION: VHH coding sequence

<400> SEQUENCE: 53

| | | | | | |
|---|---|---|---|---|---|
| gaggtgcagc | tggtggagtc | tgggggaggc | gtggtgcagc | ctggggggtc | tctaaaactc | 60 |
| tcctgcgtag | cctcgggagc | ggacttcagt | atcaatttta | tacgctggta | ccgccaggct | 120 |
| ccagggaagc | agcgcgagtt | cgtcgcagga | tttactgcga | ctggtaacac | aaactatgca | 180 |
| gactccatga | agggcgatt | caccatctcc | agagacaaca | ccaagaacgc | ggtgtatctg | 240 |
| caaatagaca | gcctgaaacc | tgaggacacg | gccgtgtatt | actgctatat | gttggacaag | 300 |
| tggggccagg | ggacccaggt | caccgtctcc | tcagcggccg | cagaacaaaa | actcatctca | 360 |
| gaagaggatc | tgaatggggc | cgcacatcac | caccatcacc | atgggagcta | g | 411 |

<210> SEQ ID NO 54
<211> LENGTH: 411
<212> TYPE: DNA
<213> ORGANISM: Artificial Sequence
<220> FEATURE:
<223> OTHER INFORMATION: VHH coding sequence

<400> SEQUENCE: 54

| | | | | | |
|---|---|---|---|---|---|
| gaggtgcagc | tggtggagtc | tgggggaggc | gtggtgcagc | ctggggggtc | tctaaaactc | 60 |
| tcctgcgtag | cctcgggaac | ggcgttcagt | atcaatttta | tacgctggta | ccgccaggct | 120 |
| ccagggaagc | agcgcgagtt | cgtcgcagga | tttactgcga | ctggtaacac | aaactatgca | 180 |
| gactccatga | agggcgatt | caccatctcc | agagacaaca | ccaagaacgc | ggtgtatctg | 240 |
| caaatagaca | gcctgaaacc | tgaggacacg | gccgtgtatt | actgctatat | gttggacaag | 300 |
| tggggccagg | ggacccaggt | caccgtctcc | tcagcggccg | cagaacaaaa | actcatctca | 360 |
| gaagaggatc | tgaatggggc | cgcacatcac | caccatcacc | atgggagcta | g | 411 |

<210> SEQ ID NO 55
<211> LENGTH: 411
<212> TYPE: DNA
<213> ORGANISM: Artificial Sequence
<220> FEATURE:
<223> OTHER INFORMATION: VHH coding sequence

<400> SEQUENCE: 55

| | | | | | |
|---|---|---|---|---|---|
| gaggtgcagc | tggtggagtc | tgggggaggc | gtggtgcagc | ctggggggtc | tctaaaactc | 60 |
| tcctgcgtag | cctcgggaac | ggacttcagt | atcaatttta | tacgctggta | ccgccaggct | 120 |
| ccagggaagc | agcgcgagtt | cgtcgcagga | tttactgcgg | cggtaacac | aaactatgca | 180 |
| gactccatga | agggcgatt | caccatctcc | agagacaaca | ccaagaacgc | ggtgtatctg | 240 |
| caaatagaca | gcctgaaacc | tgaggacacg | gccgtgtatt | actgctatat | gttggacaag | 300 |
| tggggccagg | ggacccaggt | caccgtctcc | tcagcggccg | cagaacaaaa | actcatctca | 360 |
| gaagaggatc | tgaatggggc | cgcacatcac | caccatcacc | atgggagcta | g | 411 |

<210> SEQ ID NO 56
<211> LENGTH: 411
<212> TYPE: DNA
<213> ORGANISM: Artificial Sequence
<220> FEATURE:
<223> OTHER INFORMATION: VHH coding sequence

<400> SEQUENCE: 56

| | | | | | |
|---|---|---|---|---|---|
| gaggtgcagc | tggtggagtc | tgggggaggc | gtggtgcagc | ctggggggtc | tctaaaactc | 60 |

```
tcctgcgtag cctcgggaac ggacttcagt atcaattta tacgctggta ccgccaggct    120
ccagggaagc agcgcgagtt cgtcgcagga tttactgcga ctggtgcgac aaactatgca    180
gactccatga agggggcgatt caccatctcc agagacaaca ccaagaacgc ggtgtatctg   240
caaatagaca gcctgaaacc tgaggacacg gccgtgtatt actgctatat gttggacaag   300
tggggccagg ggacccaggt caccgtctcc tcagcggccg cagaacaaaa actcatctca   360
gaagaggatc tgaatggggc cgcacatcac caccatcacc atgggagcta g            411
```

<210> SEQ ID NO 57
<211> LENGTH: 411
<212> TYPE: DNA
<213> ORGANISM: Artificial Sequence
<220> FEATURE:
<223> OTHER INFORMATION: VHH coding sequence

<400> SEQUENCE: 57

```
gaggtgcagc tggtggagtc tgggggaggc gtggtgcagc ctgggggggtc tctaaaactc    60 tcctgcgtag cctcgggaac ggacttcagt atcaattta tacgctggta ccgccaggct    120
ccagggaagc agcgcgagtt cgtcgcagga tttactgcga ctggtaacac aaactatgca    180
gactccatga agggggcgatt caccatctcc agagacaaca ccaagaacgc ggtgtatctg   240
caaatagaca gcctgaaacc tgaggacacg gccgtgtatt actgcgcgat gttggacaag   300
tggggccagg ggacccaggt caccgtctcc tcagcggccg cagaacaaaa actcatctca   360
gaagaggatc tgaatggggc cgcacatcac caccatcacc atgggagcta g            411
```

<210> SEQ ID NO 58
<211> LENGTH: 411
<212> TYPE: DNA
<213> ORGANISM: Artificial Sequence
<220> FEATURE:
<223> OTHER INFORMATION: VHH coding sequence

<400> SEQUENCE: 58

```
gaggtgcagc tggtggagtc tgggggaggc gtggtgcagc ctgggggggtc tctaaaactc    60 tcctgcgtag cctcgggaac ggacttcagt atcaattta tacgctggta ccgccaggct    120
ccagggaagc agcgcgagtt cgtcgcagga tttactgcga ctggtaacac aaactatgca    180
gactccatga agggggcgatt caccatctcc agagacaaca ccaagaacgc ggtgtatctg   240
caaatagaca gcctgaaacc tgaggacacg gccgtgtatt actgctatgc gttggacaag   300
tggggccagg ggacccaggt caccgtctcc tcagcggccg cagaacaaaa actcatctca   360
gaagaggatc tgaatggggc cgcacatcac caccatcacc atgggagcta g            411
```

<210> SEQ ID NO 59
<211> LENGTH: 411
<212> TYPE: DNA
<213> ORGANISM: Artificial Sequence
<220> FEATURE:
<223> OTHER INFORMATION: VHH coding sequence

<400> SEQUENCE: 59

```
gaggtgcagc tggtggagtc tgggggaggc gtggtgcagc ctgggggggtc tctaaaactc    60 tcctgcgtag cctcgggaac ggacttcagt atcaattta tacgctggta ccgccaggct    120
ccagggaagc agcgcgagtt cgtcgcagga tttactgcga ctggtaacac aaactatgca    180
gactccatga agggggcgatt caccatctcc agagacaaca ccaagaacgc ggtgtatctg   240
caaatagaca gcctgaaacc tgaggacacg gccgtgtatt actgctatat ggcggacaag   300
```

```
tggggccagg ggacccaggt caccgtctcc tcagcggccg cagaacaaaa actcatctca    360
gaagaggatc tgaatggggc cgcacatcac caccatcacc atgggagcta g             411
```

<210> SEQ ID NO 60
<211> LENGTH: 411
<212> TYPE: DNA
<213> ORGANISM: Artificial Sequence
<220> FEATURE:
<223> OTHER INFORMATION: VHH coding sequence

<400> SEQUENCE: 60

```
gaggtgcagc tggtggagtc tgggggaggc gtggtgcagc ctggggggtc tctaaaactc    60
tcctgcgtag cctcgggaac ggacttcagt atcaatttta tacgctggta ccgccaggct   120
ccagggaagc agcgcgagtt cgtcgcagga tttactgcga ctggtaacac aaactatgca   180
gactccatga agggccgatt caccatctcc agagacaaca ccaagaacgc ggtgtatctg   240
caaatagaca gcctgaaacc tgaggacacg gccgtgtatt actgctatat gttggcgaag   300
tggggccagg ggacccaggt caccgtctcc tcagcggccg cagaacaaaa actcatctca   360
gaagaggatc tgaatggggc cgcacatcac caccatcacc atgggagcta g            411
```

<210> SEQ ID NO 61
<211> LENGTH: 411
<212> TYPE: DNA
<213> ORGANISM: Artificial Sequence
<220> FEATURE:
<223> OTHER INFORMATION: VHH coding sequence

<400> SEQUENCE: 61

```
gaggtgcagc tggtggagtc tgggggaggc gtggtgcagc ctggggggtc tctaaaactc    60
tcctgcgtag cctcgggaac ggacttcagt atcaatttta tacgctggta ccgccaggct   120
ccagggaagc agcgcgagtt cgtcgcagga tttactgcga ctggtaacac aaactatgca   180
gactccatga agggccgatt caccatctcc agagacaaca ccaagaacgc ggtgtatctg   240
caaatagaca gcctgaaacc tgaggacacg gccgtgtatt actgctatat gttggacgcg   300
tggggccagg ggacccaggt caccgtctcc tcagcggccg cagaacaaaa actcatctca   360
gaagaggatc tgaatggggc cgcacatcac caccatcacc atgggagcta g            411
```

<210> SEQ ID NO 62
<211> LENGTH: 411
<212> TYPE: DNA
<213> ORGANISM: Artificial Sequence
<220> FEATURE:
<223> OTHER INFORMATION: VHH coding sequence

<400> SEQUENCE: 62

```
gaggtgcagc tggtggagtc tgggggaggc gtggtgcagc ctggggggtc tctgagactc    60
tcctgtgcag cctctggaga gatcttcagt atcaatttta tgcgctggta ccgccaggct   120
ccagggaagc agcgcgagtg gtcgcaggt tttactaggg atggaagcac aaactatcca   180
gactccgcga agggccgatt caccatctct agagacaacg ccaagaacac ggtgtatctg   240
caaatagaca gcctgaaacc tgaggacacg gccgtctatt attgttatat gttggacacc   300
tggggccagg ggacccaggt cactgtctcc tcagcggccg cagaacaaaa actcatctca   360
gaagaggatc tgaatggggc cgcacatcac caccatcacc atgggagcta g            411
```

<210> SEQ ID NO 63

```
<211> LENGTH: 429
<212> TYPE: DNA
<213> ORGANISM: Artificial Sequence
<220> FEATURE:
<223> OTHER INFORMATION: VHH coding sequence

<400> SEQUENCE: 63
gaggtgcagc tggtggagtc tgggggaggc ttggtgcagc ctggggttc tctgagactc      60 tcctgtacag cctctggagg ccccatcgag cagtatccca tgggctggtt ccgccgggcc    120
ccaggaaagg agcgtgaatt ggtagcaagt attagccgaa gtggagatgg cacatactat    180
gcaatctctt ccgtgaaggg ccgattcacc atctctagag acaacgccga gaacacggta    240
tttctgcaaa tgaacagcct gaaacctgac gacacggccg tttattactg tggggctggt    300
ataaacccaa ccaagatctg gggccagggg acccaggtca ccgtctcctc agcggccgca    360
gaacaaaaac tcatctcaga gaggatctg aatgggccg cacatcacca ccatcaccat     420
gggagctag                                                            429

<210> SEQ ID NO 64
<211> LENGTH: 411
<212> TYPE: DNA
<213> ORGANISM: Artificial Sequence
<220> FEATURE:
<223> OTHER INFORMATION: VHH coding sequence

<400> SEQUENCE: 64
gaggtgcagc tggtggagtc tgggggaggc gaggtgcagc tgggggggtc tctgaaactc     60
tcctgtgtag cctctggaac cgacttcagt atcaatttg tgcgctggta ccgtcagcgt    120
ccagggaagc agcgcgagtg ggtcgcagga tttactgcga atggtgatac aaactatcca    180
gactccatga aggggcgatt caccatttcc agagacaacg ccaagaatac ggtgtatcta    240
cagataaaca gcctgaaatc tgaggacacg gccgtctatt attgctatat gttagataat    300
tggggccagg ggacccaggt caccgtctcc tcagcggccg cagaacaaaa actcatctca    360
gaagaggatc tgaatggggc cgcacatcac caccatcacc atgggagcta g             411

<210> SEQ ID NO 65
<211> LENGTH: 31
<212> TYPE: DNA
<213> ORGANISM: Artificial Sequence
<220> FEATURE:
<223> OTHER INFORMATION: Primer

<400> SEQUENCE: 65
atatatgaat tcggctcggg acggaggacg c                                    31

<210> SEQ ID NO 66
<211> LENGTH: 36
<212> TYPE: DNA
<213> ORGANISM: Artificial Sequence
<220> FEATURE:
<223> OTHER INFORMATION: Primer

<400> SEQUENCE: 66
ttaattgtcg acagaactca ttgtcccaac cgtcac                               36

<210> SEQ ID NO 67
<211> LENGTH: 8
<212> TYPE: PRT
<213> ORGANISM: Artificial Sequence
<220> FEATURE:
<223> OTHER INFORMATION: Protein or domain
```

<400> SEQUENCE: 67

Gly Thr Asp Phe Ser Leu Asn Phe
1               5

<210> SEQ ID NO 68
<211> LENGTH: 136
<212> TYPE: PRT
<213> ORGANISM: Artificial Sequence
<220> FEATURE:
<223> OTHER INFORMATION: Protein or domain

<400> SEQUENCE: 68

Glu Val Gln Leu Val Glu Ser Gly Gly Gly Val Gln Pro Gly Gly
1               5                   10                  15

Ser Leu Lys Leu Ser Cys Val Ala Ser Gly Thr Asp Phe Ser Leu Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 69
<211> LENGTH: 8
<212> TYPE: PRT
<213> ORGANISM: Artificial Sequence
<220> FEATURE:
<223> OTHER INFORMATION: Protein or domain

<400> SEQUENCE: 69

Gly Thr Asp Phe Ser Ile Asn Tyr
1               5

<210> SEQ ID NO 70
<211> LENGTH: 136
<212> TYPE: PRT
<213> ORGANISM: Artificial Sequence
<220> FEATURE:
<223> OTHER INFORMATION: Protein or domain

<400> SEQUENCE: 70

Glu Val Gln Leu Val Glu Ser Gly Gly Gly Val Gln Pro Gly Gly
1               5                   10                  15

Ser Leu Lys Leu Ser Cys Val Ala Ser Gly Thr Asp Phe Ser Ile Asn
            20                  25                  30

Tyr Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu

```
                65                  70                  75                  80
Gln Ile Asp Ser Leu Lys Pro Glu Asp Thr Ala Val Tyr Tyr Cys Tyr
                    85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 71
<211> LENGTH: 7
<212> TYPE: PRT
<213> ORGANISM: Artificial Sequence
<220> FEATURE:
<223> OTHER INFORMATION: Protein or domain

<400> SEQUENCE: 71

Ile Thr Ala Thr Gly Asn Thr
1               5

<210> SEQ ID NO 72
<211> LENGTH: 136
<212> TYPE: PRT
<213> ORGANISM: Artificial Sequence
<220> FEATURE:
<223> OTHER INFORMATION: Protein or domain

<400> SEQUENCE: 72

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Ile Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 73
<211> LENGTH: 7
<212> TYPE: PRT
<213> ORGANISM: Artificial Sequence
<220> FEATURE:
<223> OTHER INFORMATION: Protein or domain

<400> SEQUENCE: 73

Phe Ser Ala Thr Gly Asn Thr
1               5

<210> SEQ ID NO 74
```

```
<211> LENGTH: 136
<212> TYPE: PRT
<213> ORGANISM: Artificial Sequence
<220> FEATURE:
<223> OTHER INFORMATION: Protein or domain

<400> SEQUENCE: 74

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Ser Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 75
<211> LENGTH: 7
<212> TYPE: PRT
<213> ORGANISM: Artificial Sequence
<220> FEATURE:
<223> OTHER INFORMATION: Protein or domain

<400> SEQUENCE: 75

Phe Thr Ala Thr Gly Asn Ser
1               5

<210> SEQ ID NO 76
<211> LENGTH: 136
<212> TYPE: PRT
<213> ORGANISM: Artificial Sequence
<220> FEATURE:
<223> OTHER INFORMATION: Protein or domain

<400> SEQUENCE: 76

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Ser Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110
```

```
Ala Ala Glu Gln Lys Leu Ile Ser Glu Glu Asp Leu Asn Gly Ala Ala
            115                 120                 125

His His His His His His Gly Ser
            130                 135

<210> SEQ ID NO 77
<211> LENGTH: 5
<212> TYPE: PRT
<213> ORGANISM: Artificial Sequence
<220> FEATURE:
<223> OTHER INFORMATION: Protein or domain

<400> SEQUENCE: 77

Phe Met Leu Asp Lys
1               5

<210> SEQ ID NO 78
<211> LENGTH: 136
<212> TYPE: PRT
<213> ORGANISM: Artificial Sequence
<220> FEATURE:
<223> OTHER INFORMATION: Protein or domain

<400> SEQUENCE: 78

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Phe
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
            115                 120                 125

His His His His His His Gly Ser
            130                 135

<210> SEQ ID NO 79
<211> LENGTH: 5
<212> TYPE: PRT
<213> ORGANISM: Artificial Sequence
<220> FEATURE:
<223> OTHER INFORMATION: Protein or domain

<400> SEQUENCE: 79

Tyr Ile Leu Asp Lys
1               5

<210> SEQ ID NO 80
<211> LENGTH: 136
<212> TYPE: PRT
<213> ORGANISM: Artificial Sequence
<220> FEATURE:
<223> OTHER INFORMATION: Protein or domain

<400> SEQUENCE: 80
```

```
Glu Val Gln Leu Val Glu Ser Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
            35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Ile Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
                115                 120                 125

His His His His His His Gly Ser
                130                 135
```

<210> SEQ ID NO 81
<211> LENGTH: 5
<212> TYPE: PRT
<213> ORGANISM: Artificial Sequence
<220> FEATURE:
<223> OTHER INFORMATION: Protein or domain

<400> SEQUENCE: 81

```
Tyr Met Ile Asp Lys
1               5
```

<210> SEQ ID NO 82
<211> LENGTH: 136
<212> TYPE: PRT
<213> ORGANISM: Artificial Sequence
<220> FEATURE:
<223> OTHER INFORMATION: Protein or domain

<400> SEQUENCE: 82

```
Glu Val Gln Leu Val Glu Ser Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
            35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Ile Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
                115                 120                 125

His His His His His His Gly Ser
                130                 135
```

<210> SEQ ID NO 83

```
<211> LENGTH: 5
<212> TYPE: PRT
<213> ORGANISM: Artificial Sequence
<220> FEATURE:
<223> OTHER INFORMATION: Protein or domain

<400> SEQUENCE: 83

Tyr Met Val Asp Lys
1               5

<210> SEQ ID NO 84
<211> LENGTH: 136
<212> TYPE: PRT
<213> ORGANISM: Artificial Sequence
<220> FEATURE:
<223> OTHER INFORMATION: Protein or domain

<400> SEQUENCE: 84

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Val Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 85
<211> LENGTH: 5
<212> TYPE: PRT
<213> ORGANISM: Artificial Sequence
<220> FEATURE:
<223> OTHER INFORMATION: Protein or domain

<400> SEQUENCE: 85

Tyr Met Leu Glu Lys
1               5

<210> SEQ ID NO 86
<211> LENGTH: 136
<212> TYPE: PRT
<213> ORGANISM: Artificial Sequence
<220> FEATURE:
<223> OTHER INFORMATION: Protein or domain

<400> SEQUENCE: 86

Glu Val Gln Leu Val Glu Ser Gly Gly Gly Val Val Gln Pro Gly Gly
1               5                   10                  15

Ser Leu Lys Leu Ser Cys Val Ala Ser Gly Thr Asp Phe Ser Ile Asn
            20                  25                  30

Phe Ile Arg Trp Tyr Arg Gln Ala Pro Gly Lys Gln Arg Glu Phe Val
        35                  40                  45
```

Ala Gly Phe Thr Ala Thr Gly Asn Thr Asn Tyr Ala Asp Ser Met Lys
    50                  55                  60

Gly Arg Phe Thr Ile Ser Arg Asp Asn Thr Lys Asn Ala Val Tyr Leu
65                  70                  75                  80

Gln Ile Asp Ser Leu Lys Pro Glu Asp Thr Ala Val Tyr Tyr Cys Tyr
                85                  90                  95

Met Leu Glu Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 87
<211> LENGTH: 136
<212> TYPE: PRT
<213> ORGANISM: Artificial Sequence
<220> FEATURE:
<223> OTHER INFORMATION: Protein or domain

<400> SEQUENCE: 87

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Met Ser Trp Val Arg Gln Ala Pro Gly Lys Gly Leu Glu Trp Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Tyr
                85                  90                  95

Met Leu Asp Lys Trp Gly Gln Gly Thr Gln Val Thr Val Ser Ser Ala
            100                 105                 110

Ala Ala Glu Gln Lys Leu Ile Ser Glu Glu Asp Leu Asn Gly Ala Ala
        115                 120                 125

His His His His His His Gly Ser
    130                 135

<210> SEQ ID NO 88
<211> LENGTH: 136
<212> TYPE: PRT
<213> ORGANISM: Artificial Sequence
<220> FEATURE:
<223> OTHER INFORMATION: Protein or domain

<400> SEQUENCE: 88

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Ile Arg Trp Val Arg Gln Ala Pro Gly Lys Gln Arg Glu Phe Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu

```
                65                  70                  75                  80
Gln Met Asn Ser Leu Arg Pro Glu Asp Thr Ala Val Tyr Tyr Cys Tyr
                    85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 89
<211> LENGTH: 136
<212> TYPE: PRT
<213> ORGANISM: Artificial Sequence
<220> FEATURE:
<223> OTHER INFORMATION: Protein or domain

<400> SEQUENCE: 89

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Met His Trp Val Arg Gln Ala Pro Gly Lys Gly Leu Glu Trp Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Tyr
                    85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
        130                 135

<210> SEQ ID NO 90
<211> LENGTH: 136
<212> TYPE: PRT
<213> ORGANISM: Artificial Sequence
<220> FEATURE:
<223> OTHER INFORMATION: Protein or domain

<400> SEQUENCE: 90

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Met Ser Trp Val Arg Gln Ala Pro Gly Lys Gln Arg Glu Phe Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Tyr
                    85                  90                  95
```

```
Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
    130                 135

<210> SEQ ID NO 91
<211> LENGTH: 136
<212> TYPE: PRT
<213> ORGANISM: Artificial Sequence
<220> FEATURE:
<223> OTHER INFORMATION: Protein or domain

<400> SEQUENCE: 91

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Ile Arg Trp Val Arg Gln Ala Pro Gly Lys Gly Leu Glu Trp Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Tyr
                85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125

His His His His His His Gly Ser
    130                 135

<210> SEQ ID NO 92
<211> LENGTH: 136
<212> TYPE: PRT
<213> ORGANISM: Artificial Sequence
<220> FEATURE:
<223> OTHER INFORMATION: Protein or domain

<400> SEQUENCE: 92

Glu Val Gln Leu Val Glu Ser Gly Gly Gly Val Val Gln Pro Gly Gly
1               5                   10                  15

Ser Leu Arg Leu Ser Cys Ala Ala Ser Gly Thr Asp Phe Ser Ile Asn
            20                  25                  30

Phe Ile His Trp Val Arg Gln Ala Pro Gly Lys Gly Leu Glu Trp Val
        35                  40                  45

Ala Gly Phe Thr Ala Thr Gly Asn Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Tyr
                85                  90                  95

Met Leu Asp Lys Trp Gly Gln Gly Thr Gln Val Thr Val Ser Ser Ala
                100                 105                 110

Ala Ala Glu Gln Lys Leu Ile Ser Glu Glu Asp Leu Asn Gly Ala Ala
            115                 120                 125
```

His His His His His His Gly Ser
    130                 135

<210> SEQ ID NO 93
<211> LENGTH: 558
<212> TYPE: PRT
<213> ORGANISM: Artificial Sequence
<220> FEATURE:
<223> OTHER INFORMATION: Protein or domain

<400> SEQUENCE: 93

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Lys Tyr Gly Lys Thr Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Asp Asp Gly Tyr Ser Trp Gly Gln Gly Thr Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

```
Asp Lys Val Ser Leu Thr Cys Met Ile Thr Asp Phe Phe Pro Glu Asp
            355                 360                 365

Ile Thr Val Glu Trp Gln Trp Asn Gly Gln Pro Ala Glu Asn Tyr Lys
        370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His Thr Glu Lys Ser
            420                 425                 430

Leu Ser His Ser Pro Gly Gly Gly Gly Met Ala Glu Val Gln Leu
            435                 440                 445

Val Glu Ser Gly Gly Gly Val Val Gln Pro Gly Gly Ser Leu Lys Leu
    450                 455                 460

Ser Cys Val Ala Ser Gly Thr Asp Phe Ser Ile Asn Phe Ile Arg Trp
465                 470                 475                 480

Tyr Arg Gln Ala Pro Gly Lys Gln Arg Glu Phe Val Ala Gly Phe Thr
                485                 490                 495

Ala Thr Gly Asn Thr Asn Tyr Ala Asp Ser Met Lys Gly Arg Phe Thr
            500                 505                 510

Ile Ser Arg Asp Asn Thr Lys Asn Ala Val Tyr Leu Gln Ile Asp Ser
            515                 520                 525

Leu Lys Pro Glu Asp Thr Ala Val Tyr Tyr Cys Tyr Met Leu Asp Lys
            530                 535                 540

Trp Gly Gln Gly Thr Gln Val Thr Val Ser Ser Ala Ala Ala
545                 550                 555

<210> SEQ ID NO 94
<211> LENGTH: 343
<212> TYPE: PRT
<213> ORGANISM: Artificial Sequence
<220> FEATURE:
<223> OTHER INFORMATION: Protein or domain

<400> SEQUENCE: 94

Asp Val Val Met Thr Gln Thr Pro Leu Ser Leu Pro Val Ser Leu Gly
1               5                   10                  15

Asp Gln Ala Ser Ile Ser Cys Arg Ser Gly Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160
```

```
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Asn Glu Cys Ser Gly Ser Gly Gly
    210                 215                 220
Gly Gly Gly Met Ala Glu Val Gln Leu Val Glu Ser Gly Gly Gly Val
225                 230                 235                 240
Val Gln Pro Gly Gly Ser Leu Lys Leu Ser Cys Val Ala Ser Gly Thr
                245                 250                 255
Asp Phe Ser Ile Asn Phe Ile Arg Trp Tyr Arg Gln Ala Pro Gly Lys
            260                 265                 270
Gln Arg Glu Phe Val Ala Gly Phe Thr Ala Thr Gly Asn Thr Asn Tyr
        275                 280                 285
Ala Asp Ser Met Lys Gly Arg Phe Thr Ile Ser Arg Asp Asn Thr Lys
    290                 295                 300
Asn Ala Val Tyr Leu Gln Ile Asp Ser Leu Lys Pro Glu Asp Thr Ala
305                 310                 315                 320
Val Tyr Tyr Cys Tyr Met Leu Asp Lys Trp Gly Gln Gly Thr Gln Val
                325                 330                 335
Thr Val Ser Ser Ala Ala Ala
            340

<210> SEQ ID NO 95
<211> LENGTH: 411
<212> TYPE: DNA
<213> ORGANISM: Artificial Sequence
<220> FEATURE:
<223> OTHER INFORMATION: VHH coding sequence

<400> SEQUENCE: 95
gaggtgcagc tggtggagtc tgggggaggc gtggtgcagc tgggggggtc tctaaaactc      60
tcctgcgtag cctcgggaac ggacttcagt ctgaatttta tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
caaatagaca gcctgaaacc tgaggacacg gccgtgtatt actgctatat gttggacaag     300
tggggccagg gaccccaggt caccgtctcc tcagcggccg cagaacaaaa actcatctca     360
gaagaggatc tgaatggggc cgcacatcac caccatcacc atgggagcta g              411

<210> SEQ ID NO 96
<211> LENGTH: 411
<212> TYPE: DNA
<213> ORGANISM: Artificial Sequence
<220> FEATURE:
<223> OTHER INFORMATION: VHH coding sequence

<400> SEQUENCE: 96
gaggtgcagc tggtggagtc tgggggaggc gtggtgcagc tgggggggtc tctaaaactc      60
tcctgcgtag cctcgggaac ggacttcagt atcaattaca tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
```

```
caaatagaca gcctgaaacc tgaggacacg gccgtgtatt actgctatat gttggacaag    300
tggggccagg ggacccaggt caccgtctcc tcagcggccg cagaacaaaa actcatctca    360
gaagaggatc tgaatggggc cgcacatcac caccatcacc atgggagcta g             411
```

```
<210> SEQ ID NO 97
<211> LENGTH: 411
<212> TYPE: DNA
<213> ORGANISM: Artificial Sequence
<220> FEATURE:
<223> OTHER INFORMATION: VHH coding sequence

<400> SEQUENCE: 97
gaggtgcagc tggtggagtc tgggggaggc gtggtgcagc ctggggggtc tctaaaactc     60
tcctgcgtag cctcgggaac ggacttcagt atcaattttta tacgctggta ccgccaggct   120
ccagggaagc agcgcgagtt cgtcgcagga attactgcga ctggtaacac aaactatgca   180
gactccatga agggccgatt caccatctcc agagacaaca ccaagaacgc ggtgtatctg   240
caaatagaca gcctgaaacc tgaggacacg gccgtgtatt actgctatat gttggacaag   300
tggggccagg ggacccaggt caccgtctcc tcagcggccg cagaacaaaa actcatctca   360
gaagaggatc tgaatggggc cgcacatcac caccatcacc atgggagcta g             411
```

```
<210> SEQ ID NO 98
<211> LENGTH: 411
<212> TYPE: DNA
<213> ORGANISM: Artificial Sequence
<220> FEATURE:
<223> OTHER INFORMATION: VHH coding sequence

<400> SEQUENCE: 98
gaggtgcagc tggtggagtc tgggggaggc gtggtgcagc ctggggggtc tctaaaactc     60
tcctgcgtag cctcgggaac ggacttcagt atcaattttta tacgctggta ccgccaggct   120
ccagggaagc agcgcgagtt cgtcgcagga ttttcagcga ctggtaacac aaactatgca   180
gactccatga agggccgatt caccatctcc agagacaaca ccaagaacgc ggtgtatctg   240
caaatagaca gcctgaaacc tgaggacacg gccgtgtatt actgctatat gttggacaag   300
tggggccagg ggacccaggt caccgtctcc tcagcggccg cagaacaaaa actcatctca   360
gaagaggatc tgaatggggc cgcacatcac caccatcacc atgggagcta g             411
```

```
<210> SEQ ID NO 99
<211> LENGTH: 411
<212> TYPE: DNA
<213> ORGANISM: Artificial Sequence
<220> FEATURE:
<223> OTHER INFORMATION: VHH coding sequence

<400> SEQUENCE: 99
gaggtgcagc tggtggagtc tgggggaggc gtggtgcagc ctggggggtc tctaaaactc     60
tcctgcgtag cctcgggaac ggacttcagt atcaattttta tacgctggta ccgccaggct   120
ccagggaagc agcgcgagtt cgtcgcagga tttactgcga ctggtaactc aaactatgca   180
gactccatga agggccgatt caccatctcc agagacaaca ccaagaacgc ggtgtatctg   240
caaatagaca gcctgaaacc tgaggacacg gccgtgtatt actgctatat gttggacaag   300
tggggccagg ggacccaggt caccgtctcc tcagcggccg cagaacaaaa actcatctca   360
gaagaggatc tgaatggggc cgcacatcac caccatcacc atgggagcta g             411
```

<210> SEQ ID NO 100
<211> LENGTH: 411
<212> TYPE: DNA
<213> ORGANISM: Artificial Sequence
<220> FEATURE:
<223> OTHER INFORMATION: VHH coding sequence

<400> SEQUENCE: 100

```
gaggtgcagc tggtggagtc tgggggaggc gtggtgcagc ctggggggtc tctaaaactc      60
tcctgcgtag cctcgggaac ggacttcagt atcaatttta tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
caaatagaca gcctgaaacc tgaggacacg gccgtgtatt actgctttat gttggacaag     300
tggggccagg ggacccaggt caccgtctcc tcagcggccg cagaacaaaa actcatctca     360
gaagaggatc tgaatggggc cgcacatcac caccatcacc atgggagcta g              411
```

<210> SEQ ID NO 101
<211> LENGTH: 411
<212> TYPE: DNA
<213> ORGANISM: Artificial Sequence
<220> FEATURE:
<223> OTHER INFORMATION: VHH coding sequence

<400> SEQUENCE: 101

```
gaggtgcagc tggtggagtc tgggggaggc gtggtgcagc ctggggggtc tctaaaactc      60
tcctgcgtag cctcgggaac ggacttcagt atcaatttta tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
caaatagaca gcctgaaacc tgaggacacg gccgtgtatt actgctatat tttggacaag     300
tggggccagg ggacccaggt caccgtctcc tcagcggccg cagaacaaaa actcatctca     360
gaagaggatc tgaatggggc cgcacatcac caccatcacc atgggagcta g              411
```

<210> SEQ ID NO 102
<211> LENGTH: 411
<212> TYPE: DNA
<213> ORGANISM: Artificial Sequence
<220> FEATURE:
<223> OTHER INFORMATION: VHH coding sequence

<400> SEQUENCE: 102

```
gaggtgcagc tggtggagtc tgggggaggc gtggtgcagc ctggggggtc tctaaaactc      60
tcctgcgtag cctcgggaac ggacttcagt atcaatttta tacgctggta ccgccaggct     120
ccagggaagc agcgcgagtt cgtcgcagga tttactgcga ctggtaacac aaactatgca     180
gactccatga agggccgatt caccatctcc agagacaaca ccaagaacgc ggtgtatctg     240
caaatagaca gcctgaaacc tgaggacacg gccgtgtatt actgctatat gattgacaag     300
tggggccagg ggacccaggt caccgtctcc tcagcggccg cagaacaaaa actcatctca     360
gaagaggatc tgaatggggc cgcacatcac caccatcacc atgggagcta g              411
```

<210> SEQ ID NO 103
<211> LENGTH: 411
<212> TYPE: DNA
<213> ORGANISM: Artificial Sequence
<220> FEATURE:
<223> OTHER INFORMATION: VHH coding sequence

<400> SEQUENCE: 103

```
gaggtgcagc tggtggagtc tggggaggc gtggtgcagc ctggggggtc tctaaaactc        60
tcctgcgtag cctcgggaac ggacttcagt atcaattta tacgctggta ccgccaggct       120
ccagggaagc agcgcgagtt cgtcgcagga tttactgcga ctggtaacac aaactatgca       180
gactccatga agggcgatt caccatctcc agagacaaca ccaagaacgc ggtgtatctg       240
caaatagaca gcctgaaacc tgaggacacg gccgtgtatt actgctatat ggtggacaag       300
tggggccagg ggacccaggt caccgtctcc tcagcggccg cagaacaaaa actcatctca       360
gaagaggatc tgaatggggc cgcacatcac caccatcacc atgggagcta g                411
```

<210> SEQ ID NO 104
<211> LENGTH: 411
<212> TYPE: DNA
<213> ORGANISM: Artificial Sequence
<220> FEATURE:
<223> OTHER INFORMATION: VHH coding sequence

<400> SEQUENCE: 104

```
gaggtgcagc tggtggagtc tggggaggc gtggtgcagc ctggggggtc tctaaaactc        60
tcctgcgtag cctcgggaac ggacttcagt atcaattta tacgctggta ccgccaggct       120
ccagggaagc agcgcgagtt cgtcgcagga tttactgcga ctggtaacac aaactatgca       180
gactccatga agggcgatt caccatctcc agagacaaca ccaagaacgc ggtgtatctg       240
caaatagaca gcctgaaacc tgaggacacg gccgtgtatt actgctatat gttggaaaag       300
tggggccagg ggacccaggt caccgtctcc tcagcggccg cagaacaaaa actcatctca       360
gaagaggatc tgaatggggc cgcacatcac caccatcacc atgggagcta g                411
```

<210> SEQ ID NO 105
<211> LENGTH: 411
<212> TYPE: DNA
<213> ORGANISM: Artificial Sequence
<220> FEATURE:
<223> OTHER INFORMATION: VHH coding sequence

<400> SEQUENCE: 105

```
gaggtgcagc tggtggagtc tggggaggc gtggtgcagc ctggggggtc tctacgtctc        60
tcctgcgcag cctcgggaac ggacttcagt atcaattta tgagctgggt tcgccaggct       120
ccagggaagg gtctggagtg ggtcgcagga tttactgcga ctggtaacac aaactatgca       180
gactccgtta agggcgatt caccatctcc agagacaacg caagaacac cctgtatctg       240
caaatgaata gcctgcgtcc tgaggacacg gccgtgtatt actgctatat gttggacaag       300
tggggccagg ggacccaggt caccgtctcc tcagcggccg cagaacaaaa actcatctca       360
gaagaggatc tgaatggggc cgcacatcac caccatcacc atgggagcta g                411
```

<210> SEQ ID NO 106
<211> LENGTH: 411
<212> TYPE: DNA
<213> ORGANISM: Artificial Sequence
<220> FEATURE:
<223> OTHER INFORMATION: VHH coding sequence

<400> SEQUENCE: 106

```
gaggtgcagc tggtggagtc tggggaggc gtggtgcagc ctggggggtc tctacgtctc        60
tcctgcgcag cctcgggaac ggacttcagt atcaattta tacgctgggt tcgccaggct       120
ccagggaagc agcgcgagtt cgtcgcagga tttactgcga ctggtaacac aaactatgca       180
```

```
gactccgtta aggggcgatt caccatctcc agagacaacg caaagaacac cctgtatctg    240
caaatgaata gcctgcgtcc tgaggacacg gccgtgtatt actgctatat gttggacaag    300
tggggccagg ggacccaggt caccgtctcc tcagcggccg cagaacaaaa actcatctca    360
gaagaggatc tgaatggggc cgcacatcac caccatcacc atgggagcta g             411
```

<210> SEQ ID NO 107
<211> LENGTH: 411
<212> TYPE: DNA
<213> ORGANISM: Artificial Sequence
<220> FEATURE:
<223> OTHER INFORMATION: VHH coding sequence

<400> SEQUENCE: 107

```
gaggtgcagc tggtggagtc tgggggaggc gtggtgcagc ctggggggtc tctacgtctc     60
tcctgcgcag cctcgggaac ggacttcagt atcaatttta tgcattgggt tcgccaggct    120
ccagggaagg gtctggagtg ggtcgcagga tttactgcga ctggtaacac aaactatgca    180
gactccgtta aggggcgatt caccatctcc agagacaacg caaagaacac cctgtatctg    240
caaatgaata gcctgcgtcc tgaggacacg gccgtgtatt actgctatat gttggacaag    300
tggggccagg ggacccaggt caccgtctcc tcagcggccg cagaacaaaa actcatctca    360
gaagaggatc tgaatggggc cgcacatcac caccatcacc atgggagcta g             411
```

<210> SEQ ID NO 108
<211> LENGTH: 411
<212> TYPE: DNA
<213> ORGANISM: Artificial Sequence
<220> FEATURE:
<223> OTHER INFORMATION: VHH coding sequence

<400> SEQUENCE: 108

```
gaggtgcagc tggtggagtc tgggggaggc gtggtgcagc ctggggggtc tctacgtctc     60
tcctgcgcag cctcgggaac ggacttcagt atcaatttta tgagctgggt tcgccaggct    120
ccagggaagc agcgcgagtt cgtcgcagga tttactgcga ctggtaacac aaactatgca    180
gactccgtta aggggcgatt caccatctcc agagacaacg caaagaacac cctgtatctg    240
caaatgaata gcctgcgtcc tgaggacacg gccgtgtatt actgctatat gttggacaag    300
tggggccagg ggacccaggt caccgtctcc tcagcggccg cagaacaaaa actcatctca    360
gaagaggatc tgaatggggc cgcacatcac caccatcacc atgggagcta g             411
```

<210> SEQ ID NO 109
<211> LENGTH: 411
<212> TYPE: DNA
<213> ORGANISM: Artificial Sequence
<220> FEATURE:
<223> OTHER INFORMATION: VHH coding sequence

<400> SEQUENCE: 109

```
gaggtgcagc tggtggagtc tgggggaggc gtggtgcagc ctggggggtc tctacgtctc     60
tcctgcgcag cctcgggaac ggacttcagt atcaatttta tacgctgggt tcgccaggct    120
ccagggaagg gtctggagtg ggtcgcagga tttactgcga ctggtaacac aaactatgca    180
gactccgtta aggggcgatt caccatctcc agagacaacg caaagaacac cctgtatctg    240
caaatgaata gcctgcgtcc tgaggacacg gccgtgtatt actgctatat gttggacaag    300
tggggccagg ggacccaggt caccgtctcc tcagcggccg cagaacaaaa actcatctca    360
```

```
gaagaggatc tgaatggggc cgcacatcac caccatcacc atgggagcta g      411
```

<210> SEQ ID NO 110
<211> LENGTH: 411
<212> TYPE: DNA
<213> ORGANISM: Artificial Sequence
<220> FEATURE:
<223> OTHER INFORMATION: VHH coding sequence

<400> SEQUENCE: 110

```
gaggtgcagc tggtggagtc tgggggaggc gtggtgcagc ctggggggtc tctacgtctc      60
tcctgcgcag cctcgggaac ggacttcagt atcaatttta tacattgggt tcgccaggct     120
ccagggaagg gtctggagtg ggtcgcagga tttactgcga ctggtaacac aaactatgca     180
gactccgtta aggggcgatt caccatctcc agagacaacg caaagaacac cctgtatctg     240
caaatgaata gcctgcgtcc tgaggacacg gccgtgtatt actgctatat gttggacaag     300
tggggccagg ggacccaggt caccgtctcc tcagcggccg cagaacaaaa actcatctca     360
gaagaggatc tgaatggggc cgcacatcac caccatcacc atgggagcta g              411
```

<210> SEQ ID NO 111
<211> LENGTH: 6
<212> TYPE: PRT
<213> ORGANISM: Artificial Sequence
<220> FEATURE:
<223> OTHER INFORMATION: Protein or domain

<400> SEQUENCE: 111

```
Gly Gly Gly Leu Gln Arg
1               5
```

<210> SEQ ID NO 112
<211> LENGTH: 15
<212> TYPE: PRT
<213> ORGANISM: Artificial Sequence
<220> FEATURE:
<223> OTHER INFORMATION: Protein or domain

<400> SEQUENCE: 112

```
Ala Ala Ala His His His His His His Gly Gly Gly Leu Gln Arg
1               5                   10                  15
```